(12) United States Patent
Attiyeh et al.

(10) Patent No.: US 12,390,451 B2
(45) Date of Patent: Aug. 19, 2025

(54) SMALL MOLECULE INHIBITOR OF THE JAK FAMILY OF KINASES

(71) Applicant: Janssen Pharmaceutica NV, Beerse (BE)

(72) Inventors: Edward F. Attiyeh, Villanova, PA (US); Kurtis E. Bachman, Chester Springs, PA (US); Gerald C. Chu, Philadelphia, PA (US); Tatiana Koudriakova, Poway, CA (US); David C. Polidori, Rancho Santa Fe, CA (US); Gary V. Borzillo, Upper Gwynedd, PA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 17/690,380

(22) Filed: Mar. 9, 2022

(65) Prior Publication Data

US 2022/0288041 A1    Sep. 15, 2022

Related U.S. Application Data

(60) Provisional application No. 63/232,356, filed on Aug. 12, 2021, provisional application No. 63/167,287, filed on Mar. 29, 2021, provisional application No. 63/159,726, filed on Mar. 11, 2021.

(51) Int. Cl.
| | | |
|---|---|---|
| *A61K 31/437* | (2006.01) | |
| *A61K 45/06* | (2006.01) | |
| *A61P 1/00* | (2006.01) | |
| *A61P 35/00* | (2006.01) | |
| *C12Q 1/6886* | (2018.01) | |

(52) U.S. Cl.
CPC ............ *A61K 31/437* (2013.01); *A61K 45/06* (2013.01); *A61P 1/00* (2018.01); *A61P 35/00* (2018.01); *C12Q 1/6886* (2013.01); *C12Q 2600/106* (2013.01); *C12Q 2600/156* (2013.01); *C12Q 2600/158* (2013.01)

(58) Field of Classification Search
CPC .................................................. A61K 31/437
USPC .......................................................... 514/293
See application file for complete search history.

(56) References Cited

U.S. PATENT DOCUMENTS

| | | | |
|---|---|---|---|
| 6,080,747 | A | 6/2000 | Uckun et al. |
| 8,163,767 | B2 | 4/2012 | Inoue et al. |
| 8,202,881 | B2 | 6/2012 | Purandare et al. |
| 8,426,411 | B2 | 4/2013 | Wishart et al. |
| 8,461,328 | B2 | 6/2013 | Babu et al. |
| 8,785,639 | B2 | 7/2014 | Wishart et al. |
| 8,841,078 | B2 | 9/2014 | Silvennoinen et al. |
| 8,962,629 | B2 | 2/2015 | Wishart et al. |
| 10,294,226 | B2 | 5/2019 | Koudriakova et al. |
| 10,364,246 | B2 | 7/2019 | Koudriakova et al. |
| 10,487,083 | B2 | 11/2019 | Kreutter |
| 10,981,911 | B2 | 4/2021 | Bacani et al. |
| 11,827,638 | B2 | 11/2023 | Bacani et al. |
| 2006/0270654 | A1 | 11/2006 | Pitts et al. |
| 2008/0261973 | A1 | 10/2008 | Capraro et al. |
| 2009/0264399 | A1 | 10/2009 | Inoue et al. |
| 2009/0312338 | A1 | 12/2009 | Wishart et al. |
| 2011/0077235 | A1 | 3/2011 | Chang et al. |
| 2011/0190489 | A1 | 8/2011 | Wishart et al. |
| 2011/0201593 | A1 | 8/2011 | Babu et al. |
| 2011/0311474 | A1 | 12/2011 | Wishart et al. |
| 2013/0216497 | A1 | 8/2013 | Wishart et al. |
| 2015/0210708 | A1 | 7/2015 | Wishart et al. |
| 2018/0170931 | A1 | 6/2018 | Koudriakova et al. |
| 2019/0177321 | A1 | 6/2019 | Koudriakova et al. |
| 2019/0177322 | A1 | 6/2019 | Kreutter et al. |
| 2019/0322665 | A1 | 10/2019 | Bacani et al. |
| 2020/0017498 | A1 | 1/2020 | Fernandes et al. |
| 2020/0165250 | A1* | 5/2020 | Fernandes ............ C07D 471/14 |
| 2020/0338051 | A1 | 10/2020 | Rizzolio |
| 2021/0206768 | A1 | 7/2021 | Bacani et al. |

FOREIGN PATENT DOCUMENTS

| | | |
|---|---|---|
| AU | 2012201894 A1 | 4/2012 |
| CL | 201201396 | 9/2012 |
| CL | 201901077 | 4/2019 |
| CL | 201901416 | 5/2019 |
| CL | 201901551 | 6/2019 |
| CL | 201901651 | 6/2019 |
| CL | 201901652 | 6/2019 |
| CL | 201901991 | 7/2019 |
| CL | 201901626 A | 10/2019 |
| CL | 201901633 A | 10/2019 |
| CL | 201903015 | 10/2019 |
| CN | 102127078 A | 7/2011 |
| CN | 102596954 A | 7/2012 |
| CN | 102712640 A | 10/2012 |

(Continued)

OTHER PUBLICATIONS

U.S. Appl. No. 16/243,874, filed Jan. 9, 2019, Koudriakova, Tatian etal.
U.S. Appl. No. 16/274,142, filed Feb. 12, 2019, Koudriakova, Tatiana etal.
U.S. Appl. No. 16/441,656, filed Jun. 14, 2019, Fernandes,Philippe etal.
U.S. Appl. No. 16/469,939, filed Jun. 14, 2019, Bacani, Genesis et al.
U.S. Appl. No. 16/581,081, filed Sep. 24, 2019, Fernandes, Philippe etal.
U.S. Appl. No. 17/377,249, filed Jul. 15, 2021, Fernandes, et al.
Alves De Medeiros, et al., JAK3 as an Emerging Target for Topical Treatment of Inflammatory Skin Diseases, PLoS One, 2016, pp. 1-16, 11(10): e0164080. doi:10.1371/journal.pone.0164080.

(Continued)

*Primary Examiner* — Taofiq A Solola

(57) ABSTRACT

Disclosed herein are JAK inhibitors that have low systemic toxicity. In some aspects, the disclosure includes methods for treating disease states, disorders, and conditions mediated by JAK, such as stomacho-intestinal system cancers, including colorectal cancers and familial adenomatous polyposis.

12 Claims, 35 Drawing Sheets

(56) References Cited

FOREIGN PATENT DOCUMENTS

| | | |
|---|---|---|
| CN | 110088105 A | 8/2019 |
| CN | 110312719 A | 10/2019 |
| EP | 1 173 435 B1 | 7/2003 |
| EP | 1 330 249 B1 | 4/2006 |
| EP | 1 509 524 B1 | 3/2008 |
| EP | 1 667 971 B1 | 6/2012 |
| EP | 1 902 029 B1 | 1/2014 |
| EP | 2 924 026 A1 | 9/2015 |
| EP | 2 870 137 B1 | 5/2018 |
| JP | 2013-517220 A | 5/2013 |
| JP | 2020-502141 A | 1/2020 |
| KR | 2014-0015162 A | 2/2014 |
| WO | 2007007919 A3 | 1/2007 |
| WO | WO 2007/007919 A2 | 1/2007 |
| WO | WO 2007/077949 A1 | 7/2007 |
| WO | WO 2009/152133 A1 | 12/2009 |
| WO | WO 2011/068881 A1 | 6/2011 |
| WO | WO2011068899 A1 | 6/2011 |
| WO | WO 2011/086053 A1 | 7/2011 |
| WO | WO 2013/007765 A1 | 1/2013 |
| WO | WO 2014/123167 A1 | 8/2014 |
| WO | WO 2015/144773 A1 | 10/2015 |
| WO | WO 2015/174376 A1 | 11/2015 |
| WO | WO 2016/191524 A1 | 12/2016 |
| WO | WO 2017/050938 A1 | 3/2017 |
| WO | WO 2017/079639 A1 | 5/2017 |
| WO | WO 2018/055551 A1 | 3/2018 |
| WO | WO2018077630 A1 | 5/2018 |
| WO | WO 2018/112379 A1 | 6/2018 |
| WO | WO 2018/112382 A1 | 6/2018 |
| WO | WO2018108671 A1 | 6/2018 |
| WO | WO2018109074 A1 | 6/2018 |
| WO | WO2018109607 A1 | 6/2018 |
| WO | WO2018111707 A1 | 6/2018 |
| WO | WO 2018/130563 A1 | 7/2018 |
| WO | WO2018138303 A1 | 8/2018 |
| WO | WO2018195397 A2 | 10/2018 |
| WO | WO2019239387 A1 | 12/2019 |

OTHER PUBLICATIONS

Amano, et al., JAK inhibitor JTE-052 regulates contact hypersensitivity by downmodulating T cell activation and differentiation, Journal of Dermatological Science, 2016, pp. 258-265, vol. 84.
Ambeu N'Ta C., et al., A practical multi-step synthesis of ethyl N-functionalized β-amino benzimidazole acrylate derivatives as promising cytotoxic agents, Molecular Diversity (2018) vol. 22, pp. 685-708.
Baumgart, et al., Inflammatory bowel disease: cause and immunobiology, Lancet, 2007, pp. 1627-1640, vol. 369.
Baumgart, et al., Inflammatory bowel disease: clinical aspects and established and evolving therapies. Lancet, 2007, pp. 1641-1657, vol. 369.
Baxter, et al., Acquired mutation of the tyrosine kinase JAK2 in human myeloproliferative disorders, Lancet, 2005, pp. 1054-1061, vol. 365.
Behbod, et al., Concomitant Inhibition of Janus Kinase 3 and Calcineurin-Dependent Signaling Pathways Synergistically Prolongs the Survival of Rat Heart Allografts, The Journal of Immunology, 2001, pp. 3724-3732, vol. 166.
Benveniste, et al., Involvement of the Janus Kinase/Signal Transducer and Activator of Transcription Signaling Pathway in Multiple Sclerosis and the Animal Model of Experimental Autoimmune Encephalomyelitis, Journal of Interferon & Cytokine Research, 2014, pp. 577-588, vol. 34, Issue 8.
Berge, et al., Pharmaceutical Salts, Journal of Pharmaceutical Sciences, 1977, pp. 1-19, vol. 66, No. 1.
Berthier, et al., Enhanced Expression of Janus Kinase-Signal Transducer and Activator of Transcription Pathway Members in Human Diabetic Nephropathy, Diabetes, 2009, pp. 469-477, vol. 58.
Bissonnette, et al., Topical tofacitinib for atopic dermatitis: a phase IIa randomized trial, British Journal of Dermatology, 2016, pp. 902-911, vol. 175.
Brosius, et al., JAK inhibition in the treatment of diabetic kidney disease, Diabetologia, 2016, pp. 1624-1627, vol. 59.
Bunnage, Mark E., Getting pharmaceutical R&D back on target, Nature Chemical Biology, 2011, pp. 335-339, vol. 7.
Busque, et al., Calcineurin-Inhibitor-Free Immunosuppression Based on the JAK Inhibitor CP-690,550: A Pilot Study in De Novo Kidney Allograft Recipients, American Journal of Transplantation, 2009, pp. 1936-1945, vol. 9.
Cargill, et al., A Large-Scale Genetic Association Study Confirms IL12B and Leads to the Identification of IL23R as Psoriasis-Risk Genes, The American Journal of Human Genetics, 2007, pp. 273-290, vol. 80.
Casanova, et al., Revisiting Crohn's disease as a primary immunodeficiency of macrophages, J. Exp. Med., 2009, pp. 1839-1843, vol. 206, No. 9.
Chan et al., Dose-dependent reduction in psoriasis severity as evidence of immunosuppressive activity of an oral Jak3 inhibitor in humans, Am. J. Transplant., 2006, S87, vol. 6.
Changelian, et al., Prevention of Organ Allograft Rejection by a Specific Janus Kinase 3 Inhibitor, Science, 2003, pp. 875-878, vol. 302.
Charmot, Dominique, Non-Systemic Drugs: A Critical Review, Current Pharmaceutical Design, 2012, pp. 1434-1445, vol. 18.
Clark, et al., Discovery and Development of Janus Kinase (JAK) Inhibitors for Inflammatory Diseases, Journal of Medicinal Chemistry, 2014, pp. 5023-5038, vol. 57.
Colligris, et al., Recent developments on dry eye disease treatment compounds, Saudi Journal of Ophthalmology, 2014, pp. 19-30, vol. 28.
Coskun, et al., Involvement of JAK/STAT signaling in the pathogenesis of inflammatory bowel disease, Pharmacological Research, 2013, pp. 1-8, vol. 76.
Danese, et al., JAK inhibition using tofacitinib for inflammatory bowel disease treatment: a hub for multiple inflammatory cytokines, Am J Physiol Gastrointest Liver Physiol, 2016, pp. G155-G162, vol. 310.
Duerr, et al., A Genome-Wide Association Study Identifies IL23R as an Inflammatory Bowel Disease Gene, Science, 2006, pp. 1461-1463, vol. 314.
Filipski, et al., Intestinal Targeting of Drugs: Rational Design Approaches and Challenges, Current Topics in Medicinal Chemistry, 2013, pp. 776-802, vol. 13.
Folster-Holst, et al., Topical hydrocortisone 17-butyrate 21-propionate in the treatment of inflammatory skin diseases: pharmacological data, clinical efficacy, safety and calculation of the therapeutic index, Pharmazie, 2016, pp. 115-121, vol. 71.
Fujimura, et al., Significance of Interleukin-6/STAT Pathway for the Gene Expression of REG Iα, a New Autoantigen in Sjögren's Syndrome Patients, in Salivary Duct Epithelial Cells, Clinic Rev Allerg Immunol, 2016, pp. 1-13, DOI 10.1007/s12016-016-8570-7.
Fukuyama, et al., Topically Administered Janus-Kinase Inhibitors Tofacitinib and Oclacitinib Display Impressive Antipruritic and Anti-Inflammatory Responses in a Model of Allergic Dermatitis, J Pharmacol Exp Ther, 2015, pp. 394-405, vol. 354.
Furumoto, et al., Tofacitinib Ameliorates Murine Lupus and Its Associated Vascular Dysfunction, Arthritis & Rheumatology, 2017, pp. 148-160, vol. 69 Issue 1.
Fyfe, Matthew C.T., Non-systemic Intestine-Targeted Drugs, Progress in Medicinal Chemistry, 2016, pp. 1-44, vol. 55.
Gaudana, et al., Ocular Drug Delivery, The AAPS Journal, 2010, pp. 348-360, vol. 12 Issue 3.
Ginzinger, Werner, et al., A Sar Study of Novel Antiproliferative Ruthenium and Osmium Complexes with Quinoxalinone Ligands in Human Cancer Cell Lines, J. Med. Chem. (2012) vol. 55, pp. 3398-3413.
Goropevsek, et al., The Role of STAT Signaling Pathways in the Pathogenesis of Systemic Lupus Erythematosus, Clinic Rev Allerg Immunol, May 23, 2016, pp. 1-18, DOI 10.1007/s12016-016-8550-y.
Gurzov, et al., The JAK/STAT pathway in obesity and diabetes, The FEBS Journal, 2016, pp. 3002-3015, vol. 283.

(56) References Cited

OTHER PUBLICATIONS

Hay, et al., Clinical development success rates for investigational drugs, Nature Biotechnology, 2014, pp. 40-51, vol. 32 Issue 1.
Helandr, et al., Surface area of the digestive tract—revisited, Scandinavian Journal of Gastroenterology, 2014, pp. 681-689, vol. 49.
Hirschmann, Ralph, et al., Nonpeptidal Peptidomimetics with a β-D-Glucose Scaffolding. A Partial Somatostatin Agonist Bearing a Close Structural Relationship to a Potent, Selective Substance P Antagonist, J. Am. Chem. Soc. (1992) vol. 114, pp. 9217-9218.
Honda, Masanori, et al., A Synthesis of (±)—Brefeldin A, Tetrahedron Letters (1981) vol. 22, No. 28, pp. 2679-2682.
James, et al., A unique clonal JAK2 mutation leading to constitutive signalling causes polycythaemia vera, Nature, 2005, pp. 1144-1148, vol. 434.
Jursic, Branko S., et al., A Simple Preparation of Amides from Acids and Amines by Heating of their Mixture, Synthetic Communications, (1993), vol. 23, No. 19. pp. 2761-2770.
Kawasaki, et al., Possible role of the JAK/STAT pathways in the regulation of T cell-interferon related genes in systemic lupus erythematosus, Lupus, 2011, pp. 1231-1239, vol. 20.
Kocienski, Philip J., Chapter 6.3.1: N-Sulfonyl Derivatives of Indoles, Pyrroles, and midazoles, Protecting Groups; Georg Thieme Verlag Stuttgart: NY, (1994), pp. 209-211.
Kola, et al., Can the pharmaceutical industry reduce attrition rates?, Nature Reviews/Drug Discovery, 2004, pp. 711-715, vol. 3.
Kontzias et al., Jakinibs: A new class of kinase inhibitors in cancer and autoimmune disease, Current Opinion in Pharmacology, 2012, pp. 464-470, vol. 12.
Kopf et al., Averting inflammation by targeting the cytokine environment, Nature Reviews/Drug Discovery, 2010, pp. 703-718, vol. 9.
Kornbluth, et al., Ulcerative Colitis Practice Guidelines in Adults: American College of Gastroenterology, Practice Parameters Committee, The American Journal of Gastroenterology, 2010, pp. 501-523, vol. 105.
Kralovics, et al., A Gain-of-Function Mutation of JAK2 in Myeloproliferative Disorders, The New England Journal of Medicine, 2005, pp. 1779-1790, vol. 352 Issue 17.
Kremer, et al., A Randomized, Double-Blind, Placebo-Controlled Trial of 3 Dose Levels of CP690,550 Versus Placebo in the Treatment of Active Rheumatoid Arthritis, Arthritis Rheum. 54 (annual meeting abstract), 2006, L40.
Kremer, et al., The Safety and Efficacy of a JAK Inhibitor in Patients with Active Rheumatoid Arthritis, Arthritis & Rheumatism, 2009, pp. 1895-1905, vol. 60 Issue 7.
Kumar, Vasantha et al., Synthesis of Some Novel 1,2-Disubstituted Benzimidazole-5-Carboxylates via One-Pot Method Using Sodium Dithionite and its Effect on N-Debenzylation, Synthetic Communications (2014) vol. 44, pp. 3414-3425.
Lalande, et al., Mycobacteria in Crohn's disease: how innate immune deficiency may result in chronic inflammation, Expert Review of Clinical Immunology, 2010, pp. 633-641, vol. 6 Issue 4.
Langholz, et al., Course of Ulcerative Colitis: Analysis of Changes in Disease Activity Over Years, Gastroenterology, 1994, pp. 3-11, vol. 107 Issue 01.
Leonardi, et al., Efficacy and safety of ustekinumab, a human interleukin-12/23 monoclonal antibody, in patients with psoriasis: 76-week results from a randomised, double-blind, placebo-controlled trial (Phoenix 1), Lancet, 2008, pp. 1665-1674, vol. 371.
Levine, et al., Activating Mutation in the Tyrosine Kinase JAK2 in Polycythemia Vera, Essential Thrombocythemia, and Myeloid Metaplasia with Myelofibrosis, Cancer Cell, 2005, pp. 387-397, vol. 7.
Li, et al., Effect of miR-19a and miR-21 on the JAK/STAT signaling pathway in the peripheral blood mononuclear cells of patients with systemic juvenile idiopathic arthritis, Experimental and Therapeutic Medicine, 2016, pp. 2531-2536, vol. 11.

Liu, et al., Therapeutic Efficacy of Suppressing The JAK/STAT Pathway In Multiple Models Of Experimental Autoimmune Encephalomyelitis, The Journal of Immunology, 2014, pp. 59-72, vol. 192.
Liu, Zhenming et al., Identification of Small-Molecule Inhibitors against Human Leukocyte Antigen-Death Receptor 4 (HLA-DR4) Through a Comprehensive Strategy, J. Chem. Inf. Model. (2011) vol. 51, pp. 326-334.
Marks, et al., Crohn's Disease: an Immune Deficiency State, Clinic Rev Allerg Immunol, 2010, pp. 20-31, vol. 38.
Menet, et al., Triazolopyridines as Selective JAK1 Inhibitors: From Hit Identification to GLPG0634, Journal of Medicinal Chemistry, 2014, pp. 9323-9342, vol. 57.
Nangia, Ashwini, Pseudopolymorph: Retain This Widely Accepted Term, Crystal Growth & Design, 2006, pp. 2-4, vol. 6 Issue 1.
Neurath, Markus F., Cytokines in inflammatory bowel disease, Nature Reviews/Immunology, 2014, pp. 329-342, vol. 14.
NIDDK (National Institute of Diabetes, and Digestive and Kidney Diseases, National Institutes of Health, US Department of Health and Human Services, <http://spotidoc.com/doc/71780/crohns-disease---national-digestive- diseases-information>, accessed Nov. 29, 2016.
Nielsen, et al., Will novel oral formulations change the management of inflammatory bowel disease?, Expert Opinion On Investigational Drugs, 2016, pp. 709-718, vol. 25 Issue 6.
Nishimoto, et al., Study of active controlled monotherapy used for rheumatoid arthritis, an IL-6 inhibitor (SAMURAI): evidence of clinical and radiographic benefit from an x ray reader-blinded randomised controlled trial of tocilizumab, Ann Rheum Dis, 2007, pp. 1162-1167, vol. 66.
Norman, Peter, Selective JAK inhibitors in development for rheumatoid arthritis, Expert Opinion on Investigational Drugs, 2014, pp. 1067-1077, vol. 23 Issue 8.
Oda, Shinichi et al., Development of Safe One-Pot Synthesis of N-1- and C-2-Substituted Benzimidazole via Reductive Cyclization of o-Nitroarylamine Using $Na_2S_2O_4$, Org. Process Res. Dev. (2012) vol. 16, pp. 96-101.
O'Shea, et al., Janus kinase inhibitors in autoimmune diseases, Ann Rheum Dis, 2013, pp. ii111-ii115, vol. 72.
O'Shea, et al., A New Modality for Immunosuppression: Targeting the JAK/STAT Pathway, Nature Reviews/Drug Discovery, 2004, pp. 555-564, vol. 3.
O'Shea, et al., JAKs and STATs in Immunity, Immunodeficiency, and Cancer, The New England Journal of Medicine, 2013, pp. 161-170, vol. 368.
Özil, Musa et al., A simple and efficient synthesis of benzimidazoles containing piperazine or morpholine skeleton at C-6 position as glucosidase inhibitors with antioxidant activity, Bioorganic Chemistry (2018) vol. 76, pp. 468-477.
Panes, et al., Efficacy and safety of oral tofacitinib for induction therapy in patients with moderate-to-severe Crohn's disease: results of a Phase 2b randomised placebo-controlled trial. J. Crohn's Colitis, 2016, S18-S19, vol. 10.
Papp, et al., Efficacy and safety of tofacitinib, an oral Janus kinase inhibitor, in the treatment of psoriasis: a Phase 2b randomized placebo-controlled dose-ranging study, British Journal of Dermatology, 2012, pp. 668-677, vol. 167.
Patil, et al., Pulmonary drug delivery strategies: A concise, systematic review, Lung India, 2012, pp. 44-49, vol. 29 Issue 1.
Pesu et al., Therapeutic targeting of Janus kinases, Immunological Reviews, 2008, pp. 132-142, vol. 223.
Qiao, et al., Pharmaceutical cocrystals: An overview, International Journal of Pharmaceutics, 2011, pp. 1-11, vol. 419.
Reinisch, et al., Adalimumab for induction of clinical remission in moderately to severely active ulcerative colitis: results of a randomised controlled trial, Gut, 2011, pp. 780-787, vol. 60.
Rylander, P.N., Chapter 8: Hydrogenation of Nitro Compounds, Hydrogenation Methods: Academic Press: NY, (1985) pp. 104-116.
Rylander, P.N., Choosing and Using Noble Metal Hydrogenation Catalysts, Aldrichimica Acta (1979), vol. 12, No. 3, pp. 53-57.
Sandborn, et al., A Phase 2 Study of Tofacitinib, an Oral Janus Kinase Inhibitor, in Patients With Crohn's Disease, Clinical Gastroenterology and Hepatology, 2014, pp. 1485-1493, vol. 12 Issue 9.

(56) References Cited

OTHER PUBLICATIONS

Sandborn, et al., Efficacy and safety of oral tofacitinib as induction therapy in patients with moderate-to-severe ulcerative colitis: results from 2 phase 3 randomised controlled trials, J. Crohn's Colitis, 2016, S15-S, vol. 10.
Sandborn, et al., Tofacitinib, an Oral Janus Kinase Inhibitor, in Active Ulcerative Colitis, N Engl J Med, 2012, pp. 616-624, vol. 367 Issue 7.
Segal, et al., Repeated subcutaneous injections of IL12/23 p40 neutralising antibody, ustekinumab, in patients with relapsing-remitting multiple sclerosis: a phase II, double-blind, placebo-controlled, randomised, dose-ranging study, Lancet Neurol, 2008, pp. 796-804, vol. 7.
Shan, et al., The role of cocrystals in pharmaceutical science, Drug Discovery Today, 2008, pp. 440-446, vol. 13 Nos. 9/10.
Stephenson et al., Physical Stability of Salts of Weak Bases in the Solid-State, Journal of Pharmaceutical Sciences, 2011, pp. 1607-1617, vol. 100 Issue 5.
Strober, et al., Proinflammatory Cytokines in the Pathogenesis of Inflammatory Bowel Diseases, Gastroenterology, 2011, pp. 1756-1767, vol. 140 Issue 6.
Thakuria, et al., Pharmaceutical cocrystals and poorly soluble drugs, International Journal of Pharmaceutics, 2013, pp. 101-125, vol. 453.
Thomas et al., The role of JAK/STAT signaling in the pathogenesis, prognosis and treatment of solid tumours, British Journal of Cancer, 2015, pp. 365-371, vol. 113.
Thompson, et al., Anti cytokine therapy in chronic inflammatory arthritis, Cytokine, 2016, pp. 92-99, vol. 86.
Torchilin, Vladimir P., Drug targeting, European Journal of Pharmaceutical Sciences, 2000, pp. S81-S91, vol. 11 Suppl. 2.
Travis et al., European evidence-based Consensus on the management of ulcerative colitis: Current management, Journal of Crohn's and Colitis, 2008, pp. 24-62, vol. 2.
Vale, Kara, Targeting the JAK-STAT pathway in the treatment of 'Th2-high' severe asthma, Future Med. Chem., 2016, pp. 405-419, vol. 8 Issue 4.
Vermeire, et al., Filgotinib (GLPG0634), an Oral JAK1 Selective Inhibitor, Induces Clinical Remission in Patients With Moderate-to-Severe Crohn's Disease: Results From the Phase 2 FITZROY Study Interim Analysis, Gastroenterology, 2016, S-1267, vol. 150.
Waldner et al., Master regulator of intestinal disease: IL-6 in chronic inflammation and cancer development, Seminars in Immunology, 2014, pp. 75-79, vol. 26.
Waring, et al., An analysis of the attrition of drug candidates from four major pharmaceutical companies, Nature Reviews/Drug Discovery, 2015, pp. 475-486, vol. 14.
Wernig, et al., Efficacy of TG101348, a Selective JAK2 Inhibitor, in Treatment of a Murine Model of JAK2V617F-Induced Polycythemia Vera, Cancer Cell, 2008, pp. 311-320, vol. 13.
Wilding, et al., Targeting of Drugs and Vaccines to the Gut, Pharmac. Ther., 1994, pp. 97-124, vol. 62.
Williams et al., A randomized placebo-controlled study of INCB018424, a selective Janus kinase1&2 (JAK1&2) inhibitor in rheumatoid arthritis (RA), Arthritis Rheum., 2008, S431, vol. 58.
Wolk, et al., New targeting strategies in drug therapy of inflammatory bowel disease: mechanistic approaches and opportunities, Expert Opin. Drug Deliv., 2013, pp. 1275-1286, vol. 10 Issue 9.
Xing, et al., Alopecia areata is driven by cytotoxic T lymphocytes and is reversed by JAK inhibition, Nature Medicine, 2014, pp. 1043-1051, vol. 20 Issue 9.
Yamamoto-Furusho, et al., Crohn's disease: Innate immunodeficiency?, World J Gastroenterol, 2006, pp. 6751-6755, vol. 12 Issue 42.
Yan, et al., Role of the JAK/STAT signaling pathway in regulation of innate immunity in neuroinflammatory diseases, Clin. Immunol., 2016, http://dx.doi.org/10.1016/j.clim.2016.09.014.
Zak, et al., Discovery and Optimization of C-2 Methyl Imidazopyrrolopyridines as Potent and Orally Bioavailable JAK1 Inhibitors with Selectivity over JAK2, J. Med. Chem, 2012, pp. 6176-6193, vol. 55.
Zak, Mark et al., Identification of C-2 Hydroxyethyl Imidazopyrrolopyridines as Potent JAK1 Inhibitors with Favorable Physicochemical Properties and High Selectivity over JAK2, J. Med. Chem. 2013, 56, 4764-4785.
Zakhs, E.R., et al., Synthesis and Photochromic Properties of 2-(3-Nitro-2-pyridylmethyl)benzazoles, Russian Journal of General Chemistry, (2001) vol. 71, No. 7, pp. 1076-1087. Translated from Zhurnal Obshchei Khimil, (2001) vol. 71. No. 7, pp. 1142-1153.
International Search Report and Written Opinion dated May 11, 2018, for International Application PCT/US2017/066744.
International Search Report and Written Opinion dated Apr. 4, 2018, for International Application PCT/US2017/066754.
International Search Report and Written Opinion dated Dec. 2, 2019, for International Application PCT/IB2019/055005.
Ma, Christopher et al., "Systematic review with meta-analysis: efficacy and safety of oral Janus kinase inhibitors for inflammatory bowel disease", Aliment Pharmacol Ther., (2019) vol. 50, pp. 5-23.
Leonard, K., et al., "Discovery of a Gut-Restricted JAK Inhibitor for the Treatment of Inflammatory Bowel Disease", J.Med.Chem. 2020, vol. 63, pp. 2915-2929.
Notification of Decision Concerning Request for Rectification dated Jun. 15, 2020 for International Application No. PCT/IB2019/055005, 2 pages.
U.S. Appl. No. 17/355,472, filed Jun. 23, 2021, Koudriakova, et al.
Labadie, S., et al., "Structure-based discovery of C-2 substituted imidazo-pyrrolopyridine JAK1 inhibitors with improved selectivity over JAK2", (2012), Bioorganic & Medicinal Chemistry Letter, vol. 22, No. 24, pp. 7627-7633.
Labadie, S., et al., "Design and evaluation of novel 8-oxo-pyridopyrimidine Jak1/2 inhibitors", (2013), Bioorganic & Medicinal Chemistry Letters, vol. 23, No. 21, pp. 5923-5930.
Albini, A., et al., "Cancer Prevention and Interception: A New Era for Chemopreventive Approaches", (2016), Clin. Cancer Res, vol. 22, No. 17, pp. 4322-4327.
Chikano, S., et al., "IL-18 and IL-12 induce intestinal inflammation and fatty liver in mice in an IFN-y dependent manner". (2000), Gut, vol. 47, pp. 779-786.
Hedvat, M., et al., "The JAK2 Inhibitor AZD1480 Potently Blocks Stat3 Signaling and Oncogensis in Solid Tumors", (2009). Cancel Cell, vol. 16, pp. 487-497.
Jasperson, K.W., et al., "APC-Associated Polyposis Conditions", (1998), U.S. National Library of Medicine, https://www.ncbi.nim.nih.gov/books/, pp. 1-38.
Langowski, J.L., et al., "IL-23 promotes tumor incidence and growth", (2006), Nature, vol. 442, No. 7101, pp. 461-465.
Leonard, K.A., et al., "Discovery of a Gut-Restricted JAK Inhibitor for the Treatment of Inflammatory Bowel Disease", (2020), Journal of Medicinal Chemistry, vol. 63, No. 6, pp. 2915-2929.
Li, M., et al., "Prognostic Role of Phospho-STAT3 in Patients with Cancers of the Digestive System: A Systematic Review and Meta-Analysis", (2015), PLOS One, vol. 10, No. 5, pp. 1-16.
Nold-Petry, C.A., et al., "Gp96 Peptide Antagonist gp96-II Confers Therapeutic Effects in Murine Intestinal Inflammation", (2017), Front Immunol., vol. 8, article 1531, pp. 1-13.
Phillips, R.K.S., et al., "A randomized, double blind, placebo controlled study of celecoxib, a selective cyclooxygenase 2 inhibitor, on duodenal polyposis in familial adenomatous polyposis" (2002), Gut, vol. 50, pp. 857-860.
Rice, P.L., et al., "Sulindac Sulfide Inhibits Epidermal Growth Factor-induced Phosphorylation of Extracellular-regulated Kinase ½ and Bad in Human Colon Cancer Cells", (2003), Cancer Research, vol. 63, pp. 616-620.
Wick, E.C., et al., "Stat3 Activation in Murine Colitis Induced by Enterotoxigenic Bacteroides fragilis", (2014), Inflamm Bowel Dis, vol. 20, No. 5, pp. 821-834.
Yen, T., et al., "APC-Associated Polyposis Conditions". (1998), U.S. National Library of Medicine, https://www.ncbi.nlm.nih.gov/books/, pp. 1-35.
International Search Report from PCT/EP2022/056018 mailed Jul. 7, 2022.

(56) References Cited

OTHER PUBLICATIONS

Dinarvand et al., "Familial Adenomatous Polyposis Syndrome: An Update and Review of Extraintestinal Manifestations", Archives of Pathology & Laboratory Medicine, vol. 143, No. 11, pp. 1382-1398, Nov. 2019.

* cited by examiner

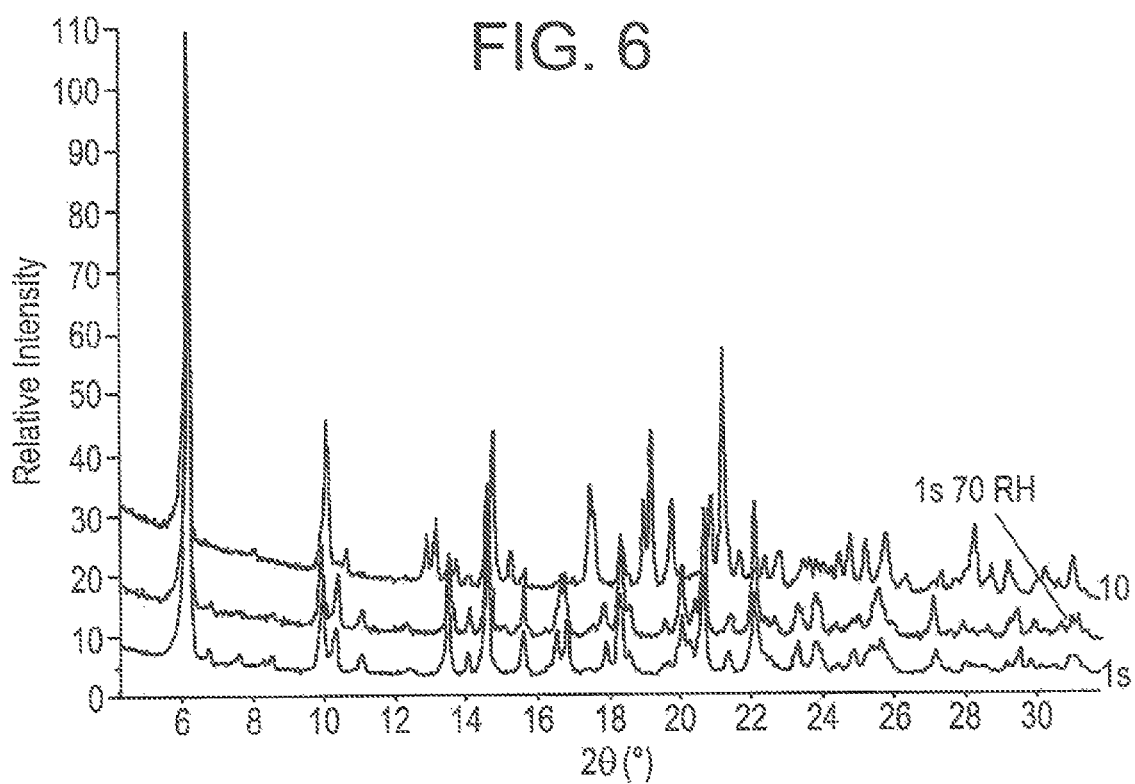

SMALL MOLECULE INHIBITOR OF THE JAK FAMILY OF KINASES

CLAIM OF PRIORITY

This application claims priority to U.S. Provisional Application No. 63/159,726 filed on Mar. 11, 2021, U.S. Provisional Application No. 63/167,287 filed on Mar. 29, 2021, and U.S. Provisional Application No. 63/232,356 filed on Aug. 12, 2021, each of which is incorporated by reference in its entirety.

FIELD OF THE INVENTION

The present invention relates to methods of use of a JAK inhibitor and pharmaceutical compositions comprising such inhibitor. This compound and pharmaceutical compositions are envisaged to be useful for preventing or treating disease states, disorders, and conditions mediated by JAK.

BACKGROUND

About one in three women and about one in two men will reportedly have cancer diagnosed, and about one in four will die from cancer. See A. Albini, et al., Clin. Cancer Res. 22(17), 4322-27 (2016) "Cancer prevention and interception: A new era for chemopreventive approaches". A significant number of cancers develop in the following organs of the gastro-intestinal tract: Stomach, small intestine, colon, rectum and anus. Stomach cancer, or gastric cancer, is reported as being the fourth in the ranking of most common cancers, and the second in the ranking of worldwide cancer mortality. G. Bjelakovic, et al., The Cochrane Database of Systematic Reviews (3): CD004183 (2008) "Antioxidant supplements for preventing gastrointestinal cancers". Small intestine cancer reportedly affects 9,000 people a year in the US. More than 22,000 cases of stomach cancer per year are reportedly diagnosed in the US. About 145,000 colon cancer cases per year are reportedly diagnosed in the US. More than 40,000 cases of rectal cancer per year are reportedly diagnosed in the US. Of these cancers, those affecting the colon or rectum, known as colorectal cancer ("CRC"), account for over 180,000 cases per year in the US. According to the American Cancer Society, 140,250 new cases of colorectal cancer are expected to be diagnosed in the US in 2018, and 50,600 deaths due to colorectal cancer are expected to occur in the US in 2018. The stomach, small intestine, and large intestine (the latter including the colon, rectum and anus) are here collectively referred to as the stomacho-intestinal system ("SIS") and cancer in any of such organs is referred to as stomacho-intestinal system cancer ("SISC"). Preventing the onset of SISC, and especially the onset of CRC, whether in reference to its first appearance or at a recurrence stage, is an unmet medical need. This preventive action is herein referred to as SISC interception, or CRC interception when referring to colorectal cancer interception.

FAP is the most common adenomatous polyposis syndrome. It is an autosomal dominant inherited disorder characterized by the early onset of hundreds to thousands of adenomatous polyps throughout the colon. If left untreated, nearly all patients with this syndrome develop colon cancer by age 35 to 40. Prophylactic colectomy is the standard of care, but patients remain at risk for malignant transformation of duodenal and rectal polyps. Multiple studies with both unselective and selective cyclooxygenase inhibitors (such as sulindac or celecoxib) have shown that anti-inflammatory agents can inhibit the formation of colorectal adenomatous polyps. (R. K. S. Phillips, et al. Gut 50, 857-860 (2002) "A randomized, double blind, placebo controlled study of celecoxib, a selective cyclooxygenase 2 inhibitor, on duodenal polyposis in familial adenomatous polyposis"; P. Rice, et al. Cancer Res. 63, 616-620 (2003) "Sulindac sulfide inhibits epidermal growth factor-induced phosphorylation of extracellular-regulated kinase ½ and Bad in human colon cancer cells") Toxicities associated with these agents have prevented their further development. There is a high unmet need for new treatment options to reduce polyp burden, delay or eliminate the need for colectomy, and intercept the development of adenocarcinomas in individuals with FAP. Polyps from patients with FAP as well as polyps that lead to sporadic CRC show inflammation associated with the interleukin (IL)-23/IL-17/Janus kinase (JAK)/signal transducers and activators of transcription STAT3 pathway. Compared to normal-appearing adjacent nonadenomatous epithelium and its immune surrounding, the epithelium of the adenoma is accompanied by a markedly increased immune infiltrate. This infiltrate is characterized by STAT3 pathway activation shown by IL-17 and p-STAT3 expression. In addition the adenomatous epithelium itself may be focally activated. Adenomas with high grade dysplasia can show a greater activated IL-17 and p-STAT3 immune infiltrate and a more broadly distributed expression of epithelial p-STAT3. These findings suggest that this inflammatory path leads to further mutagenesis and tumor development. It has also been reported that both immune and epithelial STAT3 activaion contribute to oncogenesis in murine models. E. C. Wick, et al., Inflamm. Bowel Dis. 20(5), 821-34 (2014) "Stat3 activation in murine colitis induced by enterotoxigenic *Bacteroides fragilis*". Specifically, IL-23 is linked to tumor growth and progression in CRC, and adenomas with high-grade dysplasia showed elevated levels of IL-17A and phosphorylated STAT3. (J. L. Langowski, et al. Nature 442(7101), 461-465 (2006) "IL-23 promotes tumour incidence and growth"). The excessive inflammatory response in the gastrointestinal tract is mediated by inflammatory cytokines such as tumor necrosis factor (TNF), interferon-gamma (IFN$\gamma$), IL-1, IL-6, IL-12, IL-21, and IL-23 that exert their effects on cells of the innate and adaptive immune system including T and B lymphocytes, epithelial cells, macrophages and dendritic cells (DC) (M. Coskun, et al., Pharmacological Research 76, 1-8 (2013) cited above; S. Danese, et al. Am J Physiol Gastrointest Liver Physiol. 310, G155-162 (2016) "JAK inhibition using tofacitinib for inflammatory bowel disease treatment: a hub for multiple inflammatory cytokines"; Neurath M. Nat. Rev. Immunol. 14, 329-342 (2014) "Cytokines in inflammatory bowel disease"; S. Vermeire, et al. Gastroenterology 150, 51267 (2016) "Filgotinib (GLPG0634), an Oral JAK1 Selective Inhibitor, Induces Clinical Remission in Patients With Moderate-to-Severe Crohn's Disease: Results From the Phase 2 FITZROY Study Interim Analysis [DDW abstract 812c]") The JAK family, JAK1, JAK2, JAK3 and Tyk2, are non-receptor tyrosine kinases that play a pivotal role in the response to many such cytokines (J. O'Shea, N. Engl. J. Med. 368, 161-170 (2013) "JAKs and STATs in immunity, immunodeficiency, and cancer"). Following receptor ligation, associated JAK homo- or heterodimers are phosphorylated and activated enabling the subsequent recruitment, phosphorylation and activation of the STAT family of transcription factors. Phosphorylated STATs translocate to the nucleus and induce gene transcription of several chemokines, cytokines, and proteases implicated in the pathogenesis of FAP (M. Coskun, et al., Pharmacological Research 76, 1-8 (2013) cited above). This JAK-STAT pathway is the signaling mechanism for many cytokines that play a role in the pathogenesis of GI cancers. (M. Li, et al. PLoS One 10(5), e0127356 (2015) "Prognostic role of phospho-STAT3 in patients with cancers of the digestive system: a systematic review and meta-analysis"). The JAK-STAT pathway is common to multiple inflammatory cytokine responses, it therefore offers an attractive therapeutic target to prevent the excessive inflammatory response associated with FAP and adenomas associasted with sporadic CRC and to restore mucosal homeostasis in order to attempt to intercept the development of adenocarcinomas in the GI tract. Investigational and marketed orally administered systemically bio-available pan-JAK inhibitors have various off-target effects apparently limiting high(er) dosing, such as elevated lipids (low- and high-density lipoproteins) and cytopenia's, including neutropenia, lymphopenia, and anemia, as well as elevated liver enzymes. Therefore, therapeutic inhibition of JAKs with exposure limited to the intestinal tract would offer an opportunity to achieve efficacy in JAK-driven diseases of the intestinal tract, including FAP, SISC and CRC.

In reference to FIG. 1, an orally administered medication can in principle follow the gastro-intestinal tract from the mouth to the esophagus (1), to the stomach (2) through the duodenum (3) to the jejunum (4), then to the ileum (5), and then to the colon (6). The relative absorption areas for such various parts are approximately 60% for the jejunum (4), approximately 26% for the ileum (5), and approximately 13% for the colon (6). Absorption through these various gastro-intestinal regions can lead to the onset of systemic distribution that in turn could lead to undesirable side-effects. The gastro-intestinal tract has a very large surface area. See, for example, H. F. Helander, et al., Surface area of the digestive tract—revisited, Scandinavian Journal of Gastroenterology 49(6), 681-89 (2014); and K. J. Filipski, et al., Intestinal Targeting of Drugs: Rational Design Approaches and Challenges Current Topics in Medicinal Chemistry 13, 776-802 (2013). Such an extensive absorption surface area favors systemic distribution of substances that can go through the walls of the various parts of the intestinal tract and into the blood stream, and in turn have the potential to lead to unwanted side effects of a systemically distributed substance. Systemic distribution is represented by dashed line arrows in FIG. 1 as permeating through the colon walls for simplified illustrative purposes, but such distribution is not limited to the colon walls, for it also can take place through the walls of other parts of the gastrointestinal tract shown in FIG. 1, such as those of the small intestine. It is also understood that the dashed arrow lines in FIG. 1 represent systemic distribution beyond the gastrointestinal track as such systemic distribution is known to take place in reference to the gastrointestinal track physiology, and that such dashed line arrows simply refer in a schematic illustrative manner to such systemic distribution. See, for example, Current Topics in Medicinal Chemistry 13, 777-80 (2013), cited above, for a description of intestinal tissue, transport across the same, and metabolism.

Because some known JAK inhibitors have adverse effects that are associated with their systemic effects, it is desirable to find new JAK inhibitors as active substances for the treatment and prevention of diseases of the intestinal tract, including FAP, SISC and CRC.

BRIEF SUMMARY OF THE INVENTION

Disclosed herein are JAK inhibitors that have low systemic toxicity. In some aspects, the invention includes a JAK inhibitor represented by compound of Formula I:

2-(1-((1r,4r)-4-(Cyanomethyl)cyclohexyl)-1,6-dihydroimidazo[4,5-d]pyrrolo[2,3-b]pyridin-2-yl)-N-(2-hydroxy-2-methylpropyl)acetamide,

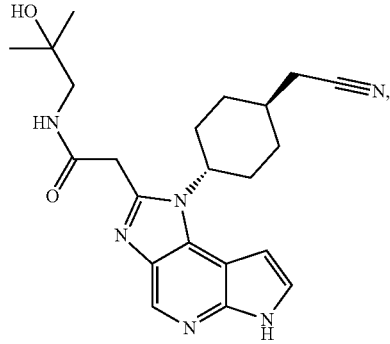

(Formula I)

or a pharmaceutically acceptable salt, solvate, and polymorph thereof, and methods of using compound of Formula I in the treatment of disease states, disorders, and conditions mediated by JAK. The term "compound of Formula I" is intended to encompass compound of Formula I or a pharmaceutically acceptable salt thereof, or a solvate of compound of Formula I or a pharmaceutically acceptable salt thereof, or a polymorph or co-crystal of any of the foregoing whether in a solvent-free form or in any one of hydrated and/or solvated forms as illustrated herein, hereafter "compound of Formula I or a pharmaceutically acceptable salt, solvate and polymorph thereof". A compound of Formula I is also referred to as an "active agent" or "active agents".

Aspects of the present invention relate to compound of Formula I, pharmaceutical compositions containing it, methods of using them as JAK inhibitors and methods for using them in the treatment of disease states, disorders, and conditions mediated by JAK.

In some aspects, a method of treating or preventing the onset of stomacho-intestinal system cancer (SISC), and especially the onset of colorectal cancer (CRC), comprises administering to the subject a composition comprising a therapeutically effective amount of compound of Formula I or a pharmaceutically acceptable salt, solvate and polymorph thereof.

In some aspects, a methods of treating or preventing a subject from suffering from familial adenomatous polyposis ("FAP") comprises administering to the subject a composition comprising a therapeutically effective amount of compound of Formula I or a pharmaceutically acceptable salt, solvate and polymorph thereof.

Aspects of this invention exhibit pan-JAK inhibition effects with local GI effects and low or negligible systemic effects. Furthermore, aspects of this invention with such features can be orally administered.

Additional aspects, features, and advantages of the invention will be apparent from the following detailed description and through practice of the invention.

BRIEF DESCRIPTION OF FIGURES

FIG. 6. HR-XRPD diffractograms of embodiment 1s in its initial form ("1s"), after a four-day exposure to 40° C. and 70% relative humidity ("1s 70 RH"), and after a four-day exposure to 25° C. and 100% relative humidity ("10").

DSC of embodiment 6 showing an endotherm of 95.8 J/g at 194.4° C. due to sample melt.

Figure 20A:
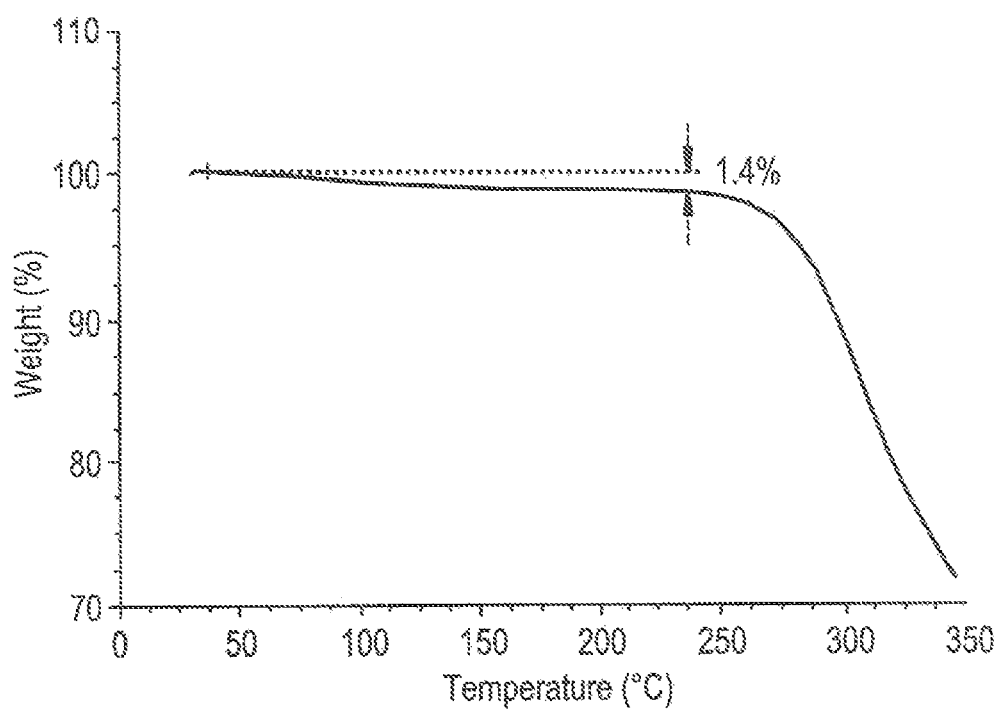
Figure 20B:
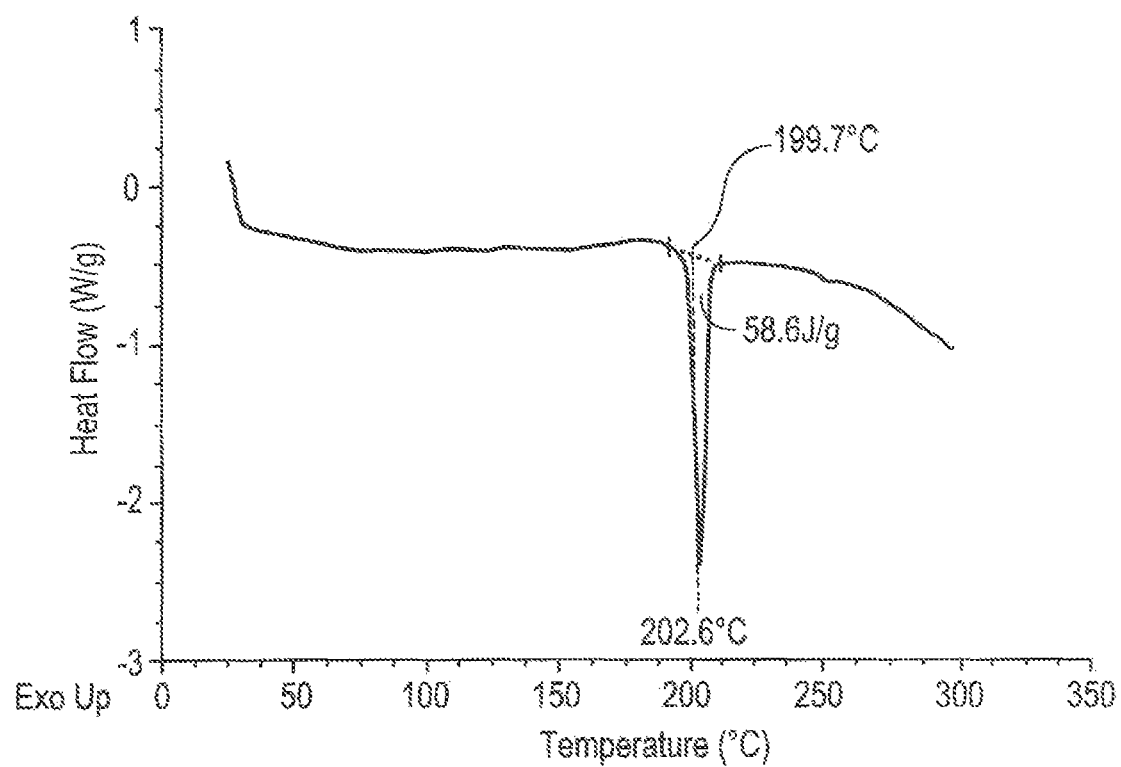

FIGS. 20A-B. (A) TGA of embodiment 8 showing a 1.4% w/w loss between 40° C. and 240° C., which corresponds to a loss of 0.07 mol of 1,4-dioxane; (B) DSC of embodiment 8 showing an endotherm of 58.6 J/g at 199.7° C. due to sample melt.

Figure 21A:
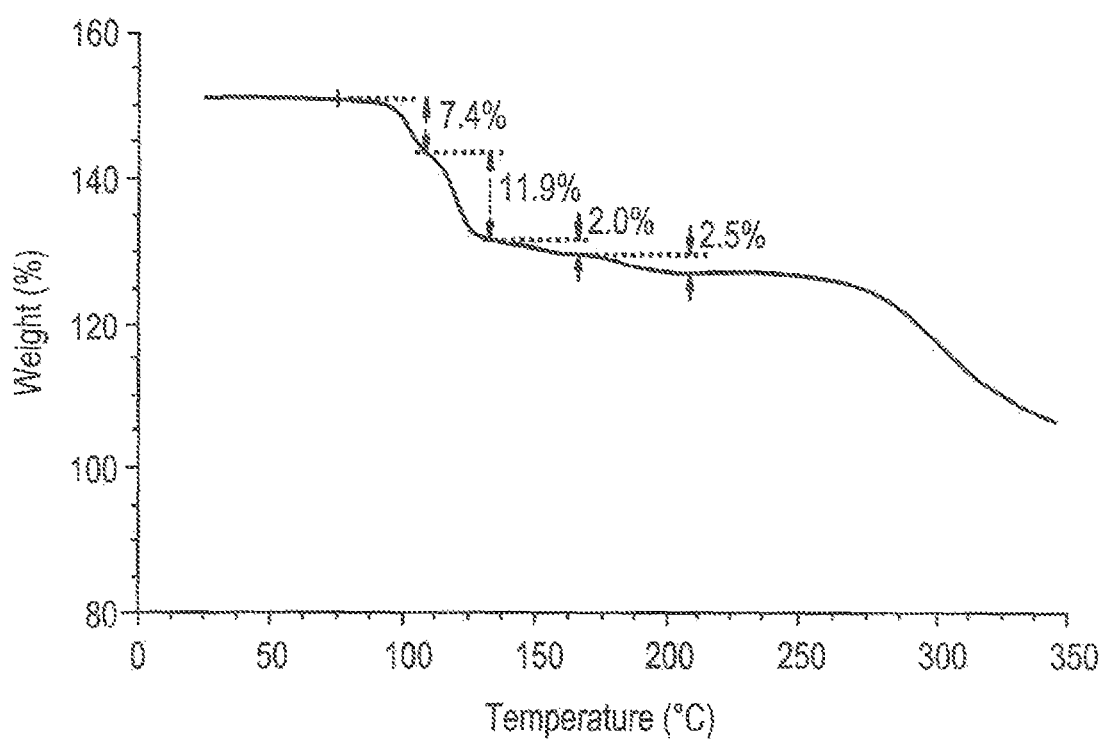
Figure 21B:
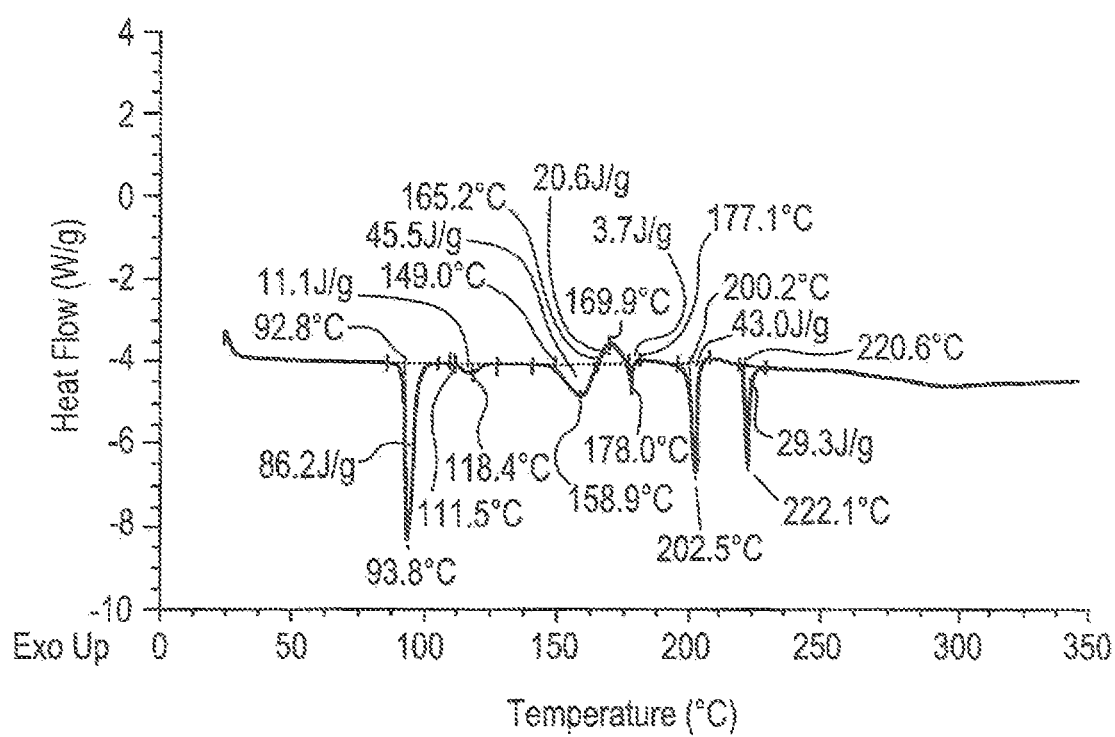

FIGS. 21A-B. (A) TGA of embodiment 2 showing a 7.4% w/w loss between 75° C. and 110° C., a 11.9% w/w loss between 110° C. and 130° C., a 2.0% w/w loss between 130° C. and 165° C., and a 2.5% w/w loss between 165° C. and 210° C.; (B) DSC of embodiment 2 showing an endotherm of 86.2 J/g at 92.8° C., an endotherm of 11.1 J/g at 111.5° C., an endotherm of 45.5 J/g at 149.0° C., an exotherm of 20.6 J/g at 165.2° C., an endotherm of 3.7 J/g at 177.1° C., an endotherm of 43.0 J/g at 200.2° C., and an endotherm of 29.3 J/g at 220.6° C.

Figure 22A:
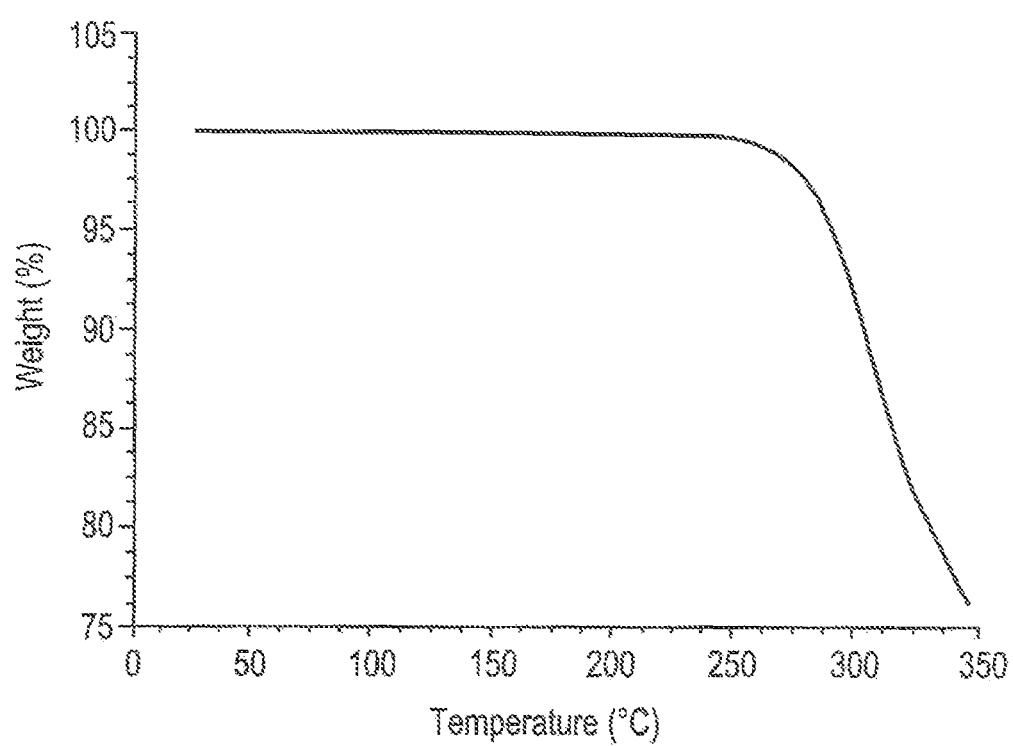
Figure 22B:
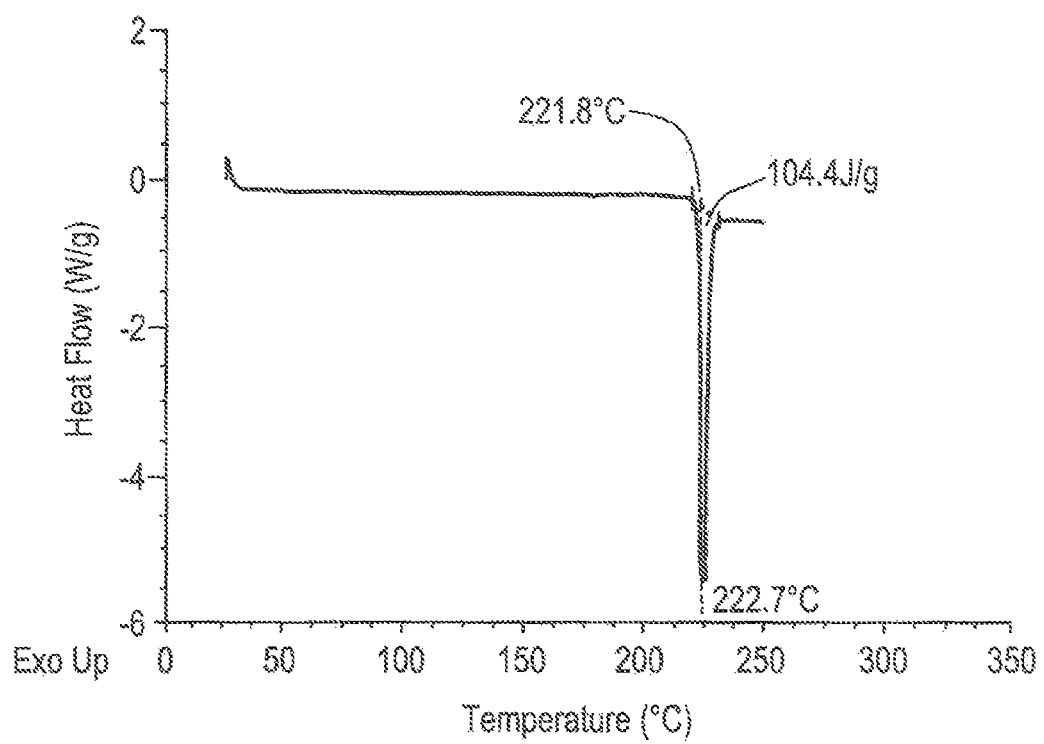

FIGS. 22A-B. (A) TGA of embodiment 9; (B) DSC of embodiment 9 showing an endotherm of 104.4 J/g at 221.8° C.

Figure 23A:
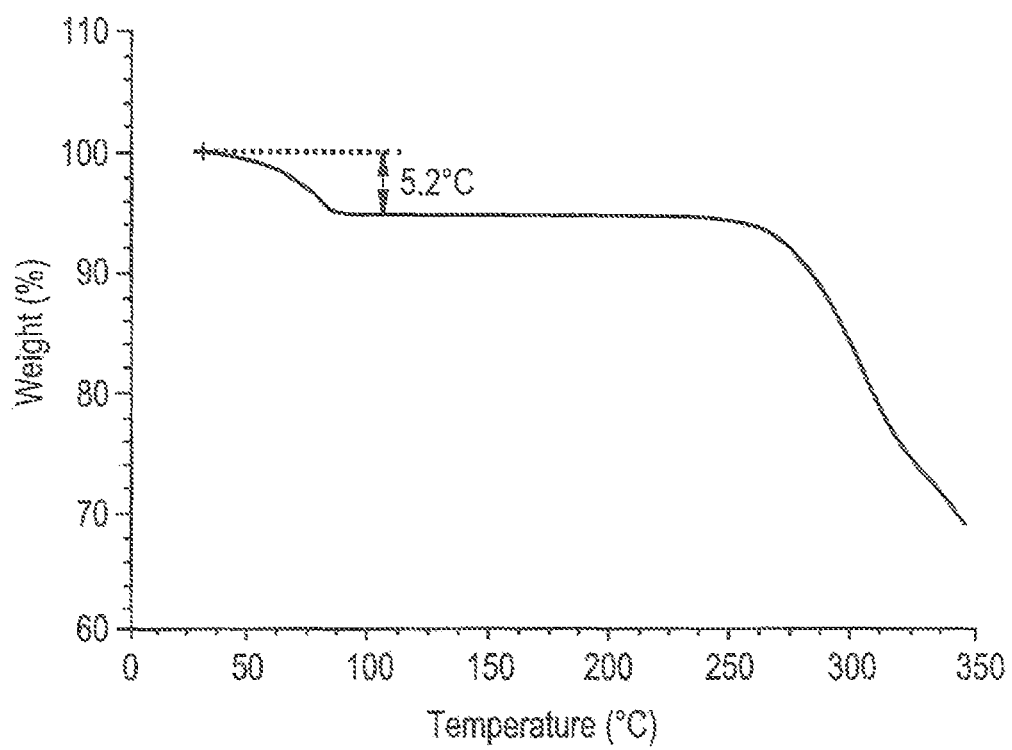
Figure 23B:
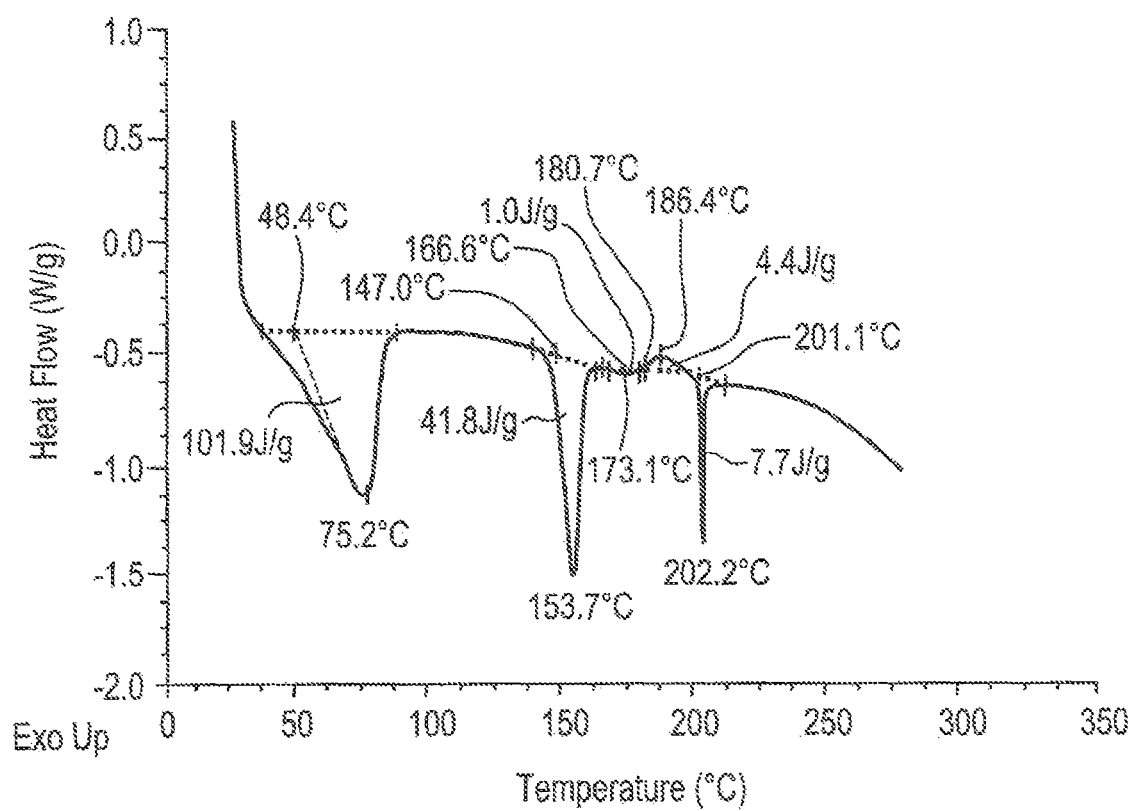

FIGS. 23A-B. (A) TGA of embodiment 16 showing a 5.2% w/w loss between 30° C. and 105° C.; (B) DSC of embodiment 16 showing an endotherm of 48.4 J/g between 35° C. and 90° C., an endotherm of 41.8 J/g at 147.0° C., an endotherm of 1.0 J/g at 166.6° C., an exotherm of 4.4 J/g at 180.7° C., and an endotherm of 7.7 J/g at 201.1° C.

Figure 24:
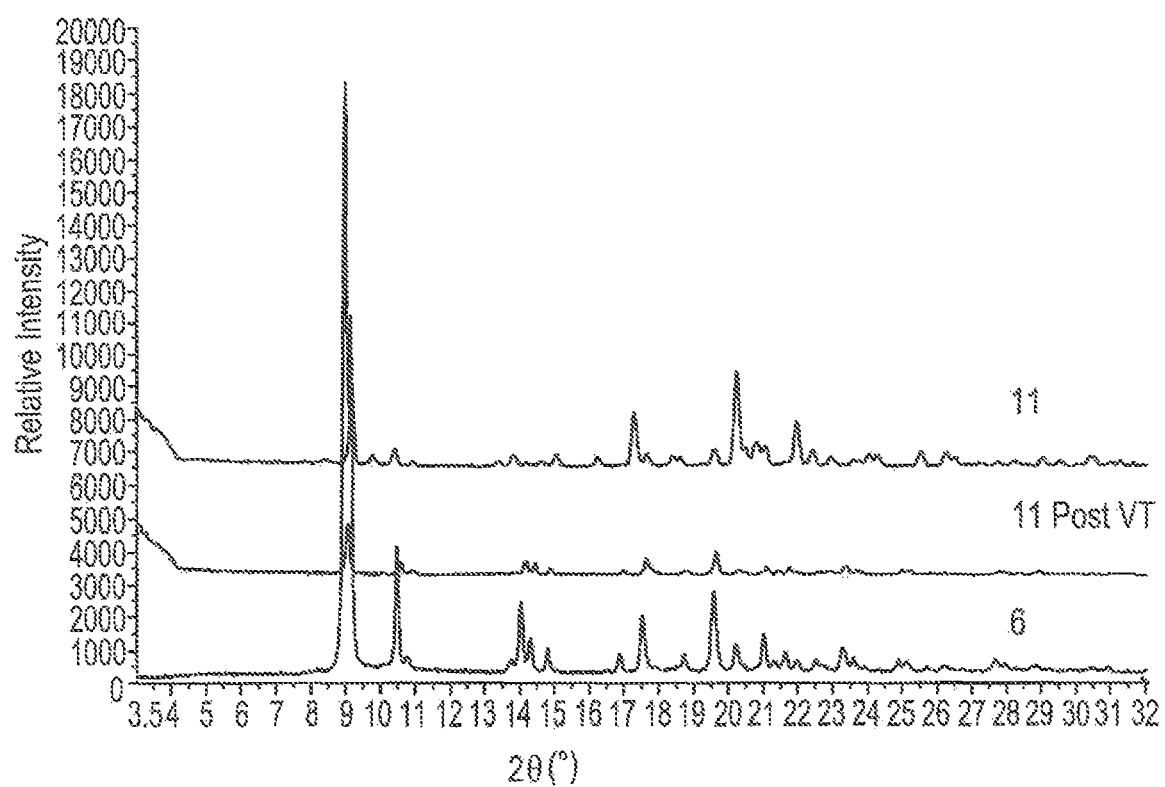

FIG. 24. X-ray powder diffraction (XRPD) of embodiment 11 (labeled "11") and X-ray powder diffraction (XRPD) of embodiment 11 after the variable temperature (VT)-XRPD experiment (labeled "11 post VT"), and X-ray powder diffraction (XRPD) of embodiment 6.

Figure 25:
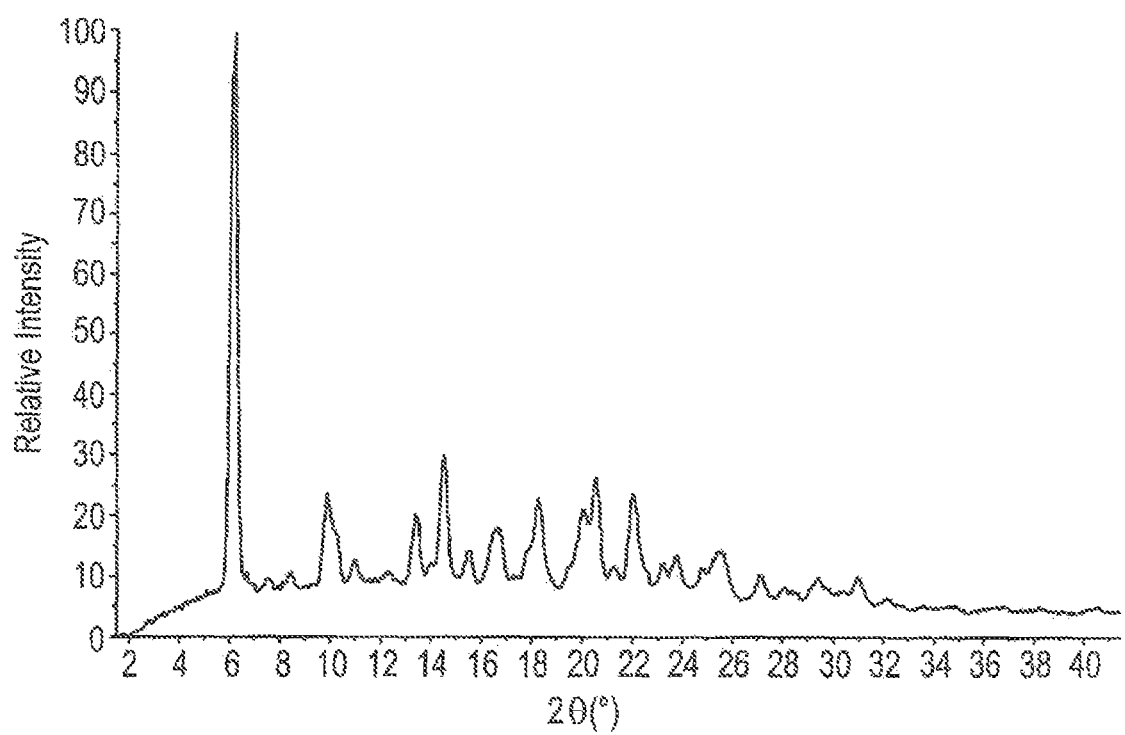

FIG. 25. X-ray powder diffraction (XRPD) pattern for compound of Formula I in form 1s.

DETAILED DESCRIPTION OF THE INVENTION

As used herein, the terms "including", "containing" and "comprising" are used in their open, non-limiting sense.

Any formula given herein is intended to represent compounds having structures depicted by the structural formula as well as certain variations or forms. Certain structures may exist as tautomers. Additionally, an amorphous form, hydrates, solvates, polymorphs and pseudopolymorphs of such compounds of this invention, and mixtures thereof, are also envisaged as parts of this invention. Aspects of this invention are in a solvent-free form or in any one of hydrated and/or solvated forms as illustrated herein.

The term "about" as used herein when immediately preceding a numerical value means a range of plus or minus 10% of that value, for example, "about 50" means 45 to 55, "about 25,000" means 22,500 to 27,500, etc., unless the context of the disclosure indicates otherwise, or is inconsistent with such an interpretation.

The term "administer" or "administered" or "administering" refers to the administration of compound of Formula I or a pharmaceutical composition thereof to a subject by any method known to those skilled in the art in view of the present disclosure, such as by intramuscular, subcutaneous, oral, intravenous, cutaneous, intramucosal (e.g., gut), intranasal or intraperitoneal route of administration. In particular aspects, a pharmaceutical composition of the invention is administered to a subject orally.

The term "subject" means any animal, particularly a mammal, most particularly a human, who will be or has been treated by a method according to an embodiment of the invention. The term "mammal" as used herein, encompasses any mammal. Examples of mammals include, but are not limited to, cows, horses, sheep, pigs, cats, dogs, mice, rats, rabbits, guinea pigs, non-human primates (NHPs) such as monkeys or apes, humans, etc., more particularly a human.

The term "inhibitors" or "inhibitor" refers to compounds that decrease, prevent, inactivate, desensitize or down-regulate JAK expression or activity.

The term "therapeutically effective amount" refers to an amount of an active compound or pharmaceutical agent, including a crystalline form of the present invention, which elicits the biological or medicinal response in a tissue system, animal or human that is being sought by a researcher, veterinarian, medical doctor or other clinician, including reduction or inhibition of an enzyme or a protein activity, or ameliorating symptoms, alleviating conditions, slowing or delaying disease progression, or preventing a disease.

As used herein, the term "treat", "treating", or "treatment" of any disease, condition, syndrome, or disorder refers, in one embodiment, to ameliorating the disease, condition, syndrome or disorder (i.e. slowing or arresting or reducing the development of the disease or at least one of the clinical symptoms thereof). In another embodiment, "treat", "treating", or "treatment" refers to alleviating or ameliorating at least one physical parameter including those which may not be discernible by the patient. In a further embodiment, "treat", "treating", or "treatment" refers to modulating the disease, condition, syndrome, or disorder either physically (e.g. stabilization of a discernible symptom), physiologically, (e.g. stabilization of a physical parameter), or both. In yet another embodiment, "treat", "treating", or "treatment" refers to preventing or delaying the onset or development or progression of the disease, condition, syndrome, or disorder.

A "pharmaceutically acceptable salt" is a salt of a compound that is non-toxic, biologically tolerable, or otherwise biologically suitable for administration to the subject. See, generally, S.M. Berge, et al., "Pharmaceutical Salts", J. Pharm. Sci. 66, 1-19 (1977), and Handbook of Pharmaceutical Salts, Properties, Selection, and Use, Stahl and Wermuth, Eds., Wiley-VCH and VHCA, Zurich, 2002. Compound of Formula I may possess a sufficiently acidic group, a sufficiently basic group, or both types of functional groups, and accordingly react with a number of inorganic or organic bases, and inorganic and organic acids, to form a pharmaceutically acceptable salt. Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

Disclosed herein are compositions of compound of Formula I and methods for using them in the treatment of disease states, disorders, and conditions mediated by one or more of the JAK family of tyrosine kinases. In some aspects, the method comprises administering to the subject a composition comprising an effective amount of compound 2-(1-((1r,4r)-4-(Cyanomethyl)cyclohexyl)-1,6-dihydroimidazo

[4,5-d]pyrrolo[2,3-b]pyridin-2-yl)-N-(2-hydroxy-2-methylpropyl)acetamide, having the structure of Formula I:

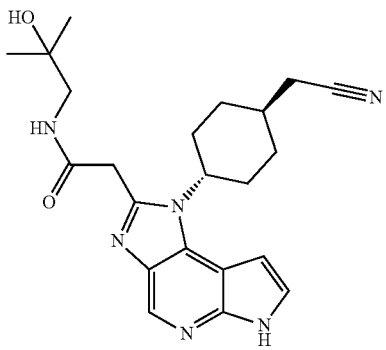

or a pharmaceutically acceptable salt, solvate and polymorph thereof.

Also disclosed herein are methods of treating or preventing a subject suffering from stomacho-intestinal system cancer or colorectal cancer. The method comprises administering to the subject a composition comprising a therapeutically effective amount of compound of Formula I or a pharmaceutically acceptable salt, solvate and polymorph thereof. The stomach, small intestine, and large intestine (the latter including the colon, rectum and anus) are here collectively referred to as the stomacho-intestinal system ("SIS") and cancer in any of such organs is referred to as stomacho-intestinal system cancer ("SISC"). Cancer in any of the colon and rectum is referred to as colorectal cancer ("CRC").

Also disclosed herein are methods of treating or preventing pre-malignant conditions in a subject comprising administering to the subject a composition comprising a therapeutically effective amount of compound of Formula I or a pharmaceutically acceptable salt, solvate and polymorph thereof. Pre-malignant conditions that precede SISC can be present in any one of a plurality of regions of the gastrointestinal tract, and in particular of the colon and/or rectum. Sometimes such conditions are manifested in the form of polyps that can be present in small numbers, as in the sporadic onset of the same, in large numbers, as in familial adenomatous polyposis ("FAP"), or not be present at all, as in certain forms of hereditary non-polyposis colorectal cancer, also known as Lynch Syndrome.

Also disclosed herein are methods of treating, delaying or preventing any manifestation of disease in a subject suffering from any SISC-related cancer predisposition syndrome, such as familial adenomatous polyposis ("FAP"). The method includes delaying the need for surgical procedures such as colectomy, which prophylactically removes the colon in order to lower the risk of future colorectal cancer development. The method comprises administering to the subject a composition comprising a therapeutically effective amount of compound of Formula I or a pharmaceutically acceptable salt thereof, solvate and polymorph thereof. The term FAP is used herein to encompass what is sometimes referred to as subtypes of the same, such as attenuated familial adenomatous polyposis ("AFAP"). Unless indicated otherwise or referred to expressly as any specific subtype, the term FAP includes subtypes such as AFAP.

In some aspects, a method of reducing the number of polyps or polyp burden (the latter defined by considering both the numbers and individual sizes of polyps) in a subject comprises administering to the subject a composition comprising a therapeutically effective amount of compound of Formula I or a pharmaceutically acceptable salt, solvate and polymorph thereof. In some aspects, reducing the number of polyps comprises reducing the number of polyps in the colon, rectum, post-surgical J-pouch and/or duodenum after administration of compound of Formula I. In some aspects, the number of polyps that are ≥2 mm in diameter in the colon, rectal, post-surgical J-pouch and duodenum are reduced. In some aspects, number of polyps that are ≥5 mm in diameter in the colon, rectal, post-surgical J-pouch and/or duodenum are reduced. In certain aspects, the decrease in the number of polyps after administration is by about 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.9% or more, or any range(s) in between.

Also disclosed herein are methods of treating or preventing the onset of SISC at any stage of disease evolution, and especially the onset of CRC, comprising administering to the subject a composition comprising a therapeutically effective amount of compound of Formula I or a pharmaceutically acceptable salt, solvate and polymorph thereof.

Also disclosed herein are methods of treating or preventing any chronic or acute inflammation disorder in the stomacho-intestinal system in a subject, comprising administering to the subject a composition comprising a therapeutically effective amount of compound of Formula I or a pharmaceutically acceptable salt, solvate and polymorph thereof.

Additional aspects of this invention relate to the use of compound of Formula I for administration to a subject who has or has had at least one of sporadic stomacho-intestinal polyp formation, FAP (or other inherited polyposis syndromes) and Lynch Syndrome (or other inherited nonpolyposis syndromes).

Additional aspects of the invention are methods of treating a subject suffering from or diagnosed with at least one form of localized or metastatic SISC, including at least one of gastric, small intestine, colorectal and anus cancer by administering a composition comprising a therapeutically effective amount of compound of Formula I or a pharmaceutically acceptable salt, solvate and polymorph thereof.

Additional aspects of the invention include a method of SISC interception in a subject comprising administering a composition comprising a therapeutically effective amount of compound of Formula I or a pharmaceutically acceptable salt, solvate and polymorph thereof. Further aspects are given by any one of the foregoing in which SISC interception is FAP SISC interception. Further aspects are given by any one of the foregoing aspects in which SISC interception is Lynch syndrome SISC interception. Further aspects are given by any one of the foregoing aspects in which SISC interception is sporadic polyp interception. Further aspects are given by any one of the foregoing aspects in which SISC interception is gastric cancer interception. Further aspects are given by any one of the foregoing aspects in which SISC interception is small intestine cancer interception. Further aspects are given by any one of the foregoing aspects in which SISC interception is anus cancer interception.

In some SISC interception scenarios, a drug delivery along the entire or a large portion of the intestinal tract may be desirable. In other scenarios, it may be desirable to increase local concentration at any given portion of the gastrointestinal tract. Still in other scenarios, a combination of these two forms of delivery at different sites in the intestinal tract could be desirable.

A therapeutically effective dose of compound of Formula I includes a dose range from about 1 mg to about 1000 mg, 10 mg to about 1000 mg, or any particular amount or range therein, in particular, from about 1 mg to about 100 mg, 10 mg to about 100 mg, or any particular amount or range therein. In some aspects of this invention, the dose range is from about 1 mg to about 5 mg. In some aspects of this invention, the dose range is from about 5 mg to about 10 mg. In some aspects of this invention, the dose range is from about 10 mg to about 15 mg. In some aspects of this invention, the dose range is from about 15 mg to about 20 mg. In some aspects of this invention, the dose range is from about 20 mg to about 25 mg. In some aspects of this invention, the dose range is from about 25 mg to about 30 mg. In some aspects of this invention, the dose range is from about 35 mg to about 40 mg. In some aspects of this invention, the dose range is from about 45 mg to about 50 mg. In some aspects of this invention, the dose range is from about 55 mg to about 60 mg. In some aspects of this invention, the dose range is from about 65 mg to about 70 mg. In some aspects of this invention, the dose range is from about 75 mg to about 80 mg. In some aspects of this invention, the dose range is from about 85 mg to about 90 mg. In some aspects of this invention, the dose range is from about 95 mg to about 100 mg. In some aspects of this invention, the dose range is from about 30 mg to about 1620 mg. In some aspects of this invention, the dose range is from about 50 mg to about 90 mg. In some aspects of this invention, the dose range is from about 50 mg to about 80 mg. In some aspects of this invention, the dose is about 50 mg. In some aspects of this invention, the dose is about 55 mg. In some aspects of this invention, the dose is about 60 mg. In some aspects of this invention, the dose is about 65 mg. In some aspects of this invention, the dose is about 70 mg. In some aspects of this invention, the dose is about 75 mg. In some aspects of this invention, the dose is about 80 mg. In some aspects of this invention, the dose is about 85 mg. In some aspects of this invention, the dose is about 90 mg. In some aspects of this invention, the dose is about 95 mg. In some aspects of this invention, the dose is about 100 mg. In some aspects of this invention, each of the dosage is a daily dose. In some aspects of this invention, the dosage entails multiple administrations per day, such as twice daily or thrice daily. For example, a 100-mg administration is achieved by administering a dosage of 50 mg twice daily; a 130-mg administration is achieved by administering a dosage of 65 mg twice daily; a 150-mg administration is achieved by administering a dosage of 75 mg twice daily; a 200-mg administration is achieved by administering a dosage of 100 mg twice daily; a 300-mg administration is achieved by administering a dosage of 150 mg twice daily; a 400-mg administration is achieved by administering a dosage of 200 mg twice daily; and a 600-mg administration is achieved by administering a dosage of 300 mg twice daily.

In some aspects, the compound of Formula I is in a crystalline form selected from forms 1s, 1a, 1b, 1c, 1d, 1e, 1f, 1g, 1h, 2, 3b, 3c, 3d, 3e, 5, 6, 7, 8, 9, 10, 11, 11b, 12, 15, 16, 17, 18, 19, 20, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52 and 53.

In some aspects, a method of treating or preventing a subject from suffering from familial adenomatous polyposis ("FAP") comprises administering to the subject a therapeutically effective dose of about 1 mg to about 100 mg of compound of Formula I. In some aspects, the administration is once daily or twice daily. In some aspects, treating FAP comprises reducing the polyp burden in said subject. In some aspects, reducing polyp burden comprises decrease in the number of polyps and/or a decrease in the size of polyps.

In some aspects, a method of treating or preventing FAP in a subject who has previously received a therapy or is currently receiving a therapy for FAP comprises administering to the subject a therapeutically effective dose of about 1 mg to about 100 mg of compound of Formula I. In some aspects, the therapy may be surgery, radiation therapy, Cox-2 inhibitors, non-steroidal anti-inflammatory drugs (NSAIDs), or chemotherapy.

In some aspects, a method of treating or preventing a subject from suffering from SISC comprises administering to the subject a therapeutically effective dose of about 1 mg to about 100 mg of compound of Formula I. In some aspects, the administration is once daily or twice daily. In some aspects, treating or preventing SISC comprises reducing the polyp burden in said subject. In some aspects, reducing polyp burden comprises decrease in the number of polyps and/or a decrease in the size of polyps.

In some aspects, a method of treating or preventing SISC in a subject who has previously received a therapy or is currently receiving a therapy comprises administering to the subject a therapeutically effective dose of about 1 mg to about 100 mg of compound of Formula I. In some aspects, the therapy may be surgery, radiation therapy, chemotherapy. EGFR inhibitors, VEGF inhibitors, and checkpoint inhibitors.

In some aspects, a method of treating or preventing CRC in a subject who has previously received a therapy or is currently receiving a therapy comprises administering to the subject a therapeutically effective dose of about 1 mg to about 100 mg of compound of Formula I. In some aspects, the therapy may be surgery, radiation therapy, chemotherapy. EGFR inhibitors, VEGF inhibitors, and checkpoint inhibitors.

In some aspects, a method of treating or preventing a subject from suffering from CRC comprises administering to the subject a therapeutically effective dose of about 1 mg to about 100 mg of compound of Formula I. In some aspects, the administration is once daily or twice daily. In some aspects, treating or preventing CRC comprises reducing the CRC malignancy and/or associated polyp burden in said subject. In some aspects, reducing polyp burden comprises decrease in the number of polyps and a decrease in the size of polyps. In some aspects, reducing polyp parameters comprises decrease in the number of polyps or a decrease in the size of the polyps.

In some aspects, a method of preventing a relapse of CRC in a subject comprises administering to the subject a therapeutically effective dose of about 1 mg to about 100 mg of compound of Formula I.

In some aspects, a method of preventing a relapse of FAP-related polyposis in a subject comprises administering to the subject a therapeutically effective dose of about 1 mg to about 100 mg of compound of Formula I.

In some aspects, a method of preventing symptomatic progression of FAP in a subject comprises administering to the subject a therapeutically effective dose of about 1 mg to about 100 mg of compound of Formula I.

In some aspects, a method of delaying symptomatic progression of FAP in a subject comprises administering to the subject a therapeutically effective dose of about 1 mg to about 100 mg of compound of Formula I.

In some aspects, a method of preventing SISC in a subject who has been diagnosed with irritable bowel disease (IBD)

comprises administering to the subject a therapeutically effective dose of about 1 mg to about 100 mg of compound of Formula I. In some aspects, IBD may be ulcerative colitis or Crohn's disease.

In some aspects, a method of preventing SISC in a subject who has previously been diagnosed for a cancer comprises administering to the subject a therapeutically effective dose of about 1 mg to about 100 mg of compound of Formula I. In some aspects, the cancer may be breast cancer, ovarian cancer, uterine cancer or abdominal cancer.

In some aspects, the compound of Formula I is administered as a preventive measure or as an interception to treat subjects who are at high risk of developing CRC, SISC, or FAP. The high risk may be due to factors, such as irritable bowel syndrome, presence of particular gut microbiome constituents, a family history of colorectal cancer, a prior history of colorectal cancer, a finding of a polyp or precancerous lesion during colonoscopy, or other genetic factors, such as mutations in the KRAS, TP53, EGFR, STK11 (LKB1), PTEN, BMPR1A, SMAD4 (MADH/DPC4), MLH1, MSH2, MSH6, PMS2, EPCAM, MUTYH (MYH), POLD1, POLE and/or APC genes.

In some aspects, a method of preventing FAP or CRC in a subject who is in the high-risk group comprises administering to the subject a therapeutically effective dose of about 1 mg to about 100 mg of compound of Formula I.

In some aspects, a method of preventing pre-malignant conditions from becoming malignant conditions comprises administering to the subject a therapeutically effective dose of about 1 mg to about 100 mg of compound of Formula I. In some aspects, the premalignant condition may be the presence of adenomatous polyps. In some aspects, the premalignant condition may be Lynch Syndrome. In some aspects, the premalignant condition may be early stage CRC and adenomas.

In some aspects, a method of treating an excessive inflammatory response in the intestinal tract comprises administering to the subject a therapeutically effective dose of about 1 mg to about 100 mg of compound of Formula I.

In some aspects, a method of treating or preventing a subject from suffering from colorectal cancer comprises administering to the subject a therapeutically effective dose of about 50 mg to about 100 mg of compound of Formula I (crystalline form 1s). In some aspects, the administration is once daily or twice daily.

In some aspects, a method of treating or preventing a subject from suffering from colorectal cancer comprises administering to the subject a therapeutically effective dose of about 10 mg to about 50 mg of compound of Formula I (crystalline form 1s). In some aspects, the administration is once daily or twice daily.

In some aspects, a method of treating or preventing a subject from suffering from colorectal cancer comprises administering to the subject a therapeutically effective dose of about 30 mg to about 50 mg of compound of Formula I (crystalline form 1s). In some aspects, the administration is once daily or twice daily.

In some aspects, a method of treating or preventing a subject from suffering from colorectal cancer comprises administering to the subject a therapeutically effective dose of about 50 mg to about 100 mg of compound of Formula I (crystalline form 11). In some aspects, the administration is once daily or twice daily.

In some aspects, a method of treating a disorder or condition that is affected by the inhibition of JAK tyrosine kinase activity in a subject in need of treatment, comprising administering compound of Formula I or a pharmaceutically acceptable salt, solvate or polymorph thereof in an amount sufficient to achieve a concentration in the colon tissue from about 20 ng/g to about 20,000 ng/g. In some aspects, the administration achieves a tissue concentration from about 20 ng/g to about 15,000 ng/g, about 20 ng/g to about 10,000 ng/g, about 20 ng/g to about 8,000 ng/g, about 20 ng/g to about 6,000 ng/g, about 20 ng/g to about 4,000 ng/g, or about 20 ng/g to about 1,000 ng/g. In some aspects, the disorder or condition is colorectal cancer or FAP.

In some aspects, a method of treating a disorder or condition that is affected by the inhibition of JAK in a subject in need of treatment, comprising administering compound of Formula I or a pharmaceutically acceptable salt, solvate or polymorph thereof in an amount sufficient to achieve a concentration in the rectum tissue from about 20 ng/g to about 20,000 ng/g. In some aspects, the administration achieves a tissue concentration from about 20 ng/g to about 15,000 ng/g, about 20 ng/g to about 10,000 ng/g, about 20 ng/g to about 8,000 ng/g, about 20 ng/g to about 6,000 ng/g, about 20 ng/g to about 4,000 ng/g, or about 20 ng/g to about 1,000 ng/g. In some aspects, the disorder or condition is colorectal cancer or FAP.

Also disclosed herein are methods to determine or predict a response to a JAK inhibitor in a subject in need of a treatment. In one aspect, a method of predicting a response to compound of Formula I in a subject in need thereof comprising:
  (a) measuring level of pSTAT-3 in a subject's control sample that has not been exposed to compound of Formula I;
  (b) measuring a level of pSTAT-3 in a subject's test sample that has been exposed to compound of Formula; and
  (c) comparing the level of pSTAT-3 in (a) to (b), wherein a decrease in the level of pSTAT-3 in (b) is predictive of a response to the compound of Formula I in the subject.

In another aspect, a method of monitoring an efficacy of an ongoing JAK inhibitor therapy in a subject in need thereof comprising:
  (a) measuring level of pSTAT-3 in a subject's control sample that has not been exposed to compound of Formula I;
  (b) measuring a level of pSTAT-3 in a subject's test sample that has been exposed to compound of Formula; and
  (c) comparing the level of pSTAT-3 in (a) to (b), wherein a decrease in the level of pSTAT-3 in (b) is indicative of efficacy of compound of Formula I in the subject.

In another aspect, a method of designing a drug regimen to treat familial adenomatous polyposis, cancer or a JAK mediated disease in a subject in need thereof comprising:
  (a) measuring level of pSTAT-3 in a subject's control sample that has not been exposed to compound of Formula I;
  (b) measuring a level of pSTAT-3 in a subject's test sample that has been exposed to compound of Formula; and
  (c) comparing the level of pSTAT-3 in (a) to (b), and
  (d) administering a higher dose of compound of Formula I if the level of pSTAT-3 in higher in the test sample when compared to the control sample.

A method of modifying the dose and/or frequency of dosing of a JAK inhibitor in a subject suffering from FAP, cancer or a JAK mediated disease comprising:

(a) measuring level of pSTAT-3 in a subject's control sample that has not been exposed to compound of Formula I;
(b) measuring a level of pSTAT-3 in a subject's test sample that has been exposed to compound of Formula; and
(c) comparing the level of pSTAT-3 in (a) to (b), and
(d) increasing the dose of compound of Formula I if the level of pSTAT-3 in higher, equal or marginally decreased in the test sample when compared to the control sample, and decreasing the dose of compound of Formula I if the level of pSTAT-3 in lower in the test sample when compared to the control sample.

In some aspects, the test sample and the control sample are from the same subject. In some aspects, the control sample may be from the subject prior to administration of compound of Formula I. In some aspects, the control sample may be from the pool of subject samples prior to administration of compound of Formula I to the subjects.

In some aspects, the subject's sample (control or test sample) may be any cell or tissue, including blood. In some aspects, the subject's sample may be a normal cell, a normal tissue, a tumor cell, a tumor tissue, or any malignant cell. In some aspects, the subject's sample may be tissue from different sites of intestinal tract, such as colon, rectal, post-surgical J-pouch and duodenum.

Once a subject's control sample or a test sample is obtained, the level of pSTAT-3 in the subject's sample can be measured using assays, such as flow cytometry, preferably imaging flow cytometry (IFC), luminescent analysis, chemiluminescent analysis, immunohistochemistry, fluorescent microscopy, and the like.

In some aspects, comparing the level of pSTAT-3 in the control sample and the test sample may provide information about JAK inhibitor efficacy in a subject. For example, a decrease in pSTAT-3 level the test sample when compared to the control sample may indicate that the compound of Formula I is effective in a subject. In certain aspects, the decrease in pSTAT-3 level in the test sample when compared to the control sample is by about 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.9% or more, or any range(s) in between.

In some aspects, a method of treating CRC or FAP in a subject comprises: (a) determining a mutation in one or more genes selected from KRAS, TP53, EGFR, STK11 (LKB1), PTEN, BMPR1A, SMAD4 (MADH/DPC4), MLH1, MSH2, MSH6, PMS2, EPCAM, MUTYH (MYH), POLD1, POLE and APC; and (b) administering a therapeutically effective dose of compound of Formula I.

In some aspects, a method of diagnosing whether the subject has a high risk of developing CRC or FAP in a subject comprises: (a) determining a mutation in one or more genes selected from KRAS, TP53, EGFR, STK11 (LKB1), PTEN, BMPR1A, SMAD4 (MADH/DPC4), MLH1, MSH2, MSH6, PMS2, EPCAM, MUTYH (MYH), POLD1, POLE and APC; and (b) administering a therapeutically effective dose of compound of Formula I.

In some aspects, compound of Formula I administration exhibits pan-JAK kinase inhibition effects with local GI effects and low or negligible systemic effects, as defined by changes in pSTAT-3 levels in the circulation. Furthermore, aspects of this invention with such features can be orally administered. In some aspects, the compound of Formula I may be used for the prevention and/or control of excessive inflammatory response and whose systemic effects are eliminated or reduced. In some aspects, the compound of Formula I exhibits local effects on gastro-intestinal tissues for the treatment of conditions such as, but not limited to, IBD, without causing systemic effects or with such systemic effects acceptably reduced.

Once improvement of the patient's disease, disorder, or condition has occurred, the dose may be adjusted for preventive or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the compound of Formula I is envisaged for use alone, in combination with one or more of other active agents, or in combination with additional active ingredients in the treatment of the conditions discussed herein. Non-limiting examples of active agents that can be combined with compound of Formula I include NSAIDs, Cox-2 inhibitors, anti-EGFR agents such as cetuximab and panitumumab, anti-VEGF/VEGFR agents, such as bevacizumab, Ziv-aflibercept, regorafenib, ramucirumab, and immune checkpoint inhibitors, such as ipilimumab, nivolumab, and pembrolizumab. The additional active ingredients may be coadministered separately along with one compound of Formula I, or included in a single pharmaceutical composition according to the invention. In an illustrative embodiment, additional active ingredients are those that are known or discovered to be effective in the treatment of conditions, disorders, or diseases mediated by JAK activity, such as another JAK inhibitor or a compound active against another target associated with the particular condition, disorder, or disease. The combination may serve to increase efficacy (e.g., by including in the combination a compound potentiating the potency or effectiveness of an active agent), decrease one or more side effects, or decrease the required dose of the active agent.

In some aspects, the compositions of compound of Formula I comprise pharmaceutically acceptable excipients. Pharmaceutically acceptable excipients commonly used in pharmaceutical compositions are substances that are non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of such excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of compound of Formula I may be prepared using pharmaceutically acceptable excipients and compounding techniques known or that become available to those of ordinary skill in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. The compositions may be formulated for any one of a plurality of administration routes, such as intravenous infusion, subcutaneous injection, topical administration, or oral administration. Preferably, the compositions may be formulated for oral administration.

For oral administration, active agents can be provided in the form of tablets, capsules, or beads, or as a solution, emulsion, or suspension. To prepare the oral compositions, the active agents may be formulated to yield a dosage of, e.g., for a 70-kg human, from about 1 to 1000 mg/day in single or multiple dosage units as an illustrative range.

Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating. Additional coating that may be used include coatings that are designed to release the compound or active agent as a function of time, pH or bacterial content.

Capsules for oral administration include hard and soft gelatin or (hydroxypropyl)methyl cellulose capsules. To prepare hard gelatin capsules, active ingredient(s) may be mixed with a solid, semi-solid, or liquid diluent. Soft gelatin capsules may be prepared by mixing the active ingredient with an oil such as peanut oil or olive oil, liquid paraffin, a mixture of mono and di-glycerides of short chain fatty acids, polyethylene glycol 400, or propylene glycol. Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The compositions of compound of Formula I may also be administered by non-oral routes. For example, the compositions may be formulated for rectal administration as a suppository. For parenteral use, including intravenous, intramuscular, intraperitoneal, or subcutaneous routes, the compounds of the disclosure may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 µg/kg/minute of compound, admixed with a pharmaceutical carrier over a period ranging from several minutes to several days.

All aspects described herein for methods for treating, are also applicable for use in treating.

All aspects described herein for methods for treating a disorder or condition, are also applicable for use in treating said disorder or condition.

All aspects described herein for use in treating a disorder or condition, are also applicable for methods for treating said disorder or condition.

All aspects described herein for methods for treating a disorder or condition, are also applicable for use in a method for treating said disorder or condition.

All aspects described herein for use in a method for treating a disorder or condition, are also applicable for methods for treating said disorder or condition.

The following specific examples are provided to further illustrate the invention and various aspects.

In obtaining the compounds described in the examples below and the corresponding analytical data, the following experimental and analytical protocols were followed unless otherwise indicated.

Unless otherwise stated, reaction mixtures were magnetically stirred at room temperature (rt). Where solutions are "dried," they are generally dried over a drying agent such as $Na_2SO_4$ or $MgSO_4$. Where mixtures, solutions, and extracts were "concentrated", they were typically concentrated on a rotary evaporator under reduced pressure.

Thin-layer chromatography was performed using Merck silica gel 60 $F_{254}$ 2.5 cm×7.5 cm, 250 µm or 5.0 cm×10.0 cm, 250 µm pre-coated silica gel plates.

Normal-phase flash column chromatography (FCC) was performed on silica gel ($SiO_2$) eluting with 2 M $NH_3$ in MeOH/DCM, unless otherwise noted.

Mass spectra (MS) were obtained on an Agilent series 1100 MSD using electrospray ionization (ESI) in positive mode unless otherwise indicated. Calculated (calcd.) mass corresponds to the exact mass.

Nuclear magnetic resonance (NMR) spectra were obtained on Bruker model DRX spectrometers. The format of the $^1H$ NMR data below is: chemical shift in ppm downfield of the tetramethylsilane reference (multiplicity, coupling constant J in Hz, integration).

Chemical names were generated by either ChemDraw (CambridgeSoft, Cambridge, MA) or ACD/Name Version 9 (Advanced Chemistry Development, Toronto, Ontario, Canada). By way of example, the designation (1r,4r) refers to the trans orientation around the cyclohexyl ring as generated using the naming function of Chemdraw Ultra Pro 14.0.

Whenever a yield is given as a percentage, such yield refers to a mass of the entity for which the yield is given with respect to the maximum amount of the same entity that could be obtained under the particular stoichiometric conditions. Reagent concentrations that are given as percentages refer to mass ratios, unless indicated differently.

Abbreviations and acronyms used herein include the following as shown below:

Abbreviations and Acronyms Defined

| Acronym | Term |
| --- | --- |
| AAC | Accelerated aging conditions (40° C. and 70% RH) |
| ACN | Acetonitrile |
| aq | Aqueous |
| br | Broad |
| cLogP | Calculated logP |
| DCM | Dichloromethane |
| DIPEA, DIEA, or Hunig's base | Diisopropylethylamine |

| Acronym | Term |
| --- | --- |
| DMA | Dimethylacetamide |
| DMF | N,N-Dimethylformamide |
| DMPU | 1,3-Dimethyl-3,4,5,6-tetrahydro-2(1H)-pyrimidinone |
| DMSO | Dimethyl sulfoxide |
| EtOAc, or EA | Ethyl Acetate |
| EtOH | Ethanol |
| ESI | Electrospray ionization |
| FCC | Normal-phase silica gel flash column chromatography |
| g | Gram(s) |
| h | Hour(s) |
| HPLC | High-pressure liquid chromatography |
| HR-XRPD | High resolution X-ray powder diffraction |
| HT-XRPD | High throughput X-ray powder diffraction |
| IPA | isopropanol |
| i.c. | Intra-colonic |
| Hz | Hertz |
| LCMS | Liquid chromatography and mass spectrometry |
| M | Molar |
| m/z | Mass to charge ratio |
| MeOH | Methanol |
| mg | Milligram(s) |
| min | Minute(s) |
| mL | Milliliter(s) |
| μL | Microliter(s) |
| mmol | Millimole(s) |
| MTBE | Methyl tert-butyl ether |
| MS | Mass spectrometry |
| NMR | Nuclear magnetic resonance |
| p.o. | per os or by mouth |
| ppm | Parts per million |
| PTFE | polytetrafluoroethylene |
| PyBOP | Benzotriazol-1-yl-oxytripyrrolidinophosphonium hexafluorophosphate |
| PyBrOP | Bromotripyrrolidinophosphonium hexafluorophosphate |
| RH | Relative humidity |
| $R_t$ | Retention time |
| Rt or RT | Room temperature |
| TFA | Trifluoroacetic acid |
| THF | Tetrahydrofuran |
| TLC | Thin layer chromatography |
| tPSA | Topological polar surface area |

EXAMPLE 1

2-(1-((1r,4r)-4-(Cyanomethyl)cyclohexyl)-1,6-dihydroimidazo[4,5-d]pyrrolo[2,3-b]pyridin-2-yl)-N-(2-hydroxy-2-methylpropyl)acetamide

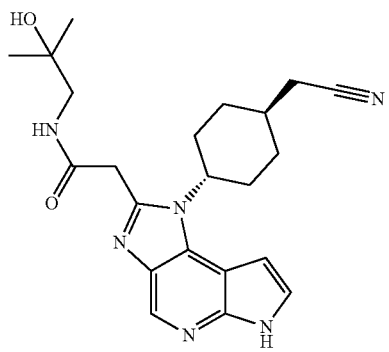

(Formula I)

Step A: 2-(1-((1r,4r)-4-(Cyanomethyl)cyclohexyl)-6-(phenylsulfonyl)-1,6-dihydroimidazo[4,5-d]pyrrolo[2,3-b]pyridin-2-yl)-N-(2-hydroxy-2-methylpropyl)acetamide. To ensure dry starting material, ethyl 2-(1-((1r,4r)-4-(cyanomethyl)cyclohexyl)-6-(phenylsulfonyl)-1,6-dihydroimidazo[4,5-d]pyrrolo[2,3-b]pyridin-2-yl)acetate (Intermediate 3) was heated under vacuum at 50° C. for 18 h prior to the reaction. In a 1 L flask, ethyl 2-(1-((1r,4r)-4-(cyanomethyl)cyclohexyl)-6-(phenylsulfonyl)-1,6-dihydroimidazo[4,5-d]pyrrolo[2,3-b]pyridin-2-yl)acetate (Intermediate 3, 52.585 g, 104.01 mmol) was suspended in DMA (50 mL). 1-Amino-2-methylpropan-2-ol (50 mL) was added and the reaction was heated to 110° C. for 45 minutes, then to 125° C. for 5 hours. The reaction was cooled to room temperature and diluted with EtOAc (800 mL). The organic layer was extracted three times with a solution of water/brine wherein the solution was made up of 1 L water plus 50 mL brine. The aqueous layers were back extracted with EtOAc (2×600 mL). The combined organic layers were dried over anhydrous $MgSO_4$, concentrated to dryness, and then dried for 3 days under vacuum to provide the title compound (65.9 g, 98% yield) as a yellow foam. The product was taken to the next step with no further purification. MS (ESI): mass calcd. for $C_{28}H_{32}N_6O_4S$, 548.22; m/z found, 549.2 $[M+H]^+$. $^1H$ NMR (400 MHz, $CDCl_3$): δ 8.76 (s, 1H), 8.26-8.19 (m, 2H), 7.84 (d, J=4.1 Hz, 1H), 7.60-7.53 (m, 1H), 7.50-7.44 (m, 2H), 6.84 (d, J=4.2 Hz, 1H), 4.76-4.61 (m, 1H), 3.97 (s, 2H), 3.45 (s, 1H), 3.27 (d, J=5.9 Hz, 2H), 2.41 (d, J=6.5 Hz, 2H), 2.38-2.25 (m, 2H), 2.23-2.12 (m, 2H), 2.09-1.94 (m, 4H), 1.48 (qd, J=13.6, 4.0 Hz, 2H), 1.21 (s, 6H).

Step B: 2-(1-((1r,4r)-4-(Cyanomethyl)cyclohexyl)-1,6-dihydroimidazo[4,5-d]pyrrolo[2,3-b]pyridin-2-yl)-N-(2-hydroxy-2-methylpropyl)acetamide. 2-(1-((1r,4r)-4-(Cyanomethyl)cyclohexyl)-6-(phenylsulfonyl)-1,6-dihydroimidazo[4,5-d]pyrrolo[2,3-b]pyridin-2-yl)-N-(2-hydroxy-2-methylpropyl)acetamide (65.90 g, 102.1 mmol) was added to a 1 L flask containing a stir bar. 1,4-dioxane (300 mL) was added, followed by aq KOH (3 M, 150 mL). The reaction was heated at 80° C. for 2 h. The reaction was cooled to room temperature and the solvent volume was reduced to about 200 mL on a rotovap. The residue was treated with a solution of water/brine (100 mL/100 mL), then extracted with 10% MeOH in $CH_2Cl_2$ (2×1 L). The organic layers were combined, dried over anhydrous $MgSO_4$, and concentrated to dryness to provide a yellow solid. The solid was suspended in $CH_2Cl_2$ (200 mL), stirred vigorously for 30 minutes, and then collected by filtration. The solid was rinsed with $CH_2Cl_2$ (100 mL), dried by pulling air through the filter, and then further dried under vacuum at room temperature for 16 h to provide the title compound (41.59 g, 89% yield) as a white solid. MS (ESI): mass calcd. for $C_{22}H_{28}N_6O_2$, 408.23; m/z found, 409.2 $[M+H]^+$. $^1H$ NMR (600 MHz, DMSO-$d_6$): δ 11.85 (s, 1H), 8.50 (s, 1H), 8.21-8.10 (m, 1H), 7.49-7.43 (m, 1H), 6.74-6.65 (m, 1H), 4.53-4.42 (m, 2H), 4.07 (s, 2H), 3.08 (d, J=6.0 Hz, 2H), 2.58 (d, J=6.1 Hz, 2H), 2.41-2.28 (m, 2H), 2.09-1.92 (m, 5H), 1.42-1.31 (m, 2H), 1.09 (s, 6H). The synthesis and active compound characterization of each of the aspects of this invention are provided herein in the form of examples. Due to the crystal structure of some of the aspects of this invention, polymorph screening may be pursued to further characterize specific forms of any such compound. This is illustrated in a non-limiting manner for compound of Formula I by the example under the heading polymorph screening.

The following compounds were prepared in reference to the foregoing synthesis:

Intermediate 1

2-((1r,4r)-4-((5-Nitro-1-(phenylsulfonyl)-1H-pyrrolo[2,3-b]pyridin-4-yl)amino)cyclohexyl)acetonitrile

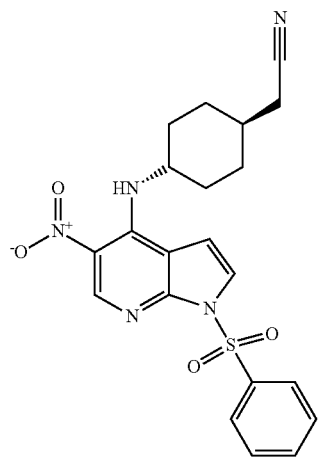

Step A: tert-butyl N-[(1r,4r)-4-(Hydroxymethyl)cyclohexyl]carbamate. To a 20-L 4-necked round-bottom flask purged and maintained with an inert atmosphere of nitrogen was placed (1r,4r)-4-[[(tert-butoxy)carbonyl]amino]cyclohexane-1-carboxylic acid (1066 g, 4.38 mol, 1.00 equiv) and THF (10 L). This was followed by the dropwise addition of $BH_3$-$Me_2S$ (10 M, 660 mL) at −10° C. over 1 h. The resulting solution was stirred for 3 h at 15° C. This reaction was performed three times in parallel and the reaction mixtures were combined. The reaction was then quenched by the addition of methanol (2 L). The resulting mixture was concentrated under vacuum. This resulted in of tert-butyl N-[(1r,4r)-4-(hydroxymethyl)cyclohexyl]carbamate (3000 g, 99.6%) as a white solid. MS (ESI): mass calcd. for $C_{12}H_{23}NO_3$, 229.32; m/z found, 215.2 [M-tBu+MeCN+H]$^+$; $^1$H NMR: (300 MHz, CDCl$_3$): δ 4.40 (s, 1H), 3.45 (d, J=6.3 Hz, 2H), 3.38 (s, 1H), 2.05-2.02 (m, 2H), 1.84-1.81 (m, 2H), 1.44 (s, 11H), 1.17-1.01 (m, 4H).

Step B: tert-butyl N-[(1r,4r)-4-[(Methanesulfonyloxy)methyl]cyclohexyl]carbamate. To a 20 L 4-necked round-bottom flask purged and maintained with an inert atmosphere of nitrogen, was placed tert-butyl N-[(1r,4r)-4-(hydroxymethyl)cyclohexyl]carbamate (1000 g, 4.36 mol, 1.00 equiv.), dichloromethane (10 L), pyridine (1380 g, 17.5 mol, 4.00 equiv.). This was followed by the dropwise addition of MsCl (1000 g, 8.73 mol, 2.00 equiv.) at −15° C. The resulting solution was stirred overnight at 25° C. This reaction was performed in parallel for 3 times and the reaction mixtures were combined. The reaction was then quenched by the addition of 2 L of water. The water phase was extracted with ethyl acetate (1×9 L). The organic layer was separated and washed with 1 M HCl (3×10 L), NaHCO$_3$ (saturated aq.) (2×10 L), water (1×10 L) and brine (1×10 L). The mixture was dried over anhydrous sodium sulfate, filtered and concentrated under vacuum. This resulted in of tert-butyl N-[(1r,4r)-4-[(methanesulfonyloxy)methyl]cyclohexyl]carbamate (3300 g, 82%) as a white solid. LC-MS: MS (ESI): mass calcd. for $C_{13}H_{25}NO_5S$, 307.15; m/z found 292.1, [M-tBu+MeCN+H]$^+$; $^1$H NMR: (300 MHz, CDCl$_3$): δ 4.03 (d, J=6.6 Hz, 2H), 3.38 (s, 1H), 3.00 (s, 3H), 2.07-2.05 (m, 2H), 1.87-1.84 (m, 2H), 1.72-1.69 (m, 1H), 1.44 (s, 9H), 1.19-1.04 (m, 4H).

Step C: tert-butyl N-[(1r,4r)-4-(Cyanomethyl)cyclohexyl]carbamate. To a 10 L 4-necked round-bottom flask, was placed tert-butyl N-[(1r,4r)-4-[(methanesulfonyloxy)methyl]cyclohexyl]carbamate (1100 g, 3.58 mol, 1.00 equiv.), DMSO (5500 mL) and NaCN (406 g, 8.29 mol, 2.30 equiv.). The resulting mixture was stirred for 5 h at 90° C. This reaction was performed in parallel 3 times and the reaction mixtures were combined. The reaction was then quenched by the addition of 15 L of water/ice. The solids were collected by filtration. The solids were washed with water (3×10 L). This resulted in tert-butyl N-[(1r,4r)-4-(cyanomethyl)cyclohexyl]carbamate (2480 g, 97%) as a white solid. MS (ESI): mass calcd. for $C_{13}H_{22}N_2O_2$, 238.17; m/z found 224 [M-tBu+MeCN+H]$^+$; $^1$H NMR: (300 MHz, CDCl3): δ 4.39 (s, 1H), 3.38 (s, 1H), 2.26 (d, J=6.9 Hz, 2H), 2.08-2.04 (m, 2H), 1.92-1.88 (m, 2H), 1.67-1.61 (m, 1H), 1.44 (s, 9H), 1.26-1.06 (m, 4H).

Step D: 2-[(1r,4r)-4-Aminocyclohexyl]acetonitrile hydrochloride. To a 10-L round-bottom flask was placed tert-butyl N-[(1r,4r)-4-(cyanomethyl)cyclohexyl]carbamate (620 g, 2.60 mol, 1.00 equiv.), and 1,4-dioxane (2 L). This was followed by the addition of a solution of HCl in 1,4-dioxane (5 L, 4 M) dropwise with stirring at 10° C. The resulting solution was stirred overnight at 25° C. This reaction was performed for 4 times and the reaction mixtures were combined. The solids were collected by filtration. The solids were washed with 1,4-dioxane (3×3 L), ethyl acetate (3×3 L) and hexane (3×3 L). This resulted in 2-[(1r,4r)-4-aminocyclohexyl]acetonitrile hydrochloride (1753 g, 96%) as a white solid. MS (ESI): mass calcd. for $C_8H_{14}N_2$, 138.12; m/z found 139.25, [M+H]$^+$; $^1$H NMR: (300 MHz, DMSO-d$_6$): δ 8.14 (s, 3H), 2.96-2.84 (m, 1H), 2.46 (d, J=6.3 Hz, 2H), 1.98 (d, J=11.1 Hz, 2H), 1.79 (d, J=12.0 Hz, 2H), 1.64-1.49 (m, 1H), 1.42-1.29 (m, 2H), 1.18-1.04 (m, 2H).

Step E: 2-((1r,4r)-4-((5-Nitro-1-(phenylsulfonyl)-1H-pyrrolo[2,3-b]pyridin-4-yl)amino)cyclohexyl)acetonitrile. To a 1000 mL round bottom flask containing 2-[(1r,4r)-4-aminocyclohexyl]acetonitrile hydrochloride (29.10 g, 166.6 mmol) was added DMA (400 mL). The resulting suspension was treated with 4-chloro-5-nitro-1-(phenylsulfonyl)-1H-pyrrolo[2,3-b]pyridine (51.53 g, 152.6 mmol), followed by DIPEA (63.0 mL, 366 mmol). The reaction mixture was placed under $N_2$ and heated at 80° C. for 4 h. The crude reaction mixture was cooled to room temperature and slowly poured into a vigorously stirred 2 L flask containing 1.6 L water. The resulting suspension was stirred for 15 minutes at room temperature, then filtered and dried for 16 h in a vacuum oven with heating at 70° C. to provide the title compound (63.37 g, 95%) as a yellow solid. MS (ESI): mass calcd. for $C_{21}H_{21}N_5O_4S$, 439.1; m/z found, 440.1 [M+H]$^+$. $^1$H NMR (500 MHz, CDCl$_3$): δ 9.10 (s, 1H), 8.99 (d, J=7.8 Hz, 1H), 8.23-8.15 (m, 2H), 7.66-7.59 (m, 2H), 7.56-7.49 (m, 2H), 6.67 (d, J=4.2 Hz, 1H), 3.95-3.79 (m, 1H), 2.38 (d, J=6.2 Hz, 2H), 2.32-2.21 (m, 2H), 2.08-1.98 (m, 2H), 1.88-1.76 (m, 1H), 1.60-1.32 (m, 4H).

Intermediate 2

2-((1r,4r)-4-((5-Amino-1-(phenylsulfonyl)-1H-pyrrolo[2,3-b]pyridin-4-yl)amino)cyclohexyl)acetonitrile

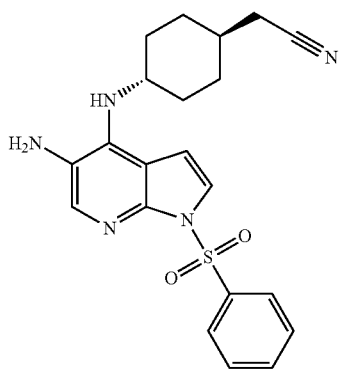

2-((1r,4r)-4-((5-Nitro-1-(phenylsulfonyl)-1H-pyrrolo[2,3-b]pyridin-4-yl)amino)cyclohexyl)acetonitrile (Intermediate 1, 58.60 g, 133.3 mmol) was dissolved in THF/MeOH (1:1, 4800 mL). The mixture was passed through a continuous-flow hydrogenation reactor (10% Pd/C), such as a Thales Nano H-Cube®, at 10 mL/min with 100% hydrogen (atmospheric pressure, 80° C.), then the solution was concentrated to provide the product as a purple solid. The solid was triturated with EtOAc (400 mL) and then triturated again with MeOH (200 mL) then filtered and dried under vacuum to provide the title compound (50.2 g, 91.9% yield). MS (ESI): mass calcd. for $C_{21}H_{23}N_5O_2S$, 409.2; m/z found, 410.2 [M+H]$^+$. $^1$H NMR (400 MHz, CDCl$_3$) δ 8.10-8.03 (m, 2H), 7.76 (s, 1H), 7.51-7.43 (m, 1H), 7.43-7.34 (m, 3H), 6.44 (d, J=4.2 Hz, 1H), 4.61 (d, J=8.5 Hz, 1H), 3.65-3.51 (m, 1H), 2.74 (s, 2H), 2.26 (d, J=6.4 Hz, 2H), 2.19-2.05 (m, 2H), 1.97-1.86 (m, 2H), 1.76-1.59 (m, 1H), 1.33-1.12 (m, 4H).

Intermediate 3

Ethyl 2-(1-((1r,4r)-4-(cyanomethyl)cyclohexyl)-6-(phenylsulfonyl)-1,6-dihydroimidazo[4,5-d]pyrrolo[2,3-b]pyridin-2-yl)acetate

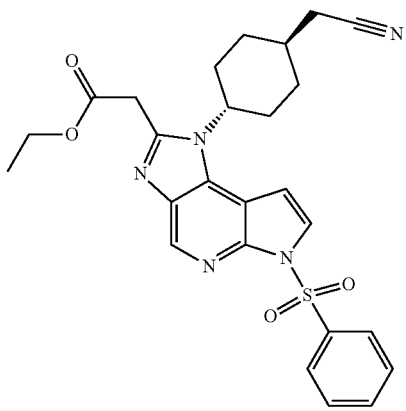

To a 1 L round bottom flask containing a stir bar and 2-((1r,4r)-4-((5-amino-1-(phenylsulfonyl)-1H-pyrrolo[2,3-b]pyridin-4-yl)amino)cyclohexyl)acetonitrile (Intermediate 2, 58.31 g, 142.4 mmol) was added ethyl 3-ethoxy-3-iminopropanoate (60.51 g, 309.3 mmol), followed by EtOH (600 mL, dried over 3 Å molecular sieves for 48 h). A reflux condenser was attached to the reaction flask, the reaction was purged with N$_2$, and was heated at 90° C. for 9 h. The reaction mixture was cooled to room temperature and left to stand for 30 h where the product crystallized out as brown needles. The solids were broken up with a spatula and the reaction mixture was transferred to a 2 L flask. Water (1.4 L) was added slowly via separatory funnel with vigorous stirring. After addition of the water was complete, the suspension was stirred for 30 minutes. The brown needles were isolated by filtration and then dried by pulling air through the filter for 1 h. The product was transferred to a 500 mL flask and treated with EtOAc (200 mL). A small quantity of seed crystals were added, which induced the formation of a white solid precipitate. The suspension was stirred for 30 minutes at room temperature, filtered, rinsed with EtOAc (25 mL), and dried under vacuum to provide the product as a white solid (48.65 g, 68% yield). MS (ESI): mass calcd. for $C_{26}H_{27}N_5O_4S$, 505.2; m/z found, 506.2 [M+H]$^+$. $^1$H NMR (400 MHz, CDCl$_3$) δ 8.85 (s, 1H), 8.28-8.19 (m, 2H), 7.84 (d, J=4.0 Hz, 1H), 7.61-7.53 (m, 1H), 7.52-7.43 (m, 2H), 6.84 (d, J=4.1 Hz, 1H), 4.32 (s, 1H), 4.20 (q, J=7.1 Hz, 2H), 4.09 (s, 2H), 2.44 (d, J=6.2 Hz, 2H), 2.40-2.27 (m, 2H), 2.16 (d, J=13.3 Hz, 2H), 2.12-1.96 (m, 3H), 1.54-1.38 (m, 2H), 1.27 (t, J=7.1 Hz, 3H).

Polymorph Screening Example

Some embodiments of compound of Formula I as free bases present multiple crystalline configurations that have a complex solid-state behavior, some of which in turn can present distinguishing features among themselves due to different amounts of incorporated solvent. Some embodiments of compound of Formula I are in the form of pseudopolymorphs, which are embodiments of the same compound that present crystal lattice compositional differences due to different amounts of solvent in the crystal lattice itself. In addition, channel solvation can also be present in some crystalline embodiments of compound of Formula I, in which solvent is incorporated within channels or voids that are present in the crystal lattice. For example, the various crystalline configurations given in Table 2 were found for compound of Formula I. Because of these features, non-stoichiometric solvates were often observed, as illustrated in Table 2. Furthermore, the presence of such channels or voids in the crystal structure of some embodiments according to this invention enables the presence of water and/or solvent molecules that are held within the crystal structure with varying degrees of bonding strength. Consequently, changes in the specific ambient conditions can readily lead to some loss or gain of water molecules and/or solvent molecules in some embodiments according to this invention. It is understood that "solvation" (third column in Table 2) for each of the embodiments listed in Table 2 is the formula solvation, and that the actual determination of the same as a stoichiometry number (fourth column in Table 2) can slightly vary from the formula solvation depending on the actual ambient conditions when it is experimentally determined. For example, if about half of the water molecules in an embodiment may be present as hydrogen-bonded to the active compound in the crystal lattice, while about the other half of water molecules may be in channels or voids in the crystal lattice, then changes in ambient conditions may alter the amount of such loosely contained water molecules in voids or channels, and hence lead to a slight difference between the formula solvation that is assigned according to, for example, single crystal diffraction, and the stoichiometry that is determined by, for example, thermogravimetric analysis coupled with mass spectroscopy.

can slightly differ due to the different composition (solvent or water incorporated into the crystal structure). Embodiments referred to in Table 2 were prepared and/or inter-

TABLE 2

Embodiments of crystalline forms of compound of Formula I

| Embodiment | Crystallization solvent | Solvation | Stoichiometry |
|---|---|---|---|
| 1s | — | monohydrate | 0.8 $H_2O$ |
| 1a | Water | monohydrate | 1.3 $H_2O$ |
| 1b | Toluene | Toluene solvate | 0.4 toluene |
| 1c | Ethyl acetate/1,4-dioxane | monohydrate | 1.1 $H_2O$ |
| 1d | Acetonitrile/chloroform | 1.7 hydrate | 1.7 $H_2O$ |
| 1e | Ethyl acetate/1,4-dioxane | monohydrate | 1 $H_2O$ |
| 1f | p-xylene | p-xylene solvate | 0.3 p-xylene |
| 1f | Cumene | Cumene solvate | 0.3 cumene |
| 1g | Anisole | Anisole solvate | 0.3 anisole |
| 1h | p-xylene | p-xylene solvate | 0.2 p-xylene |
| 2 | 1,4-dioxane | 1,4-dioxane solvate | 1.2 1,4-dioxane |
| 3b | Cyclohexanone | Cyclohexanone solvate | 0.3 Cyclohexanone |
| 3c | 1,4-dioxane | 1,4-dioxane solvate | 0.5 1,4-dioxane |
| 3d | THF | THF solvate | 0.4 THF |
| 3e | Isobutanol | Isobutanol solvate | 0.7 isobutanol |
| 1b + 4 | Water/methanol | Mix hydrate/methanol solvate | — |
| 5 | Chloroform | Chloroform solvate | 0.5 chloroform |
| 6 | Acetonitrile | Anhydrous | 0.2 acetonitrile |
| 1s + 7 | Heptane | Heptane solvate | 0.1 heptane |
| 7 | — | Non-solvated | — |
| 8 | — | Non-solvated | — |
| 9 | — | Non-solvated | — |
| 10 | | dihydrate | 1.8 $H_2O$ |
| 11 | ethanol | ethanol solvate | 0.5 ethanol |
| 11b | methanol | methanol solvate | 0.5 methanol |
| 12 | — | anhydrous | — |
| 13 | methanol/water | metastable form | |
| 14 | | metastable hydrate | |
| 15 | toluene | toluene solvate | 0.55 toluene |
| 16 | ethyl acetate | ethyl acetate solvate | 0.09 ethyl acetate |
| 17 | isopropyl acetate | isopropyl acetate solvate | 0.13 isopropyl acetate |
| 18 | 2-butanone | 2-butanone solvate | 0.2 2-butanone |

The compound that was obtained as described in Example 1 was further crystallized by preparing a slurry in DCM (1:3, for example 10 g of compound in 30 ml DCM) that was stirred at 40° C. for 4 hours, and further stirred for 14 hours at 25° C., then heptane was slowly added (1:2, for example 20 ml of heptane into the compound/DCM slurry/solution) at 25° C., stirred at 40° C. for 4 hours, cooled to 25° C. and stirred for further 14 hours at 25° C. Subsequent filtration led to compound of Formula I in the form of an off-white solid, that was identified as a monohydrate, a 1s embodiment.

Figure 1:
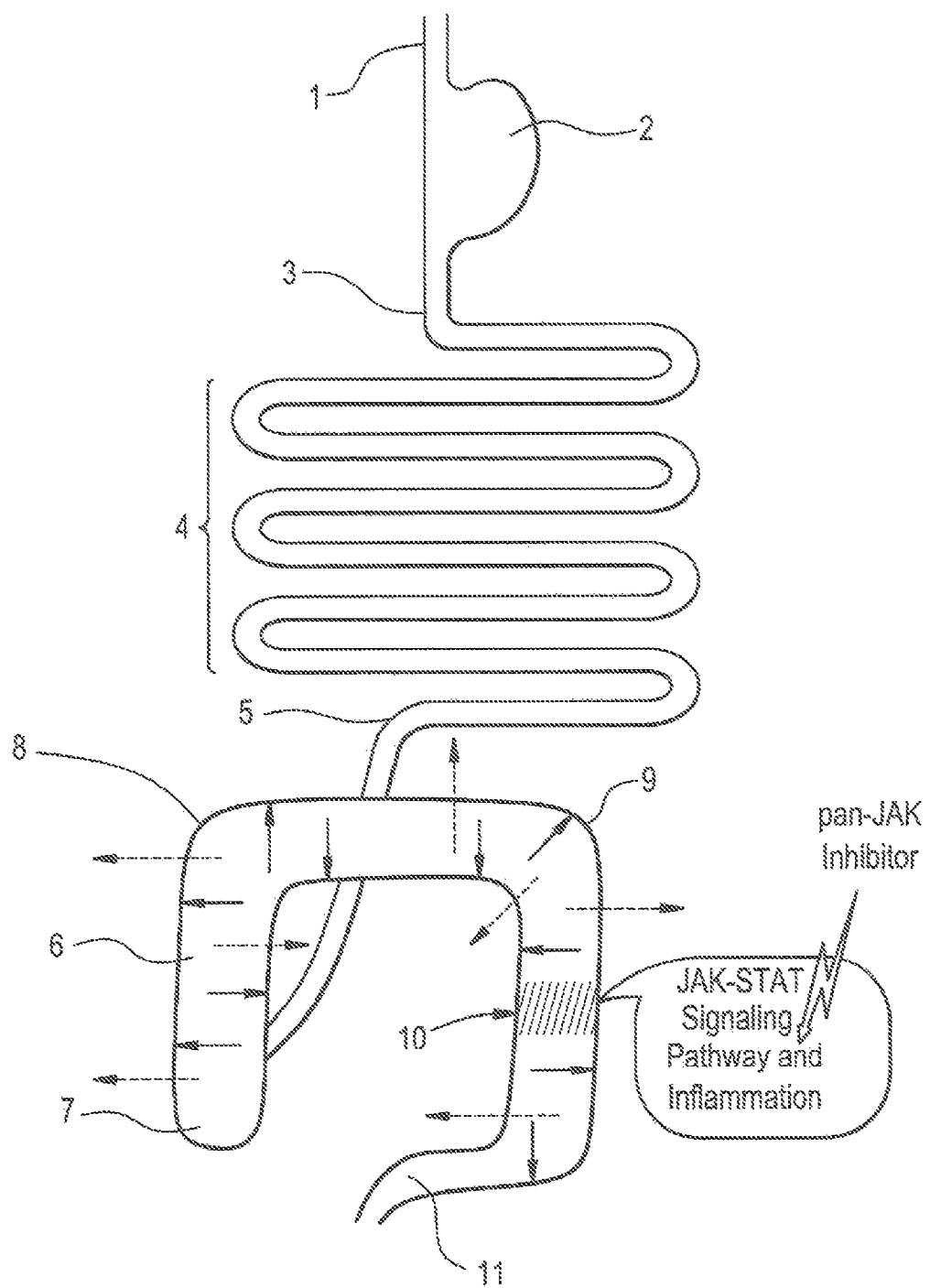
FIG. 1. Schematic diagram of part of the human gastrointestinal tract, shown as a not-at-scale stretched rendering. The duodenum (3), jejunum (4), and ileum (5) (all schematically shown) form the small intestine after the stomach (2) and esophagus (1). The large intestine comprises the colon (6), in turn including the cecum (7) and appendix (not shown), ascending colon, transverse colon, descending colon, sigmoid colon (loop in the same not shown), and rectum (11). The transverse colon is the portion comprised between the right (8) and left (9) colonic flexures, the ascending colon extends from the cecum (7) to the right colonic flexure (8), and the descending colon extends from the left colonic flexure (9) to the rectum (11). Various distribution patterns are illustrated in reference to the colon for convenience, but they can also refer to other parts of the gastrointestinal tract. Systemic distribution is represented by dashed line arrows in FIG. 1 as permeating through the colon walls for simplified illustrative purposes, but such distribution is not limited to the colon walls, for it also can take place through the walls of other parts of the gastrointestinal tract shown in FIG. 1, such as those of the small intestine. Distribution with some tissue penetration is represented by solid line arrows in FIG. 1 as penetrating the colon tissue for simplified illustrative purposes, but such penetration is not limited to the colon tissue, for it also can take place in the tissue of other parts of the gastrointestinal tract shown in FIG. 1, such as the tissue of the small intestine. The effect of an embodiment of a JAK inhibitor according to this invention is illustratively shown as disrupting the JAK/STAT signaling pathway that otherwise would lead to a disorder mediated by JAK, such as inflammation associated with an inflammatory bowel disease ("IBD") or colorectal cancer.
Figure 2:
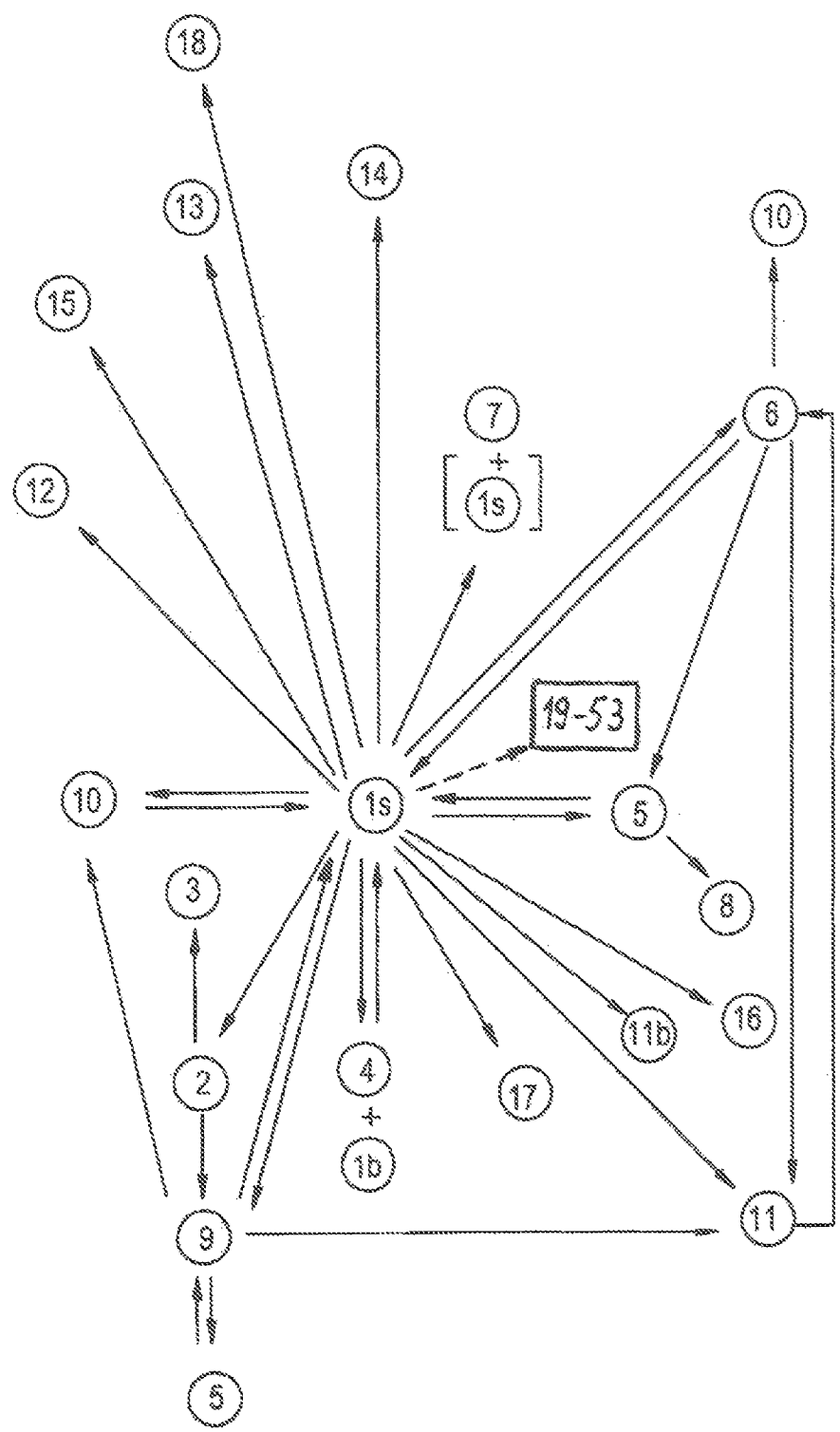
FIG. 2. Schematic diagram showing the preparation/interconversion of embodiments of compound of Formula I.

Embodiments 1-10 in Table 2 and FIG. 2 are crystalline. Embodiments 1s and 1a through 1h are isostructural. Embodiment 1s crystallizes in a centro-symmetrical triclinic space group P-1. The term "embodiment 1" collectively refers to the isostructural embodiments 1s and 1a through 1h. Any one of such 1s and 1a through 1h embodiments is sometimes referred to as an isostructural member of embodiment 1 or just as a member of embodiment 1. Embodiments 3b, 3c, 3d and 3e are isostructural and crystallize in the monoclinic system, space group C 2/c. The term "embodiment 3" collectively refers to the isostructural embodiments 3b, 3c, 3d and 3e. Any one of such 3b, 3c, 3d and 3e embodiments is sometimes referred to as an isostructural member of embodiment 3 or just as a member of embodiment 3. Isostructural embodiments are such that they possess similar crystal structure properties (same symmetries and similar unit cell parameters and crystal packing) while having different chemical compositions (i.e., different solvent and/or water molecules incorporated in the crystal lattice). Unit cell parameters in isostructural embodiments converted as schematically shown in FIG. 2 and as described in more detail in the following screening techniques.

Screening included crystallization protocols such as solvent equilibration in neat solvents, evaporative crystallization, cooling crystallization with hot filtration, crash-crystallization with anti-solvent, and crystallization by thermocycling. Solids were analyzed by HT-XRPD. When applicable, mother liquors were evaporated completely and the remaining solids were also analyzed by HT-XRPD. The predominant solid form that was identified was the starting material embodiment 1s as a monohydrate.

Solvent Equilibration at 25° C. and 50° C.

Long term slurry experiments were performed by suspending compound embodiment 1s in twenty neat solvents and stirred at room temperature for two weeks and at 50° C. for one week. Upon completion of the equilibration time, the residual solids were separated from the mother liquors. The solids were dried under ambient conditions and dried under vacuum (5 mBar) before being analyzed by HT-XRPD. Subsequently, the solids were exposed to accelerated aging conditions (40° C./70% relative humidity) for two days and again analyzed by HT-XRPD.

From most of the crystallization solvents, the starting material as embodiment 1s was obtained. From several crystallization solvents, HT-XRPD patterns were found to be similar to those of the initial embodiment 1s. In most of these diffraction patterns, peak shifts and/or additional peaks were identified. Each of these patterns corresponded to an embodiment that was labeled as one of 1a through 1h, and based on the similarities in the HT-XRPD diffraction patterns for such embodiments, they are presented as embodiments that are isostructural members of embodiment 1. All isostructural members of embodiment 1 converted to embodiment 1a after exposure to 40° C. and 75% RH for two days.

Embodiment 1s converted to hydrated embodiment 10 when it was exposed to 100% RH at 25° C. Nevertheless, embodiment 10 was physically not stable at ambient conditions. Whereas embodiment 1s crystallized in the triclinic system, space group P-1, embodiment 10 was found to crystallize in the monoclinic system, space group C 2/c. Embodiment 10 had limited physical stability under ambient conditions and it converted to another embodiment such as 1s or 1a. This behavior is attributable to an unequally strong binding of all the hydration/solvation molecules. In this case, embodiment 10 would have a less strongly bound second water molecule that would be lost under ambient conditions. More precisely, the physical stability of embodiment 1s was investigated in climate chambers by exposing a 20 mg sample of such embodiment to 40° C. and 70% relative humidity for four days, and another 20 mg sample of the same embodiment was exposed also for four days to 25° C. and 100% relative humidity. After four days, the various solid samples were analyzed by HR-XRPD, the crystal cell parameters were determined and the diffractograms were indexed. Diffractograms are shown in FIG. 6. From bottom to top, the first diffractogram in FIG. 6 corresponds to embodiment 1s as starting material, and the second corresponds to the same form after a 4-day exposure to 40° C. and 70% relative humidity, noted as "1s 70 RH" in the same figure. This analysis revealed that the initial embodiment 1s had been recovered although with a small amount of a second crystalline form that was possibly another hydrated embodiment with a higher water content. Indexing for such form was not possible due to the small amount in which it was present. The third diffractogram corresponds to embodiment is after a 4-day exposure to 25° C. and 100% relative humidity, noted as "10" in the same figure. These conditions lead to the conversion of embodiment 1s into embodiment 10, with a small contamination of initial embodiment 1s, and solvation as characterized in Table 2. Upon dehydration, both embodiments 1s and 10 re-crystallized to the anhydrous form with a melting point of 148° C.

Solvent equilibration at room temperature yielded embodiment 1b out of toluene as the crystallization solvent, and embodiment 1f out of p-xylene as the crystallization solvent.

Three additional solid embodiments were identified and designated as embodiments 2, 3 and 7. Embodiment 2, whose TGA and DSC are shown in FIGS. 21A and 21B, respectively, was identified from the solvent equilibration experiment performed at room temperature in 1,4-dioxane while embodiment 7 was found as a mixture with embodiment 1s in the single solvent equilibration experiment at 50° C. from heptane. Several similar but not identical diffractograms were identified which were grouped as embodiments 3b, 3c, 3d and 3e that are isostructural members of embodiment 3. Isostructural members of embodiment 3 were found mixed with members of embodiment 1. The mixtures containing members of embodiment 3 transformed in some cases to embodiment 1a or to mixtures of embodiments 1a and 3e. Embodiment 7 appeared to be physically stable, but embodiment 2 converted to embodiment 3e after exposure to AAC for two days.

Evaporative Crystallization

The mother liquors saved from the solvent equilibration experiments performed at RT were used for slow evaporative crystallization experiments. The mother liquors were filtered to remove any particulate matter and allowed to slowly evaporate under ambient conditions. The obtained solids were analyzed by HT-XRPD and again after exposure to AAC for two days.

Due to the poor solubility of compound of Formula I in some of the solvents, no solids were recovered when such solvents were used. In the experiments where solids had precipitated, an amorphous residue or isostructural members of embodiments 1 or 3 were recovered. During the stability study, the different members of embodiment 1 converted to embodiment 1a whilst the sample of embodiment 3 seemed to be physically stable. The amorphous solids in some cases remained amorphous after the stability study, became deliquescent or showed some signs of crystallinity.

Cooling crystallization

The mother liquors of the solvent equilibration experiments performed at 50° C. were filtered at 50° C. to remove any particulate matter. The suspensions at 50° C. were filtered using 0.2 μm PTFE filters, and the solutions were placed at 5° C. and aged for 72 hours. When solids had precipitated during aging these solids were separated from the liquid, dried under ambient conditions and under vacuum, and analyzed by HT-XRPD. The remaining mother liquors were allowed to slowly evaporate and the remaining solids were analyzed by HT-XRPD. The samples in which no precipitation occurred were placed under vacuum and the dried solids were analyzed by HT-XRPD. All the solids were then exposed to AAC (2 days at 40° C./70% RH) and re-analyzed by HT-XRPD.

Solids did not precipitate upon cooling in some of the solutions, in which cases the solutions were evaporated under ambient conditions. Due to the low solubility of compound of Formula I in some solvents, no solids were obtained from some solutions.

From four solvents (2-propanol, 2-butanone, acetonitrile, and methanol), precipitation occurred. Embodiment 6 was identified after evaporation of a single cooling crystallization experiment at mL scale in 800 μL acetonitrile, concentration of 25 mg/mL. Embodiment 6 seemed to be a stable solid form after 2 days AAC, and it appeared as a non-solvated embodiment.

Cooling/Evaporative Crystallization at μL Scale

The cooling/evaporative crystallization experiments at μL scale were performed in a 96-well plate, using 12 neat solvents and 12 solvent mixtures and applying four temperature profiles. In each well approximately 4 mg of embodiment 1s was solid dosed. Subsequently, the crystallization solvents (80 μL) and solvent mixtures were added to reach a concentration of 50 mg/mL, and the plate, with each well individually sealed, to subsequently undergo one of the four temperature profiles. Upon completion of the temperature profile the solvents were allowed to evaporate at low ambient pressure (24 hours) and the remaining solids were analyzed by HT-XRPD before and after exposure to AAC for 2 days (40° C./70% RH).

Members of embodiments 1 and 3 were found from most of the solvent systems and temperature profiles. However, a certain tendency of solid form versus temperature profile was observed. Embodiment 1b was mainly identified from the short temperature profiles (3 hours aging). Nevertheless, the same solvent systems with long aging times led to the identification of embodiment 1f, members of embodiment 3 or mixtures of members of embodiments 1 and 3. Embodiment 3c was obtained with 1,4-dioxane as crystallization solvent and a temperature profile of 50° C. as initial temperature, held for 60 min, followed by cooling at a rate of 1° C./h to a final temperature of 20° C., held for 48 h; embodiment 3d was obtained with tetrahydrofuran as crystallization solvent and the same temperature profile as for embodiment 3c.

Embodiment 4 was identified in experiments performed in methanol/water (50/50, v/v), THF and DCM/IPA (50/50, v/v) when short aging conditions were applied. Embodiment 4 was obtained by treating embodiment 1s with a mixture (50/50) of water and methanol and a temperature profile of 50° C. as initial temperature, held for 60 min, followed by cooling at a rate of 20° C./h to a final temperature of 5° C., held for 3 h, which yielded embodiment 4 together with embodiment 1b. Embodiment 4 together with embodiment 1b was also obtained by treating is with a mixture (50/50) of water and methanol and a temperature profile of 50° C. as initial temperature, held for 60 min, followed by cooling at a rate of 20° C./h to a final temperature of 20° C., held for 3 h. Embodiment 4 did not appear to be physically stable under ambient conditions. Cooling crystallization experiments yielded embodiment 1c out of ethyl acetate/1,4-dioxane (50/50, v/v) as the crystallization solvent and a temperature profile of 50° C. as initial temperature, held for 60 min, followed by cooling at a rate of 1° C./h to a final temperature of 5° C., held for 48 h; embodiment 1d out of acetonitrile/chloroform (50/50, v/v) as the crystallization solvent and a temperature profile of 50° C. as initial temperature, held for 60 min, followed by cooling at a rate of 1° C./h to a final temperature of 5° C., held for 48 h; and embodiment 1e out of ethyl acetate/1,4-dioxane (50/50, v/v) as the crystallization solvent and a temperature profile of 50° C. as initial temperature, held for 60 min, followed by cooling at a rate of 1° C./h to a final temperature of 20° C., held for 48 h.

Embodiment 5 was identified in experiments performed in chloroform as the crystallization solvent and a temperature profile of 50° C. as initial temperature, held for 60 min, followed by cooling at a rate of 1° C./h to a final temperature of 20° C., held for 48 h.

Similar conversions were seen during the stability study as previously observed in the other crystallization methods. In most cases all solid forms converted to embodiment 1a or to mixtures containing embodiment 1a.

Evaporative Crystallization from Solid Mixtures

In evaporative crystallization using solvent/anti-solvent mixtures, clear solutions of a compound are prepared from which the solvent evaporates first (high vapor pressure) causing the compound to precipitate to some extent in the form of crystals. These crystals then act as seeds when the anti-solvent (lower vapor pressure) is evaporated.

Compound of Formula I did not completely dissolve in each of the solvent systems. For that reason, all the experiments included filtration prior to evaporation.

The results of the HT-XRPD analysis demonstrated that compound of Formula I crystallized mainly as embodiment 1s upon evaporation of solvent mixtures. This was observed for the following solvent/anti-solvent systems: tetrahydrofuran/water, acetonitrile/water, chloroform/ethanol, methanol/ethyl acetate, 2-butanone/isopropanol, and heptane/acetone. From two systems, acetone/cumene and 1,4-dioxane/ethyl formate, the isostructural embodiments 3b and 3e were identified, which after AAC converted to different mixtures of embodiments 1a and 3d, and is and 3e, respectively.

Anti-Solvent Crystallization

Saturated solutions of compound of Formula I were prepared in neat solvents. The anti-solvent additions were performed in forward and reverse additions. In the forward addition, the anti-solvent was added in three aliquots to the compound solution. The reverse addition was performed by adding a volume of compound solution to a large excess of anti-solvent (20 mL).

After precipitation, the solids were separated from the liquids, dried under ambient conditions and dried under vacuum (5 mbar) before being analyzed by HT-XRPD. The experiments in which no precipitation occurred upon anti-solvent addition were stored at 5° C. for 48 hours to induce precipitation. The precipitated solids were afterwards separated and analyzed by HT-XRPD. When no solids were obtained, the solutions were evaporated under mild conditions and the residual solids were analyzed by HT-XRPD. All solids were exposed to AAC (2 days at 40° C./70% RH) and were re-analyzed by HT-XRPD.

The forward anti-solvent crystallization showed precipitation in all cases. All solids could be classified as isostructural members (1s, 1b, 1j, 1f) of embodiment 1 or of embodiment 3 (3b, 3d, 3f). After exposure to AAC, all solid samples converted to embodiment 1a, except one that converted to a mixture of embodiments 1a and 3e.

The reverse anti-solvent crystallization experiments performed in DMSO as solvent gave different solid forms depending on the anti-solvent used. With dichloromethane or p-xylene isostructural members (1s and 1b) of embodiment 1 were identified, while with MTBE an amorphous residue was obtained. Evaporation of two solutions with heptane and water as anti-solvents that had not precipitated upon anti-solvent addition led to an oil. Conversions to embodiment 1a were observed after AAC, and the amorphous residues became deliquescent.

Hot Filtration Experiments

The cooling crystallization experiments with hot filtration were performed from supersaturated solutions of compound of Formula I prepared at 50° C. in different solvent mixtures. The hot filtrated solutions underwent a 48-hour cooling profile. The vials in which solids had precipitated after the temperature profile were centrifuged and the solids were separated from the liquid and analyzed by HT-XRPD (after drying under vacuum). If no solids had precipitated the solutions were evaporated under vacuum and the solids analyzed by HT-XRPD. All the solids were exposed to AAC (2 days at 40° C./70% RH) and re-analyzed by HT-XRPD. In half of the hot filtration experiments precipitation did not occur and upon evaporation of the solvents, not enough solids were recovered due to the poor solubility of compound of Formula I in those solvent systems. In three experiments, an amorphous residue was recovered which after AAC crystallized to a mixture of members of embodiment 1 (1s or 1a) and 3 (3e) or became deliquescent. Embodiment 5 was identified from the experiment in acetone/chloroform (50/50, v/v). This embodiment appeared to be physically unstable as conversion to embodiment 1a was observed after AAC.

Thermo-Cycling Experiments

Suspensions of about 6 mg of embodiment 1s were prepared in 10 solvents at room temperature. The suspensions were cycled between 5° C. and 50° C. Upon completion of the thermo-cycling, the solids were separated by centrifugation and dried under ambient conditions and under vacuum (5 mbar) before being analyzed by HT-XRPD. Subsequently, all solids were exposed to AAC for two days and again analyzed by HT-XRPD. Thermo-cycling experiments usually promote the formation of the more stable polymorphic form. With the exception of the experiment performed in cyclohexanone all vials contained solids after the thermo profile. The cyclohexanone solution was slowly evaporated under mild vacuum. Members of embodiments 1, 3 or mixtures of them were identified mainly in the wet solids. Upon drying these solids, conversion to embodiment 1s was observed. Embodiments 3b and 3e were obtained from thermo-cycling in 300 μL of cyclohexanone at a concentration of 51 mg/mL (3b), and in 400 μL of isobutanol at a concentration of 37.3 mg/mL (3e). Embodiment 5 was obtained from thermo-cycling in 800 μL of chloroform at a concentration of 18.6 mg/mL.

Figure 3:
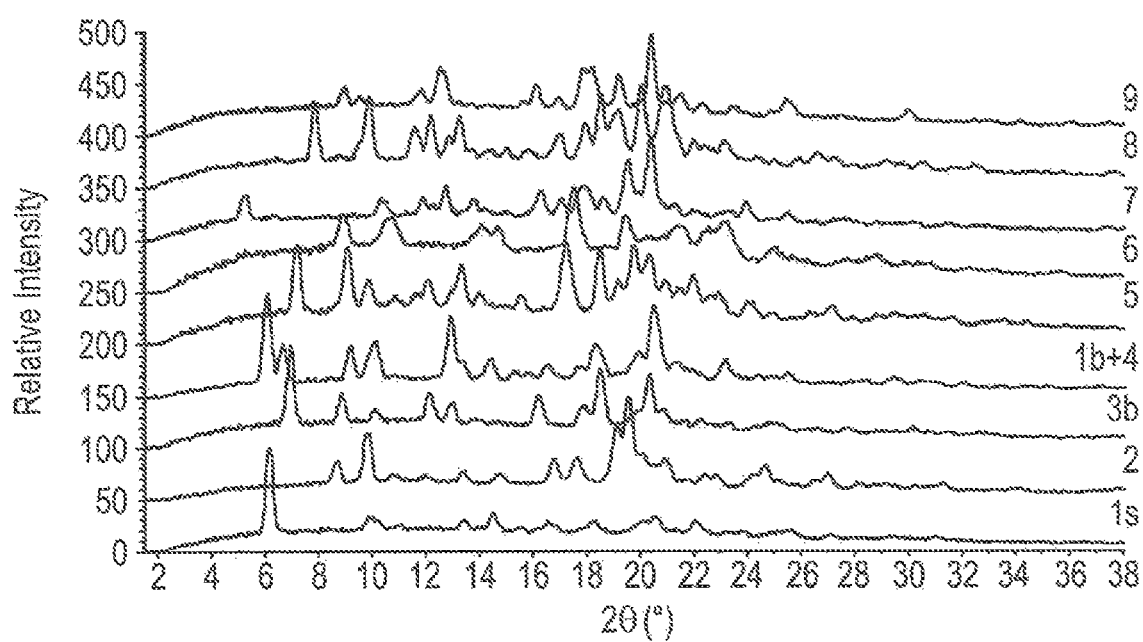
FIG. 3. Overlay of high throughput X-ray powder diffraction (HT-XRPD) patterns for the following embodiments of compound of Formula I, from bottom to top: 1s, 2 (obtained by equilibration at room temperature in 1,4-dioxane), 3b (obtained by thermocycling in cyclohexanone), 1b+4 (obtained by cooling crystallization at µL scale in methanol/water (50/50, v/v)), 5 (obtained by thermocycling in chloroform), 6 (obtained by cooling crystallization at mL scale in acetonitrile), 7 (obtained of 1s+7, in turn obtained by solvent equilibration in heptane), 7 (obtained by desolvation of 1s+7, in turn obtained by solvent equilibration in heptane), 8 (obtained by desolvation of embodiment 5 by cycling differential scanning calorimetry)), and 9 (obtained by desolvation of embodiment 2 by cycling differential scanning calorimetry).
Figure 4:
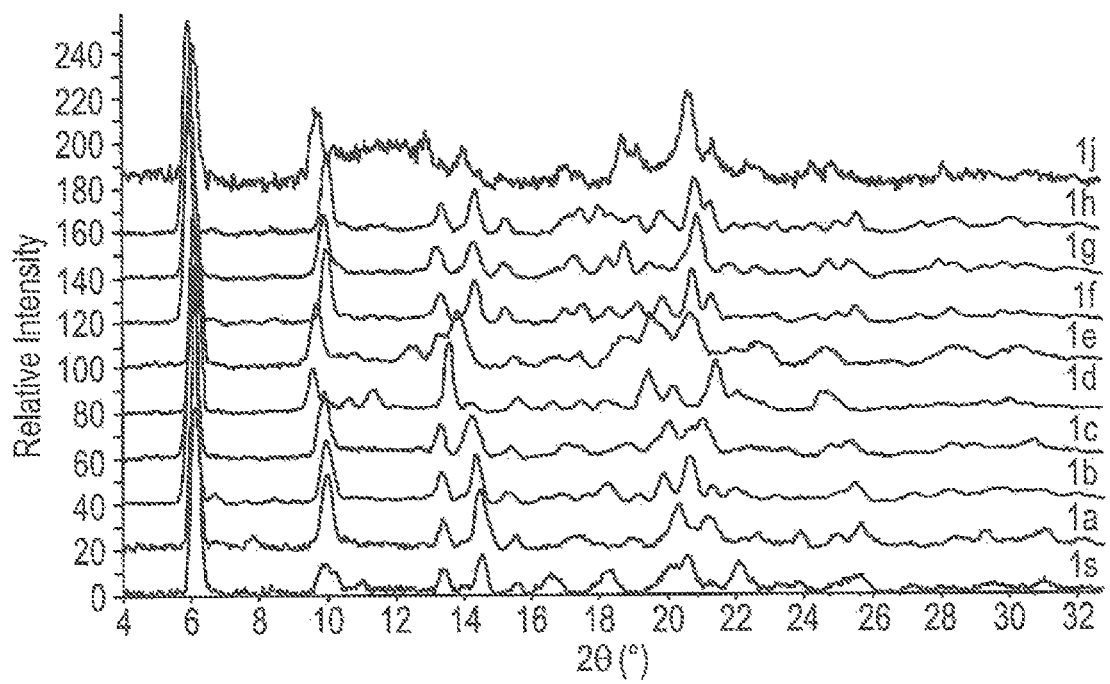
FIG. 4. Overlay of high throughput X-ray powder diffraction (HT-XRPD) patterns for the following embodiments of compound of Formula I, from bottom to top: 1s (starting material), 1a (obtained after exposure to accelerated aging conditions (AAC) (40° C. and 70% relative humidity) several forms of samples of embodiment 1s), 1b (obtained by solvent equilibration at room temperature in toluene), 1c (obtained by cooling crystallization at µL scale in ethyl acetate/1,4-dioxane (50/50, v/v)), 1d (obtained by cooling crystallization at µL scale in acetonitrile/chloroform (50/50, v/v)), 1e (obtained by cooling crystallization at µL scale in ethyl acetate/1,4-dioxane (50/50, v/v)), 1f (obtained by solvent equilibration at room temperature in p-xylene), 1g (obtained by solvent equilibration at 50° C. in anisole), 1h (obtained by cooling crystallization at µL scale in p-xylene).
Figure 5:
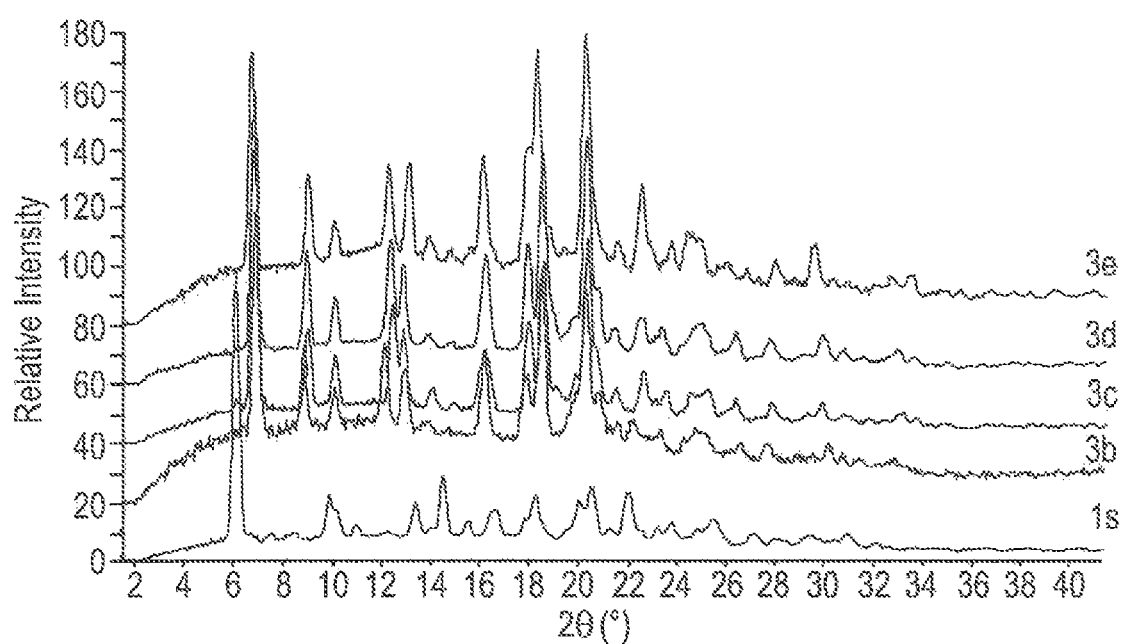
FIG. 5. Overlay of high throughput X-ray powder diffraction (HT-XRPD) patterns for the following embodiments of compound of Formula I, from bottom to top: 1s, 3b (obtained by thermocycling in cyclohexanone), 3c (obtained by cooling crystallization at µL scale in 1,4-dioxane), 3d (obtained by cooling crystallization at µL screen in tetrahydrofuran), and 3e (obtained by thermocycling in isobutanol).

FIGS. 3, 4 and 5 show an overlay of HT-XRPD patterns for the embodiments listed in Table 2 and also referred to in the screenings described above.

Embodiment 1s was recovered from most of the crystallization experiments. It is a channel hydrate having a variable number of water molecules and/or other solvents incorporated depending on ambient conditions. Conversion to embodiment 1a was observed. This form contained slightly more water (1.3 molecules of water). All isostructural members of embodiment 1 converted to embodiment 1a after exposure to 40° C. and 75% RH for two days. The shifts of some diffraction peaks in XRPD patterns for members of embodiment 1 might be attributed to the different solvent or water molecules that were incorporated into the crystal lattice. FIG. 4 shows an overlay of HT-XRPD patters for members of embodiment 1. Diffractogram is corresponds to compound of Formula I as starting material in the form of embodiment 1s. Diffractogram 1a corresponds to embodiment 1a that was obtained after exposure to AAC of several embodiment 1s samples. Diffractogram 1b corresponds to embodiment 1b that was obtained from the solvent equilibration experiment at RT in toluene. Diffractogram 1c corresponds to embodiment 1c that was obtained from the cooling crystallization experiment at μL scale in ethyl acetate/1,4-dioxane (50/50, v/v). Diffractogram 1c corresponds to embodiment 1d that was obtained from the cooling crystallization experiment at μL scale in acetonitrile/chloroform (50/50, v/v). Diffractogram 1e corresponds to embodiment 1e that was obtained from the cooling crystallization experiment at μL scale in ethyl acetate/1,4-dioxane (50/50, v/v). Diffractogram 1f corresponds to embodiment 1f that was obtained from the solvent equilibration experiment at RT in p-xylene. Diffractogram 1g corresponds to embodiment 1g that was obtained from the solvent equilibration experiment at 50° C. in anisole. Diffractogram 1h corresponds to embodiment 1h obtained from the cooling crystallization experiment at μL scale in p-xylene.

Diffractograms for members of embodiment 3 are shown in FIG. 5. The shifts observed in the different HT-XRPD patterns are most likely attributed to the different solvent molecules that were incorporated into the crystal lattice. Embodiment 3 was obtained by heating embodiment 2 to 40° C. at 70% RH for 4 days. Embodiments 3b through 3e were solvated forms containing a non-stoichiometric amount of solvent which varied depending on the solvent incorporated in the crystal structure (0.3-0.7 molecules). The mixtures containing members of embodiment 3 were unstable upon exposure to AAC and they transformed in some cases to embodiment 1a or to mixtures of embodiments 1a and 3e. Conversion to embodiment 1a is attributed to the exchange of solvent molecules by water molecules upon exposure to high relative humidity, and re-crystallization to the hydrated embodiment 1a.

Embodiment 9 was obtained by heating embodiment 2 to a temperature of about 200° C. followed by cooling to 25° C. and also by cyclic DSC 25-200-25-300° C.

Embodiment 9 was also obtained by additional procedures. One of such procedures was a two-step procedure: Embodiment 1s (1.5 g) was treated with 1,4-dioxane (10 vol) at RT. Seeds of embodiment 2 (5 mg) were added and the sample was stirred at RT for 24 hours. The resulting suspension was filtered and the sample was air-dried for 1.5 hours. This sample was determined to be embodiment 2 by XRPD. In the second step of this two-step procedure, embodiment 2 was heated to 210° C. at 10° C./min and held at 210° C. for 30 min. The sample was then allowed to cool to RT. The resulting solid was determined to be embodiment 9 by XRPD analysis. Another of such procedures was also a two-step procedure for obtaining embodiment 9. In this procedure, embodiment 1s (1.5 g) was treated with 1,4-dioaxne (10 vol). Seeds of embodiment 2 (5 mg) were added and the sample was stirred at RT for 24 hours. The resulting suspension was filtered and the sample was air-dried for 1.5 hours. This sample was determined to be embodiment 2 by XRPD. In the second step of this procedure, embodiment 2 was heated to 150° C. at 10° C./min followed by further heating to 170° C. at 2° C./min. The sample was then allowed to cool to RT. The resulting solid was determined to be embodiment 9 by XRPD analysis. The TGA and DSC of embodiment 9 is shown in FIGS. 22A and 22B, respectively.

Embodiment 1s was obtained by slurring embodiment 9 in the following solvents for 6 days at 50° C.: 2-butanone, acetone/water (90/10, v/v) and acetonitrile/water (90/10, v/v). Embodiment 1s was also obtained when the same experiment was performed at room temperature.

Embodiment 8 was obtained by heating embodiment 5 to a temperature of about 175° C. Embodiment 8 was also obtained by additional procedures. One of such procedures was a two-step procedure: Embodiment 1s (1.5 g) was treated with 1,4-dioxane 10 (vol) and stirred at RT for 72 hours. The resulting suspension was filtered and the solid that was obtained was dried in a vacuum oven at RT for 16 hours. The solid obtained from this first step was determined by XRPD to be embodiment 3c. In the second step, embodiment 3c (100 mg) was heated to 150° C. at 10° C./min, then heated at the slower rate of 2° C./min up to 180° C. The sample was then allowed to cool back to RT. The resulting solid was determined by XRPD to be embodiment 8. Another of such procedures was also a two step procedure for obtaining embodiment 8. In this procedure, embodiment 19 (300 mg) was treated with 1,4-dioxane (3 vol) and shaken at 60° C. for 24 hours. The resulting suspension was filtered and the solid obtained from this first step was determined by XRPD to be embodiment 3c. In the second step, embodiment 3c (300 mg) was heated to 180° C. at 10° C./min. The sample was then allowed to cool back to RT. The resulting solid was determined by XRPD to be embodiment 8. The TGA and DSC for embodiment 8 is shown in FIGS. 20A and 20B, respectively.

Figure 19A:
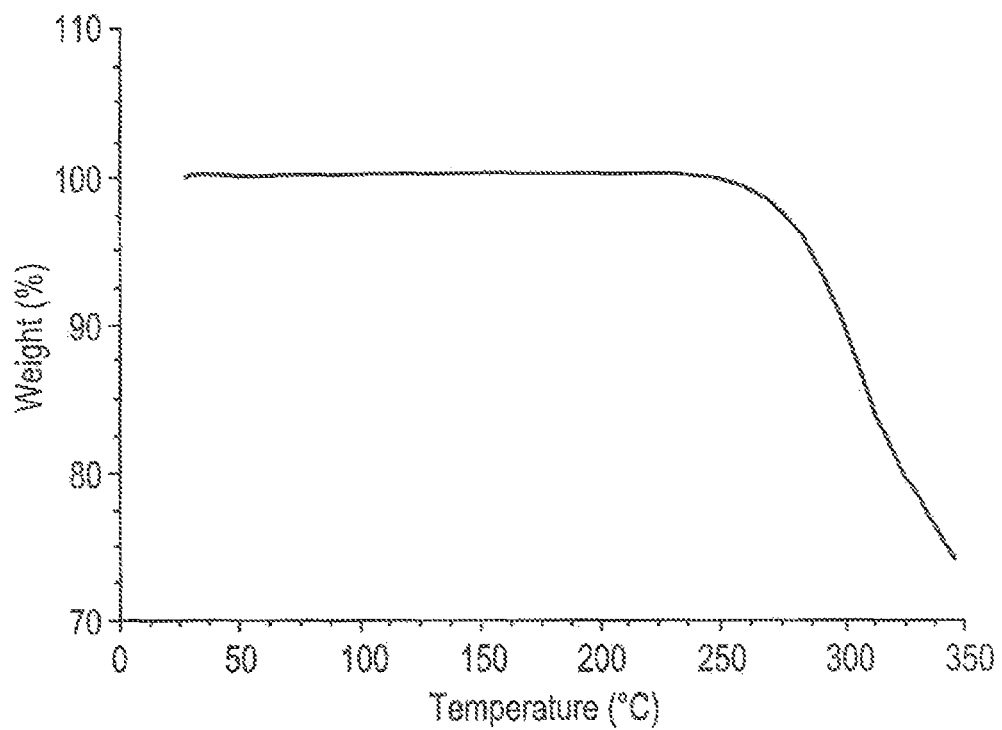
FIGS. 19A-B. (A) TGA of embodiment 6 showing weight loss at temperatures above 260° C., which weight loss is interpreted as being associated with sample degradation; (B)
Figure 19B:
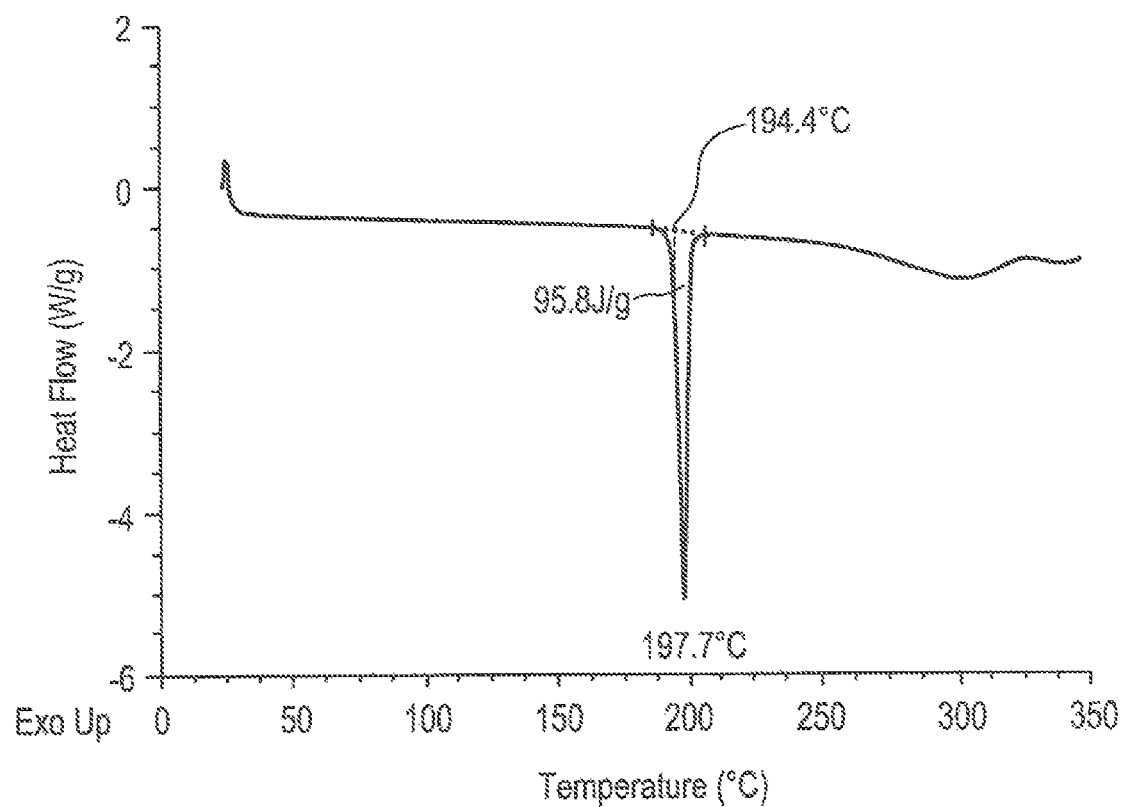

In addition to the preparation of embodiment 6 as described above, this embodiment was obtained by heating embodiment 11 (80-100 mg), whose preparation is described below, by thermal gravimetric analysis from ambient to 185° C. at 10° C./min and was held isothermally for 3 minutes. The sample was then allowed to cool to RT. Embodiment 6 was also obtained from embodiment 11 by subjecting it to a slurry experiment. The slurry experiment was run as follows: the solvent was added to embodiment 11 (50 mg) and the mixture was stirred at the designated temperature for 0.5 hours. Seed crystals of form 9 (5 mg) were added and the mixture was stirred overnight at the designated temperature. The solids were isolated by centrifugation and analyzed by XRPD. using isopropyl acetate (0.5 mL) at both 30° C. and 50° C. The generation of embodiment 6 was confirmed by XRPD. The TGA and DSC for embodiment 6 is shown in FIGS. 19A and 19B, respectively.

Additional embodiments of compound of Formula I were obtained as described below.

Embodiment 5 was converted to embodiment 9 by subjecting it to slurry experiments Slurry experiments were conducted as follows using various solvents at the temperatures identified: The solvent was added to embodiment 5 (50 mg) and the mixture was stirred at the designated temperature for 0.5 hours. Seed crystals of form 9 (5 mg) were added and the mixture was stirred overnight at the designated temperature. The solids were isolated by centrifugation and analyzed by XRPD. Slurry experiments run at 50° C. were conducted using the following solvents: TBME (0.75 mL) and a 33:67 mixture of isopropyl acetate: heptane (0.5 mL). Slurry experiments run at 75° C. were conducted using the following solvents: isopropyl acetate (0.5 mL) and methyl ethyl ketone (0.5 mL).

Figure 17A:
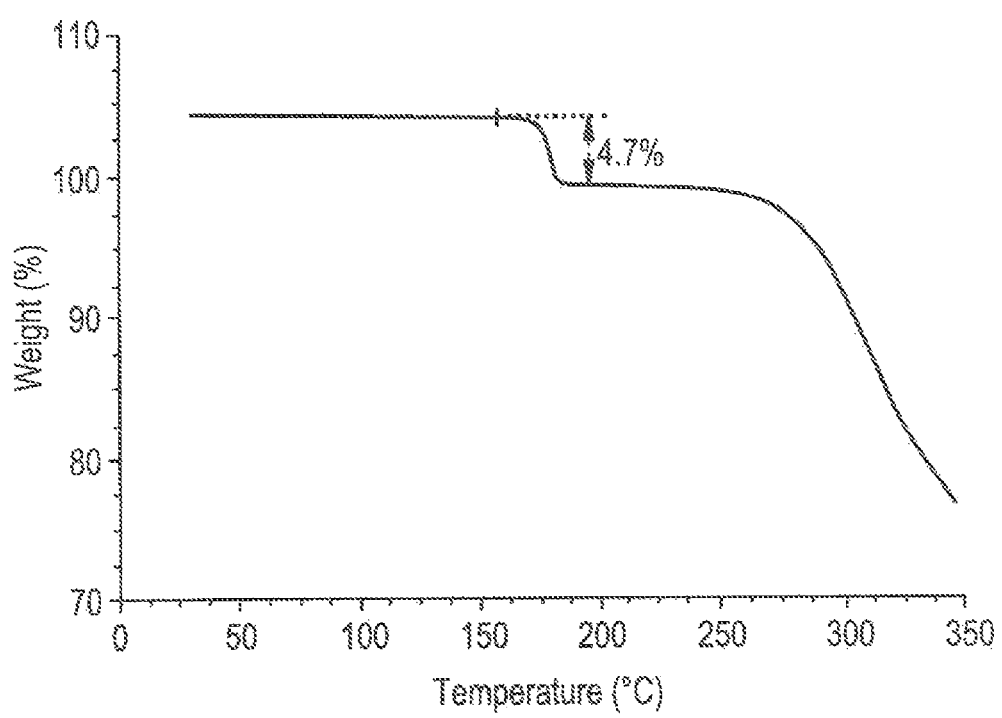
FIGS. 17A-B. (A) TGA of embodiment 11 showing a 4.7% w/w loss between 155° C. and 185° C.; (B) DSC of embodiment 11 showing a first endotherm of 57.8 J/g at 167.8° C. due to solvent loss and a second endotherm of 90.8 J/g at 194.5° C. due to sample melt.
Figure 17B:
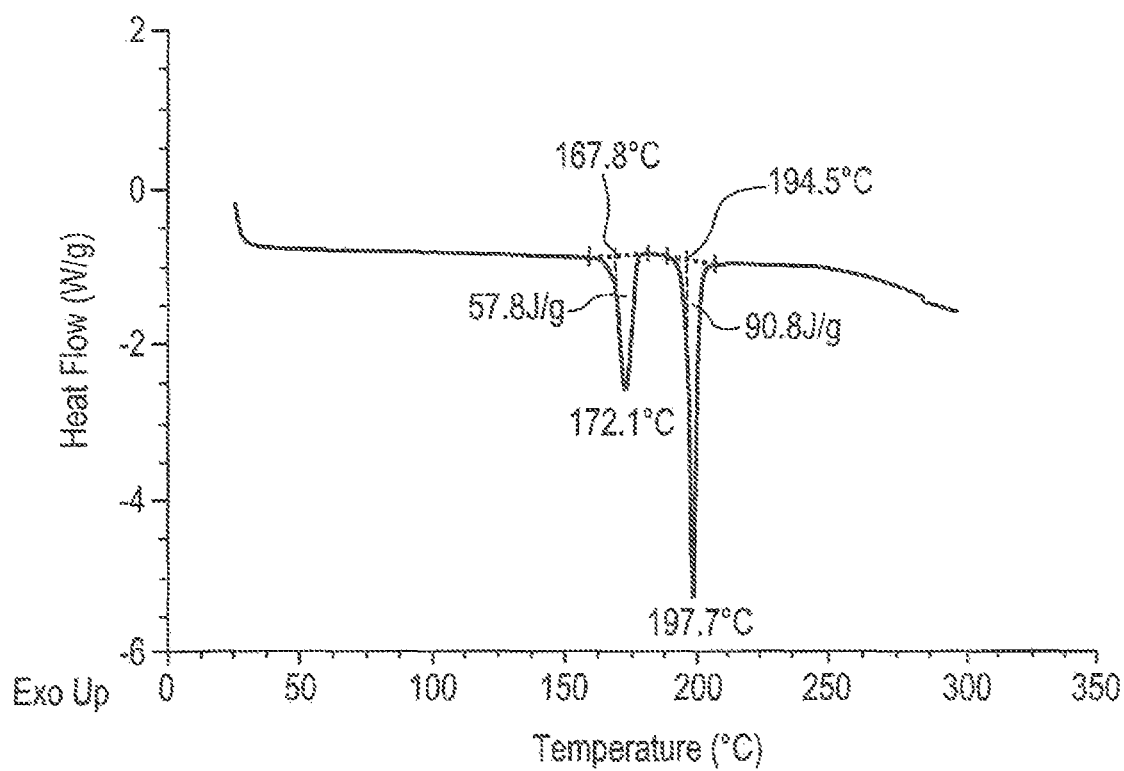

Embodiment 11 was obtained as follows: A suspension of embodiment 1s (45 g) in ethanol (absolute, water content<0.1%, 300 mL) at 50° C. was stirred for 16.5 hours. The suspension was then cooled to 5° C. at 0.25° C./minute. Subsequently, the suspension was stirred at 5° C. for 3 hours. The solids were then filtered off and washed with cold (5° C.) ethanol (absolute, water content<0.1%, 90 mL), and dried under vacuum at 40° C. for 17 hours to yield approximately 39 g of embodiment 11. The TGA and DSC of embodiment 11 is shown in FIGS. 17A and 17B, respectively.

Embodiment 11 was also obtained as follows: Absolute ethanol (170 mL) was added to embodiment 1s (19 g) and heated to about the boiling point of the solvent. A small amount of the solids (5%) did not dissolve and were removed by hot filtration. It was determined that the solids that were filtered off, were embodiment 1s. So the solids were added back into the filtrate and this mixture was heated until all the solids dissolved. To this hot solution was added, heptane (535 mL), drop-wise via a separatory funnel. During this drop-wise addition of heptane, the hot solution was stirred vigorously. After the addition of heptane was complete, the flask containing the hot solution/heptane mixture was submerged in an ice water bath and vigorously stirred for one hour. The solids were then collected by filtration and the white solid filter cake was dried by pulling air through it for 15 minutes. It was further dried by heating it at 70° C. for 16 hours under high vacuum and then by heating it at 80° C. for 18 hours to yield 16.3 g of embodiment 11. The diffractogram for embodiment 11 is shown in FIG. 7.

Figure 18:
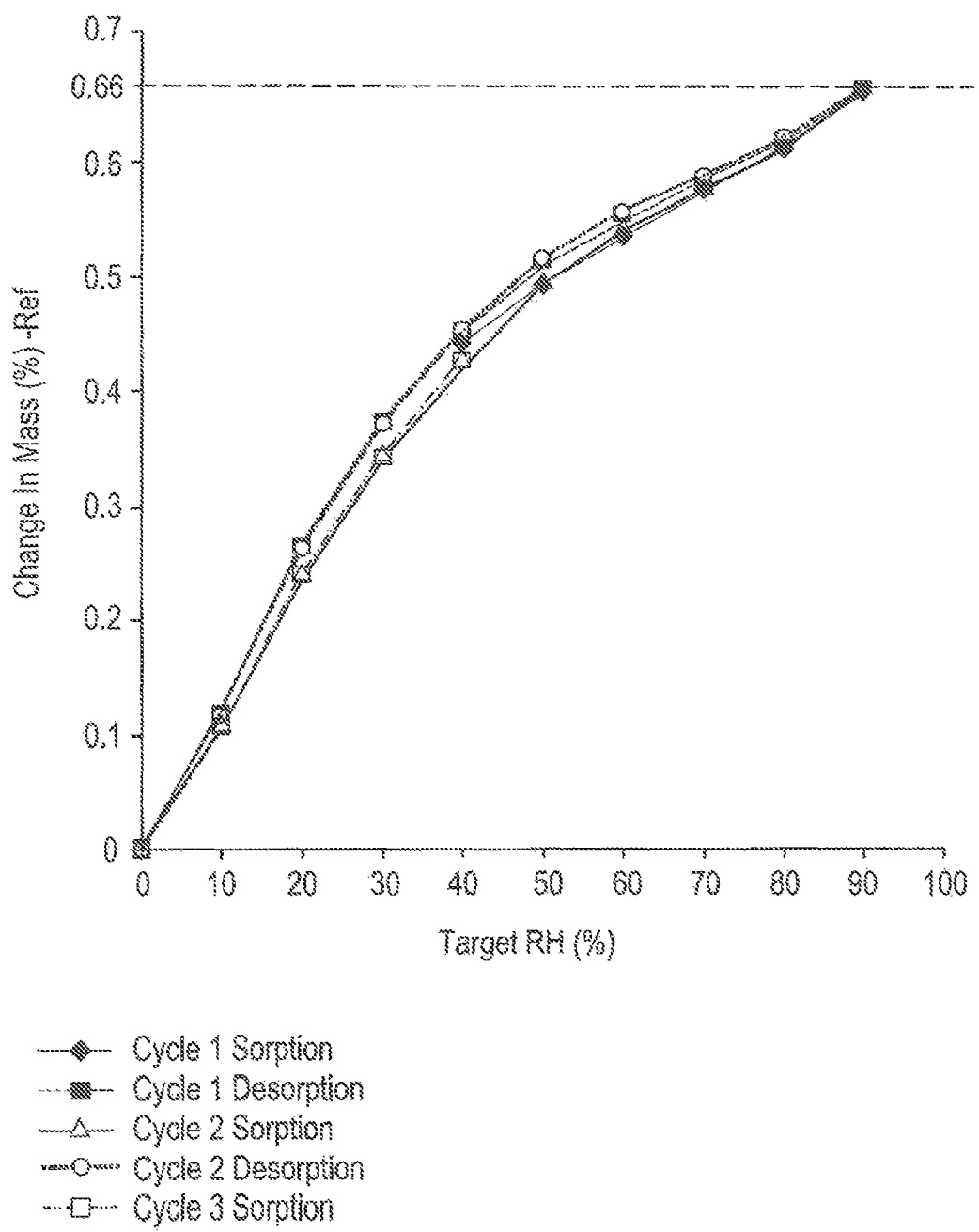
FIG. 18. Gravimetric Vapor Sorption (GVS) isotherm plot of embodiment 11 showing a mass change of 0.66% between 0-90% RH. The mass change on the ordinate axis is in reference to the mass of the starting sample.

In a hygroscopicity study of embodiment 11, it was found it to be only slightly hygroscopic, with a mass change of 0.66% between 0-90% RH in the GVS analysis as shown in FIG. 18. XRPD analysis post GVS analysis showed that the material was physically stable. Variable temperature (VT)-XRPD was performed in order to assess the stability of embodiment 11 upon heating. The material remained unchanged as shown by XRPD analysis when it was subjected to temperatures up to ca. 175° C., however above 180° C. the sample converted to embodiment 6. The diffractograms of embodiment 11 before and after the VT-XRPD experiment, along with the diffractogram for embodiment 6 are shown in FIG. 24. Embodiment 11 was also subjected to static storage analysis at 40° C./75% RH for up to 48 days. The samples were analyzed by XRPD and Karl Fisher (KF) after 2 days, 5 days and 48 days. Embodiment 11 remained unchanged as shown by XRPD analysis with a total water uptake of 1.2% after 48 days. $^1$H-NMR of the material post 48 days static storage showed the material retained 0.36 mol eq of ethanol. Embodiment 11 stored under ambient conditions for the period of the study was shown to contain 0.46 mol eq of ethanol by $^1$H-NMR.

Figure 7A:
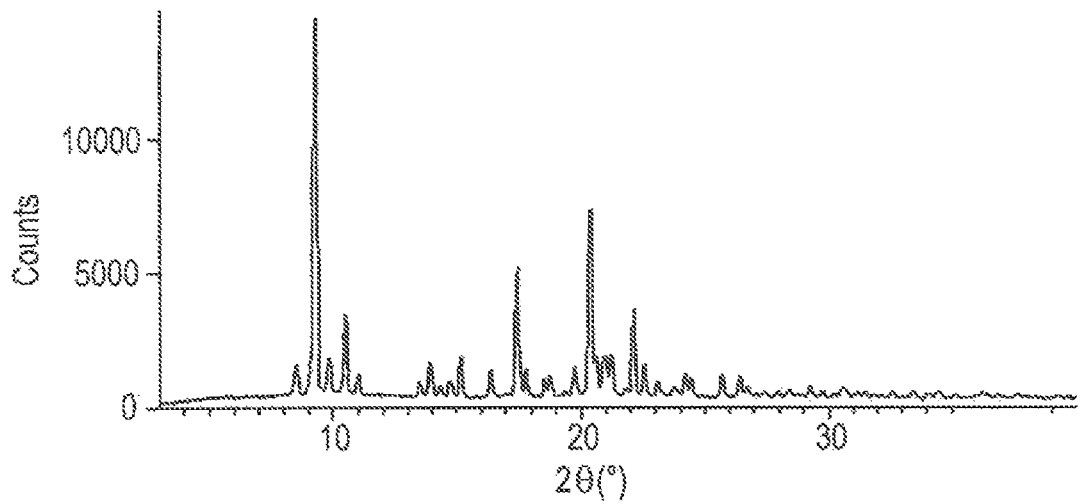
FIGS. 7A-E. X-ray powder diffraction (XRPD) pattern of embodiment 11 (A); embodiment 12 (B); embodiment 13 (C); embodiment 14 (D); and embodiment 11b (E).
Figure 7B:
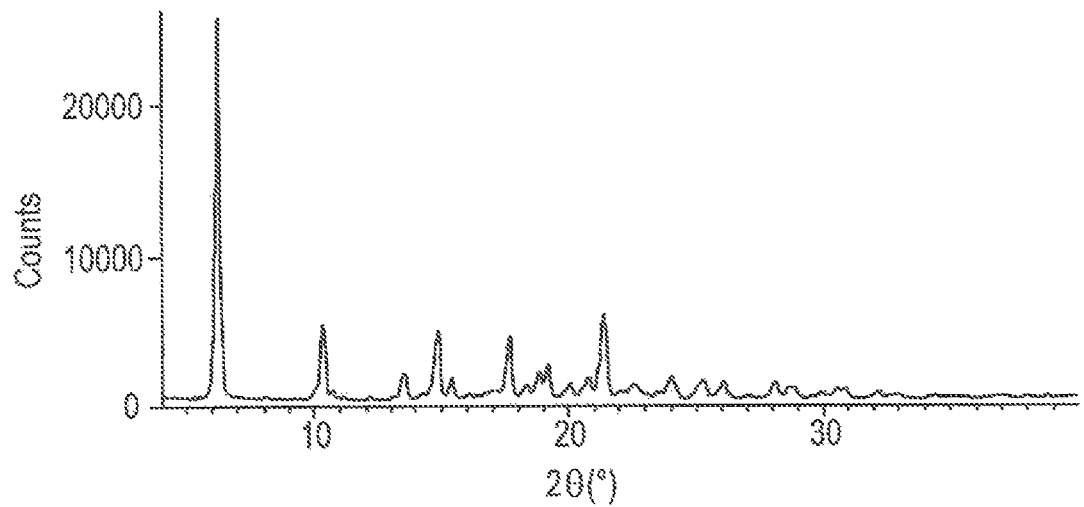
Figure 7C:
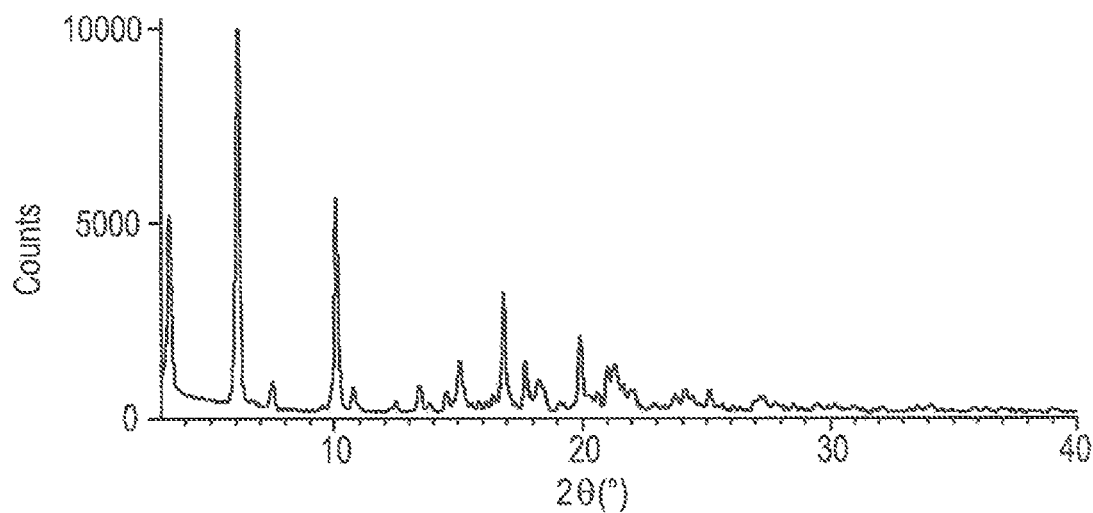
Figure 7D:
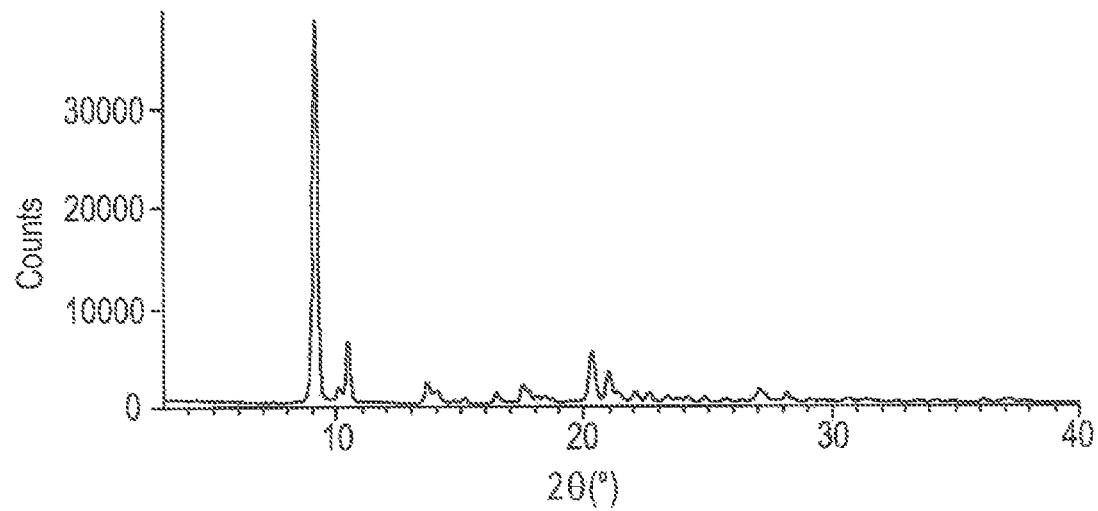
Figure 7E:
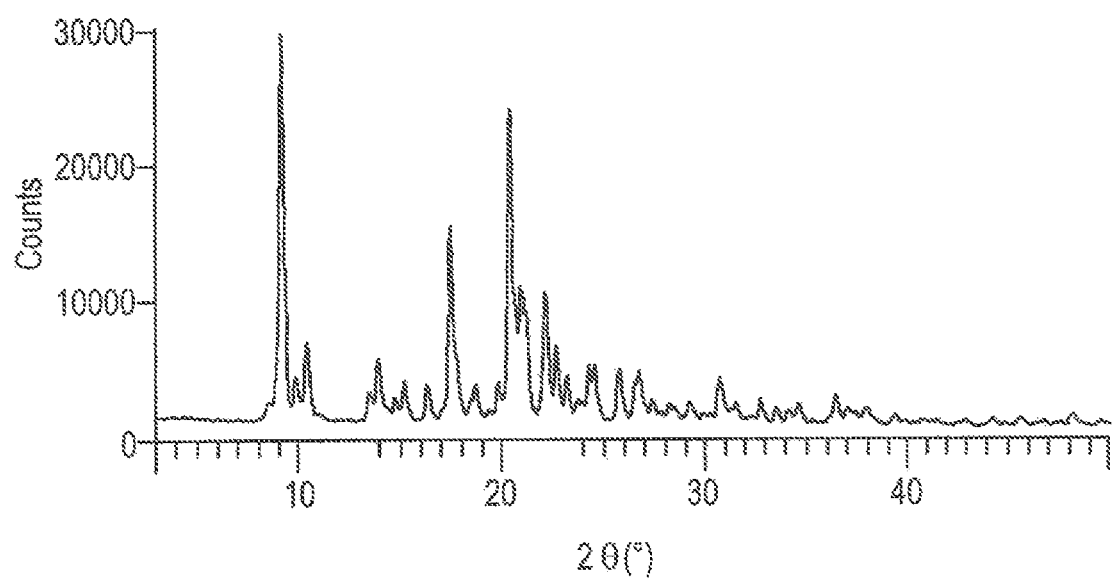

Embodiment 11b was obtained from embodiment 1s as follows: 10 mL of dried methanol was added to 3.3 g of embodiment 1s. This mixture was subjected to the following temperature cycling: The mixture was heated at 40° C. for 1 hour and then the temperature was increased to 60° C. over a 2 hour period. The mixture was then heated at 60° C. for 1 hour. The temperature was then decreased to 40° C. over a 2 hour period. This temperature cycling regime was repeated for a total of about 20 hours. At that time the mixture was cooled to 5° C. over a 2 hour period. The solids were isolated at 5° C. by vacuum filtration and then dried at ambient temperature under vacuum for about 66 hours. Alternatively, embodiment 11b was obtained from embodiment 1s using the following procedure: 1 mL of dried methanol was added to 330 mg of embodiment 1s. This mixture was subjected to the following temperature cycling: The mixture was heated at 40° C. for 1 hour and then the temperature was increased to 60° C. over a 2 hour period. The mixture was then heated at 60° C. for 1 hour. The temperature was then decreased to 40° C. over a 2 hour period. This temperature cycling regime was repeated for a total of about 18 hours. At that time the solids were isolated by centrifugation and then dried at ambient temperature under vacuum for about 33 hours. The methanol for the above experiments was dried using molecular sieves (3 Å, activated at 100° C. under vacuum for at least 24 h). The diffractogram for embodiment 11b is shown in FIG. 7E.

Embodiment 12 was obtained from embodiment 1s, which was exposed to humidity conditions below 10% RH at 25° C. to provide embodiment 12. The diffractogram for embodiment 12 is shown in FIG. 7B.

Embodiment 13 was obtained as follows: To a 250 mL 4-necked flask at 25±5° C. was added a sample of embodiment 1s. The flask was then charged with MeOH (4.0 V, 40 mL) and purified water (10 mL, 1.0 V) and stirred until all the solid dissolved. $N_2$ was bubbled into the mixture for 1 hour and the mixture was then cooled to 0 to 5° C. A 0.225 mL volume of a cooled solution (0 to 5° C.) of $NaBH_4$/water (0.006 eq., 2.5% w/w) was prepared with purified water (40 mL) charged into a 100 mL of a 4-necked flask under $N_2$ at 0° C., followed by the addition of $NaBH_4$ (1.0 g); the mixture was stirred at 0° C. until all the $NaBH_4$ dissolved. Such $NaBH_4$ solution was added into the 250-mL flask that was cooled (0 to 5° C.) and stirred at 0 to 5° C. The color of the reaction mixture changed to yellow. Purified water (40 mL, 4.0 V, degassed with $N_2$ before using) was added dropwise over 1 hour at 0 to 5° C. The reaction was stirred for 4 hours under $N_2$ at 0 to 5° C. Additional purified water (30 mL, 3.0 V, degassed) was added dropwise over 1 hour at 0 to 5° C. and the reaction mixture was stirred for an additional 16 hours under $N_2$ at 0 to 5° C. The reaction was then filtered and the resulting solids were washed with purified water (20 mL, 2 V, degassed with $N_2$ before using) in a glove box environment under $N_2$ ($O_2$ content being 200 ppm). The solids were dried under vacuum with moisturized nitrogen at 35±5° C. to provide embodiment 13 as an off-white solid. The diffractogram for embodiment 13 is shown in FIG. 7C.

Embodiment 14 was prepared as follows: 2-(1-((1r,4r)-4-(cyanomethyl)cyclohexyl)-6-(phenylsulfonyl)-1,6-dihydro-imidazo[4,5-d]pyrrolo[2,3-b]pyridin-2-yl)-N-(2-hydroxy-2-methylpropyl)acetamide (48.15 kg, prepared in Ex. 2, Step B), EtOH (technical grade, 481 L) and KOH (6.613 kg) were stirred at 10-20° C. for 9 hours. The reaction was then quenched with acetic acid (6.74 L) maintaining the temperature at 10-20° C. Acetonitrile (240 L) was added and the solvents were evaporated under reduced pressure to a volume of about 240 L. This addition and evaporation of acetonitrile was repeated two more times. The resulting mixture was heated to 60-70° C. for 5 hours after which it was cooled to 10-15° C. and stirred for 2 h. The solids in this mixture were then filtered off and washed with acetonitrile (48 L) twice. The solids were then added to water (240 L) and the reaction mixture heated to 45-50° C. for 3-5 hours followed by cooling to 15-20° C. for 4 hours. The solids remaining were filtered off and the filter cake was washed with water (96 L, two times). This filter cake was dried at 45° C. to provide embodiment 14 (26.28 kg). The diffractogram for embodiment 14 is shown in FIG. 7D.

Additional embodiments of compound of Formula I were obtained as described below.

Solubility Assessment

Figure 8:
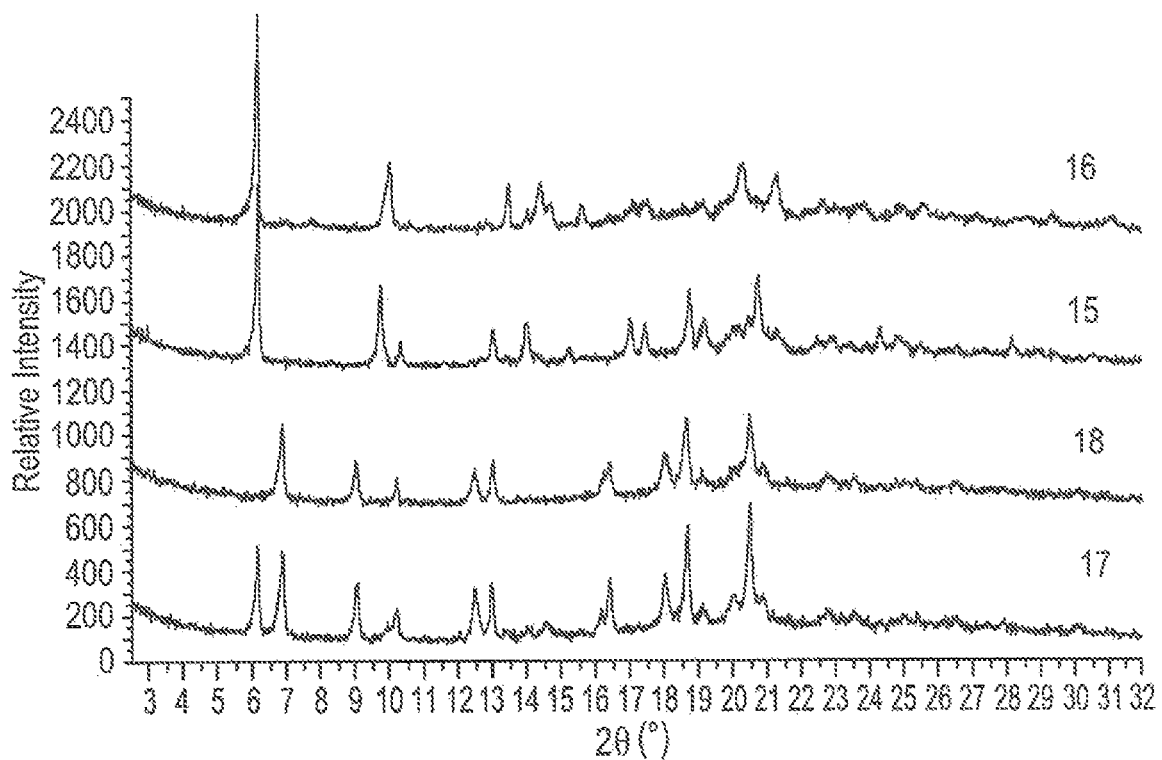
FIG. 8. Overlay of X-ray powder diffraction (XRPD) patterns for the following embodiments of compound of Formula I, from bottom to top: embodiment 17, embodiment 18, embodiment 15 and embodiment 16.
Figure 9:
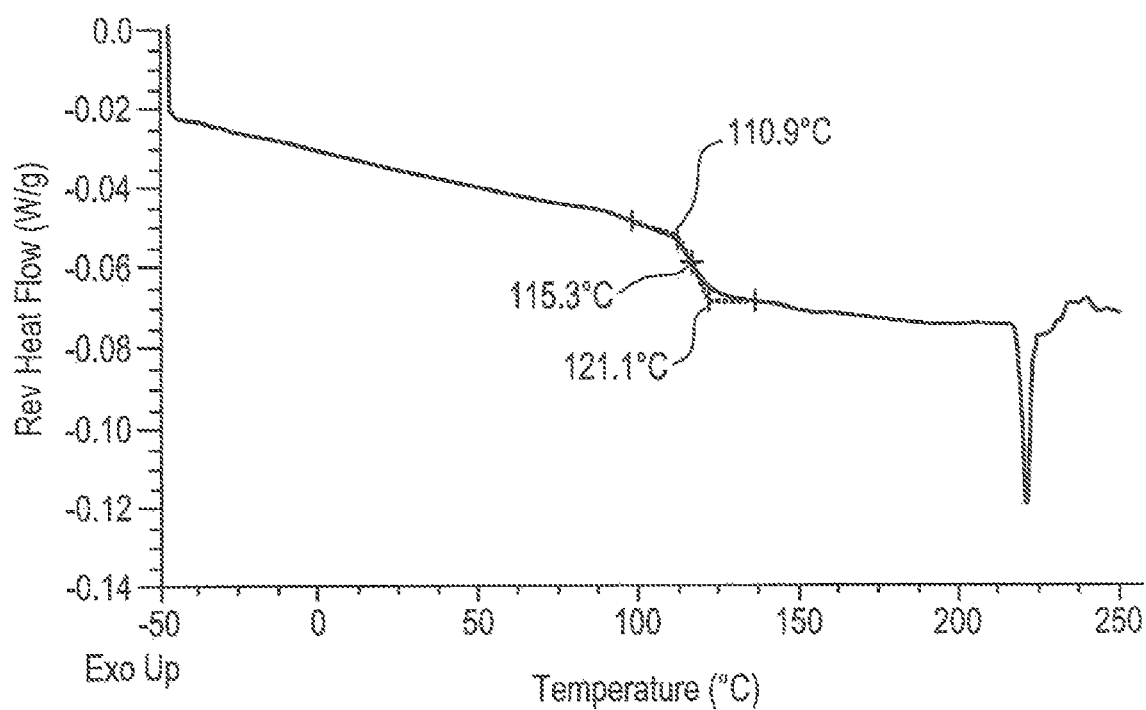
FIG. 9. Modulated DSC ("mDSC") profile for embodiment 19 showing a glass transition point ($T_g$) at 115.3° C. ("Rev" in the ordinate axis label refers to "reversible").
Figure 10A:
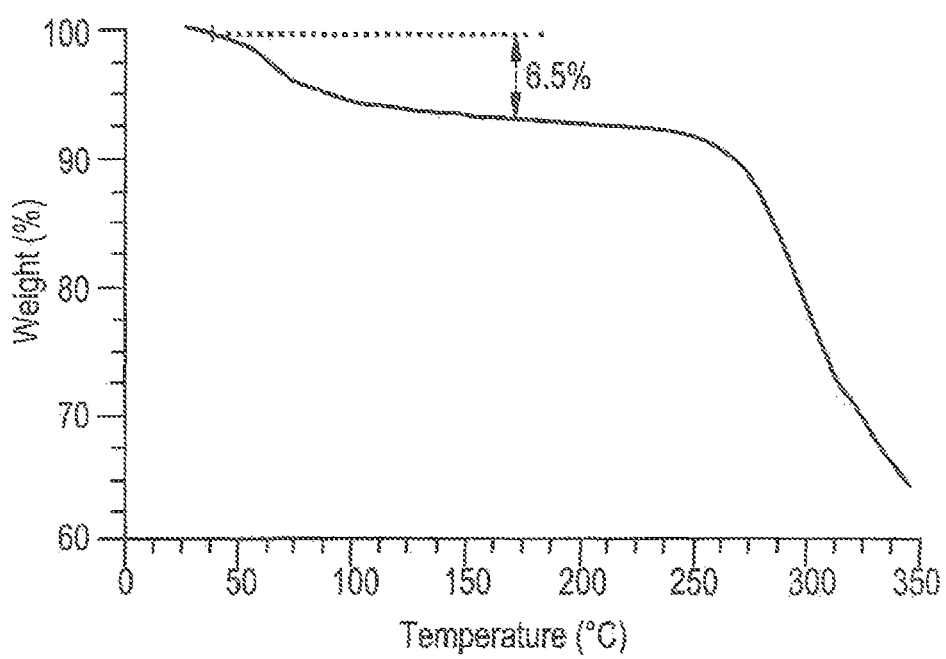
FIGS. 10A-B. (A) TGA (thermogravimeteric analysis) of embodiment 18 showing a 6.5 w/w loss between 30° C. and 170° C.; (B) DSC (differential scanning calorimetry) of embodiment 18 showing an endotherm of 52.8 J/g between 45° C. and 90° C., an endotherm of 31.0 J/g at 140.6° C., an exotherm of 24.3 J/g at 168.8° C., and an endotherm of 31.3 J/g at 200.0° C.
Figure 10B:
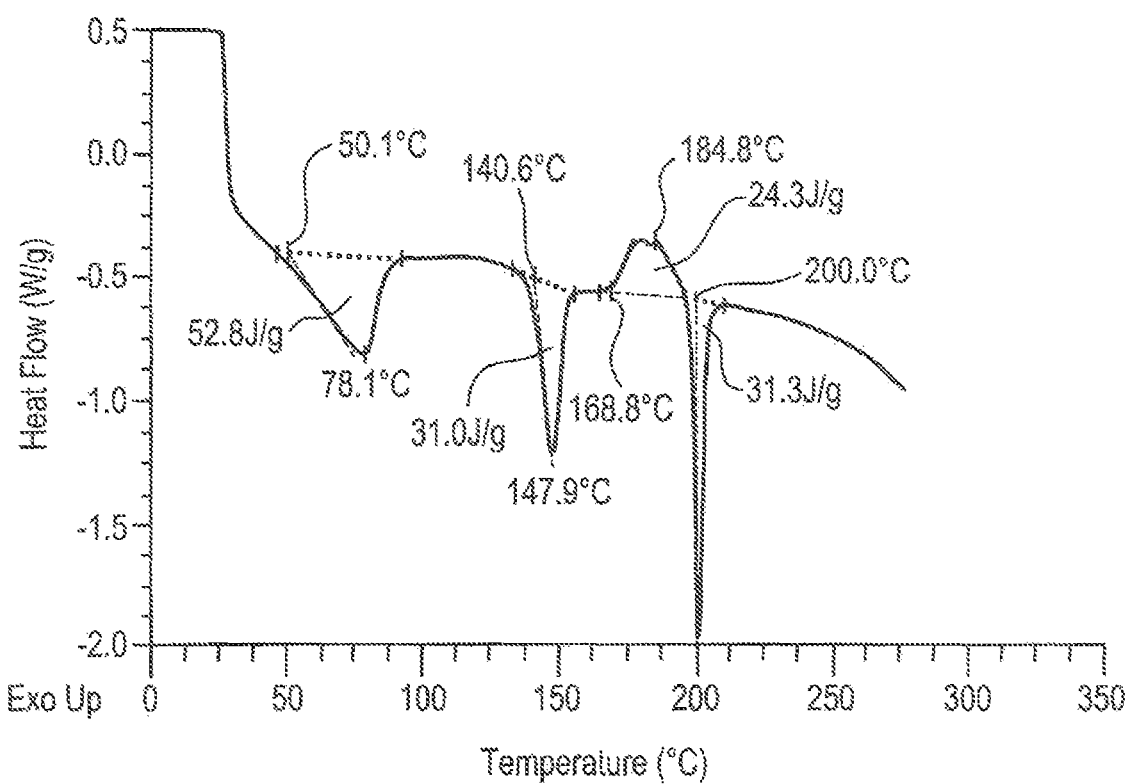
Figure 11:
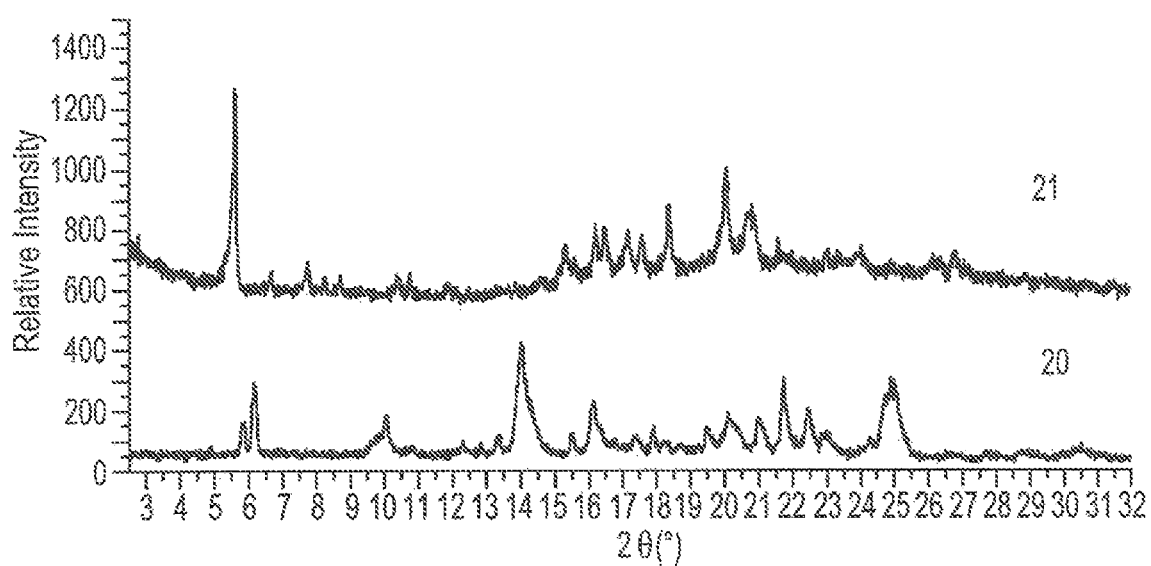
FIG. 11. Overlay of X-ray powder diffraction (XRPD) patterns for the following embodiments of compound of Formula I, from bottom to top: embodiment 20 and embodiment 21.
Figure 12A:
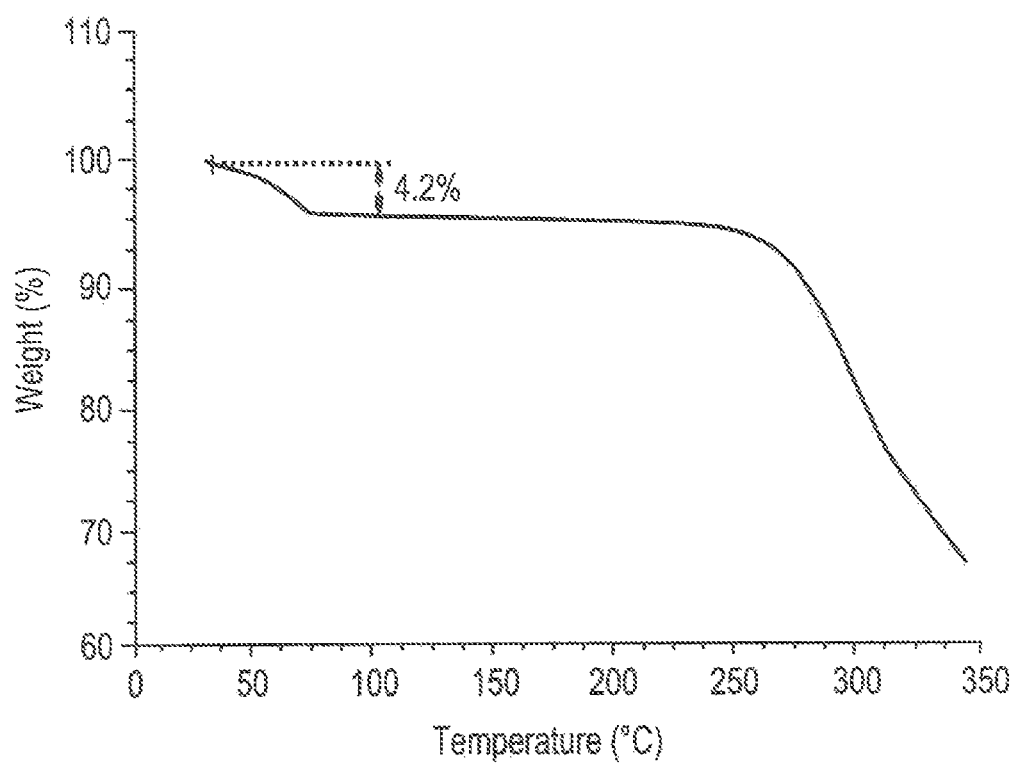
FIGS. 12A-B. (A) TGA of embodiment 17 showing a 4.2% w/w loss between 30° C. and 100° C.; (B) DSC of embodiment 17 showing an endotherm of 90.3 J/g between 45° C. and 100° C., an endotherm of 35.5 J/g at 143.8° C., an endotherm of 1.6 J/g at 168.3° C., an exotherm of 3.8 J/g at 178° C., and an endotherm of 9.2 J/g at 200.0° C.
Figure 12B:
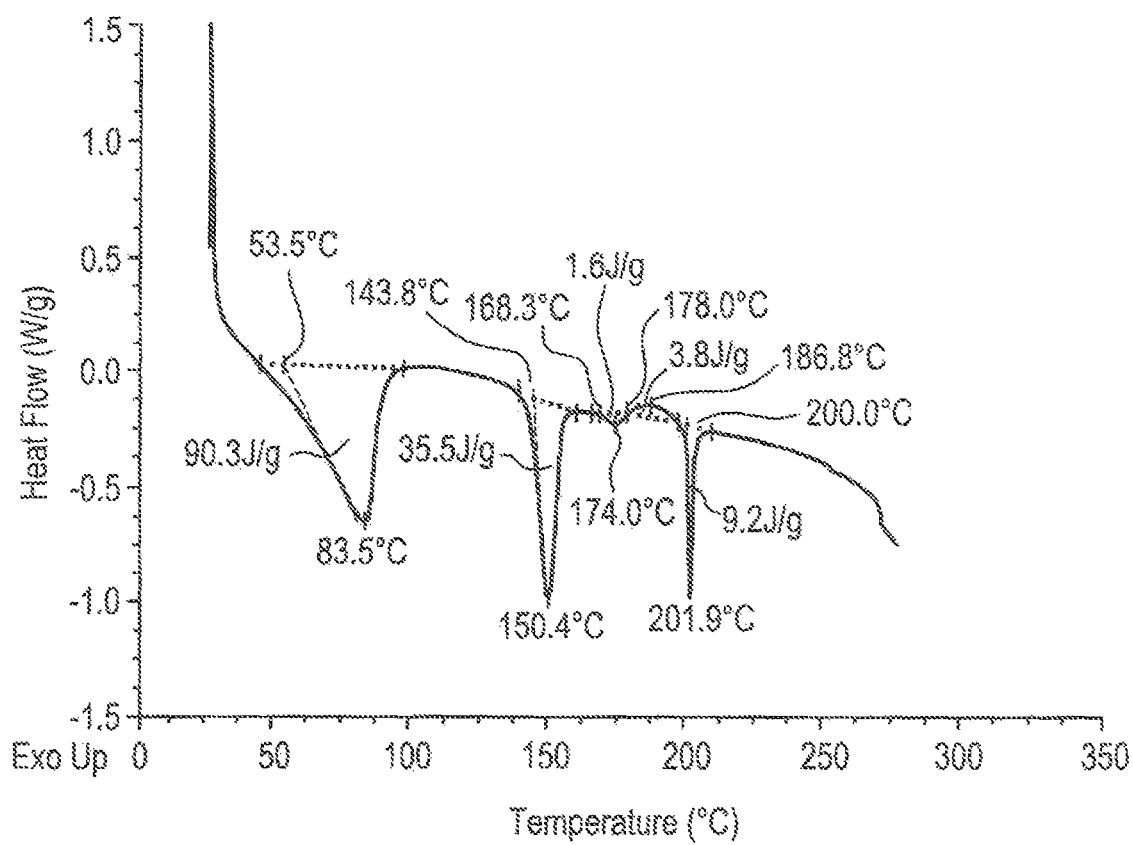

Embodiment 1s (15 mg) was treated with increasing volume of solvent until the material fully dissolved or until a maximum of 100 mL of solvent had been added. The solvent was added in the following increments: 5 mL, 10 mL, 20 mL, 30 mL, 40 mL, 50 mL, 70 mL and 100 mL. After each addition of solvent, the system was held at 50° C. for 5 min with gentle stirring and visually assessed for presence of solid. This process continued until a total of 100 mL of solvent had been added. If no solid remained, then no additional solvent was added. After the assessment was completed, the solution was held at 50° C. for 1 h and then cooled from 50° C. to 5° C. at 0.1° C./min with stirring. If solid was present, then the mixture was filtered under vacuum using a 96 well plate and analyzed by XRPD. If a clear solution was obtained, the solution was left to evaporate at RT. The following solvents, where total amount added is noted in parenthesis immediately after the solvent, at temperatures of 5° C. and 50° C. were used according to this procedure, where the dissolution extent is given within parenthesis after each temperature which yielded the noted embodiment: Water (100 mL) at 5° C. (suspension) and 50° C. (suspension), yielded embodiment 1s whose diffractogram is shown in FIG. 5; methanol (10 mL) at 5° C. (suspension) and at 50° C. (solution), yielded embodiment 1s whose diffractogram is shown in FIG. 5; ethanol (30 mL) at 5° C. (suspension) and at 50° C. (solution), yielded embodiment 1s whose diffractogram is shown in FIG. 5; 2-propanol (30 mL) at 5° C. (suspension) and at 50° C. (solution), yielded embodiment 1s whose diffractogram is shown in FIG. 5; 1-propanol (30 mL) at 5° C. (suspension) and at 50° C. (solution), yielded embodiment 1s whose diffractogram is shown in FIG. 5; acetone (100 mL) at 5° C. (suspension) and at 50° C. (solution), yielded embodiment 1s whose diffractogram is shown in FIG. 5; ethyl acetate (100 mL) at 5° C. (suspension) and at 50° C. (turbid), yielded embodiment 1s whose diffractogram is shown in FIG. 5; acetonitrile (100 mL) at 5° C. (suspension) and at 50° C. (solution), yielded embodiment 6 whose diffractogram is shown in FIG. 3; toluene (100 mL) at 5° C. (partially dissolved) and at 50° C. (turbid), yielded embodiment 1s whose diffractogram is shown in FIG. 5; isopropyl acetate (100 mL) at 5° C. (suspension) and at 50° C. (turbid), yielded embodiment 1s whose diffractogram is shown in FIG. 5; methyl t-butyl ether (100 mL) at 5° C. (suspension) and at 50° C. (suspension), yielded embodiment 1s whose diffractogram is shown in FIG. 5; 2-butanone (100 mL) at 5° C. (suspension) and at 50° C. (solution), yielded embodiment 1s whose diffractogram is shown in FIG. 5; THF (70 mL) at 5° C. (partially dissolved) and at 50° C. (solution), yielded embodiment 1s whose diffractogram is shown in FIG. 5; DMSO (5 mL) at 5° C. (solution, sample was frozen and left to evaporate at RT) and at 50° C. (solution), yielded embodiment 1s whose diffractogram is shown in FIG. 5; N-methyl pyrrolidinone (5 mL) at 5° C. (solution, left to evaporate at RT) and at 50° C. (solution), yielded embodiment 1s whose diffractogram is shown in FIG. 5; diethyl ether (100 mL) at 5° C. (suspension) and at 50° C. (suspension), yielded embodiment 1s whose diffractogram is shown in FIG. 5; methyl isobutyl ketone (100 mL) at 5° C. (suspension) and at 50° C. (suspension), yielded embodiment 1s whose diffractogram is shown in FIG. 5; DCM (100 mL) at 5° C. (suspension) and at 50° C. (suspension), yielded embodiment 1s whose diffractogram is shown in FIG. 5; heptane (100 mL) at 5° C. (suspension) and at 50° C. (suspension), yielded embodiment 18 whose diffractogram is shown in FIG. 8; 1-4-dioxane (100 mL) at 5° C. (partially dissolved, sample was frozen and left to evaporate at RT) and at 50° C. (suspension), yielded in dried form embodiment 3c whose diffractogram is shown in FIG. 5; nitromethane (100 mL) at 5° C. (suspension) and at 50° C. (suspension), yielded a poorly crystalline embodiment (diffractogram not shown); 1-methoxy-2-propanol (20 mL) at 5° C. (solution) and at 50° C. (solution), yielded in dried form embodiment 20 whose diffractogram is shown in FIG. 11; 2-methyl-THF (100 mL) at 5° C. (suspension) and at 50° C. (suspension), yielded embodiment 18 whose diffractogram is shown in FIG. 8 and whose TGA and DSC is shown in FIGS. 10A and 10B, respectively; tetralin (100 mL) at 5° C. (suspension) and at 50° C. (turbid), yielded a mixture of embodiment 4 and embodiment 1b whose diffractogram is shown in FIG. 3; 3-methyl-1-butanol (100 mL) at 5° C. (suspension) and at 50° C. (solution), yielded embodiment 17 whose diffractogram is shown in FIG. 8 and whose TGA and DSC is shown in FIGS. 12A and 12B, respectively; anisole (100 mL) at 5° C. (suspension) and at 50° C. (turbid), yielded a mixture of embodiment 4 and embodiment 1b whose diffractogram is shown in FIG. 3; t-butanol/water (1:1, 10 mL) at 5° C. (solution) and at 50° C. (solution), yielded in dried form an embodiment 19 whose modulated DSC is shown in FIG. 9; 1,2-dimethoxyethane (100 mL) at 5° C. (suspension) and at 50° C. (turbid), yielded a mixture of embodiment 4 and embodiment 1b whose diffractogram is shown in FIG. 3; cumene (100 mL) at 5° C. (suspension) and at 50° C. (turbid), yielded a mixture of embodiment 4 and embodiment 1b whose diffractogram is shown in FIG. 3; diisopropyl ether (100 mL) at 5° C. (suspension) and at 50° C. (suspension), yielded embodiment 18 whose diffractogram is shown in FIG. 8; morpholine (5 mL) at 5° C. (suspension) and at 50° C. (solution), yielded in dried form embodiment 21 whose diffractogram is shown in FIG. 11; ethanol:water (95:5, 10 mL) at 5° C. (suspension) and at 50° C. (solution), yielded a poorly crystalline embodiment (diffractogram not shown); ethanol:water (9:1, 5 mL) at 5° C. (solution) and at 50° C. (solution), yielded in dried form embodiment 1s whose diffractogram is shown in FIG. 5; and acetonitrile:water (95:5, 30 mL) at 5° C. (suspension) and at 50° C. (solution), yielded a poorly crystalline embodiment (diffractogram not shown).

Incubation at 5° C.

Several experiments of incubation at 5° C. were performed by treating embodiment 1s (30 mg) with each solvent, and the mixture was slurried at 5° C. for 48 h. An aliquot was taken and immediately analyzed by XRPD. Each aliquot dried for 16 h and was re-analyzed by XRPD. The air-dried samples were then placed in a vacuum oven (RT) for 24 h before further analysis by XRPD. The following solvents, where total solvent amount added is noted in parenthesis immediately after the solvent followed by dissolution extent, were used according to this procedure which yielded the noted embodiment: Water (30 mL, suspension), yielded embodiment 1s whose diffractogram is shown in FIG. 5; methanol (5 mL, suspension), yielded embodiment 1s whose diffractogram is shown in FIG. 5; ethanol (30 mL, suspension), yielded embodiment 1s whose diffractogram is shown in FIG. 5; 2-propanol (30 mL, suspension), yielded embodiment 1s whose diffractogram is shown in FIG. 5; 1-propanol (30 mL, suspension), yielded embodiment 1s whose diffractogram is shown in FIG. 5; acetone (30 mL, suspension), yielded embodiment 1s whose diffractogram is shown in FIG. 5; ethyl acetate (30 mL, suspension), yielded embodiment 1s whose diffractogram is shown in FIG. 5; acetonitrile (30 mL, suspension), yielded a poorly crystalline embodiment (diffractogram not shown); toluene (30 mL, suspension), yielded embodiment 15 whose diffractogram is shown in FIG. 8; isopropyl acetate (30 mL, suspension), yielded embodiment 17 whose diffractogram is shown in FIG. 8; methyl t-butyl ether (30 mL, suspension), yielded embodiment 18 whose diffractogram is shown in FIG. 8; 2-butanone (30 mL, suspension), yielded embodiment 1s whose diffractogram is shown in FIG. 5; THF (30 mL, suspension), yielded embodiment 17 whose diffractogram is shown in FIG. 8; diethyl ether (30 mL, suspension), yielded embodiment 1s whose diffractogram is shown in FIG. 5; methyl isobutyl ketone (30 mL, suspension), yielded embodiment 17 whose diffractogram is shown in FIG. 8; DCM (30 mL, suspension), yielded embodiment 1s whose diffractogram is shown in FIG. 5; heptane (30 mL, suspension), yielded embodiment 1s whose diffractogram is shown in FIG. 5; 1,4-dioxane (30 mL, suspension), yielded embodiment 3c whose diffractogram from this experiment is shown in FIG. 5; nitromethane (30 mL, suspension), yielded a poorly crystalline form embodiment 1s whose diffractogram is not shown; propylene glycol (30 mL, suspension), yielded a poorly crystalline embodiment (diffractogram not shown); 2-methyl-tetrahydrofuran (30 mL, suspension), yielded embodiment 18 whose diffractogram is shown in FIG. 8; tetralin (30 mL, suspension), yielded a poorly crystalline embodiment 1s whose diffractogram is not shown; 3-methyl-1-butanol (30 mL, suspension), yielded embodiment 18 whose diffractogram is shown in FIG. 8; anisole (30 mL, suspension), yielded embodiment 1s with an whose diffractogram is similar to that of embodiment 1s (as shown in FIG. 5) except that it displays some additional peaks; 1,2-dimethoxyethane (30 mL, suspension), yielded embodiment 1s with an whose diffractogram is similar to that of embodiment 1s (as shown in FIG. 5) except that it displays some additional peaks; cumene (30 mL, suspension), yielded embodiment 1s with an whose diffractogram is similar to that of embodiment 1s (as shown in FIG. 5) except that it displays some additional peaks; diisopropyl ether (30 mL, suspension), yielded embodiment 17 whose diffractogram is shown in FIG. 8; ethanol:water (95:5, 30 mL, suspension), yielded embodiment 1s whose diffractogram is shown in FIG. 5; acetonitrile:water (95:5, 30 mL, suspension), yielded a poorly crystalline embodiment (diffractogram not shown); and polyethylene glycol (30 mL, suspension), yielded a poorly crystalline embodiment (diffractogram not shown).

Heat/Cool Maturation

Figure 13:
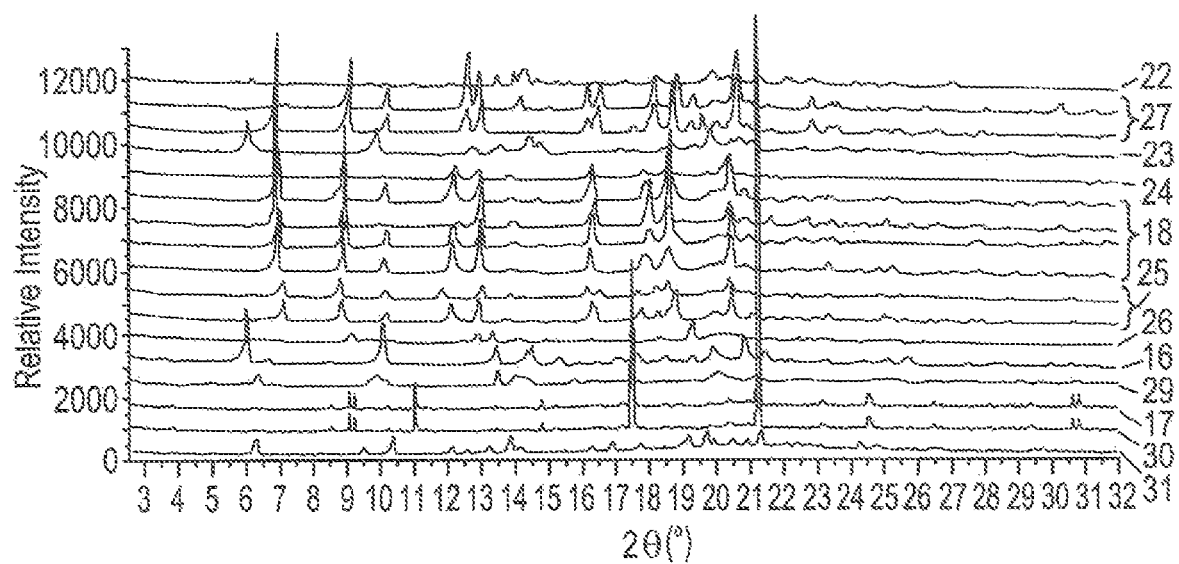
FIG. 13. Overlay of X-ray powder diffraction (XRPD) patterns for the following embodiments of compound of Formula I, from bottom to top: embodiment 31, embodiment 30, embodiment 17, embodiment 29, embodiment 16, embodiment 26, embodiment 25, embodiment 18, embodiment 24, embodiment 23, embodiment 27 and embodiment 22.

A suspension of embodiment 1s (30 mg) in each solvent was placed in a platform shaker incubator and subjected to a series of heat-cool cycles from ambient to approximately 50° C. for 24 h. This was achieved by switching the heating on and off every 4 hours. Shaking was maintained throughout. An aliquot from each sample was taken and allowed to air-dry for 2 h. The air-dried solids were analyzed by XRPD, then vacuum dried using a vacuum oven (RT, 24 h) and were re-analyzed by XRPD. Each sample obtained in this experiment was vacuum dried and after vacuum drying each sample was analyzed by XRPD incubation at elevated temperature. The following solvents, where total solvent amount added is noted in parenthesis immediately after the solvent, were used according to this procedure which yielded the noted embodiment: Water (20 mL) yielded embodiment 1s whose diffractogram is shown in FIG. 5; methanol (5 mL) yielded embodiment 22 whose diffractogram is shown in FIG. 13; ethanol (5 mL) yielded embodiment 1s whose diffractogram is shown in FIG. 5; 2-propanol (10 mL) yielded embodiment 27 whose diffractogram for this experiment is shown in FIG. 13; 1-propanol (10 mL) yielded embodiment 23 whose diffractogram is shown in FIG. 13; acetone (20 mL) yielded embodiment 1s whose diffractogram is shown in FIG. 5; ethyl acetate (20 mL) yielded a poorly crystalline form of embodiment 1s whose diffractogram is not shown; acetonitrile (20 mL) yielded a poorly crystalline embodiment 24 whose diffractogram is shown in FIG. 13; toluene (20 mL) yielded a poorly crystalline embodiment 1s whose diffractogram is not shown; isopropyl acetate (20 mL) yielded embodiment 18 whose diffractogram is shown in FIG. 13; methyl t-butyl ether (20 mL) yielded a poorly crystalline embodiment 1s whose diffractogram is not shown; 2-butanone (20 mL) yielded embodiment 26 whose diffractogram is shown in FIG. 13; THF (20 mL) yielded embodiment 18 whose diffractogram is shown in FIG. 13; diethyl ether (20 mL) yielded a poorly crystalline embodiment 1s whose diffractogram is not shown; methyl isobutyl ketone (20 mL) yielded embodiment 25 whose diffractogram is shown in FIG. 13; DCM (20 mL) yielded a poorly crystalline form of embodiment 1s whose diffractogram is not shown; heptane (20 mL) yielded embodiment 1s whose diffractogram is shown in FIG. 5; 1,4-dioxane (20 mL) yielded embodiment 27 whose diffractogram for this experiment is shown in FIG. 13; nitromethane (20 mL) yielded a poorly crystalline embodiment 1s whose diffractogram is not shown; propylene glycol (5 mL) yielded a poorly crystalline embodiment (diffractogram not shown); 2-methyl-tetrahydrofuran (20 mL) yielded embodiment 18 whose diffractogram is shown in FIG. 13; tetralin (20 mL) yielded embodiment 1s whose diffractogram is shown in FIG. 5; 3-methyl-butanol (20 mL) yielded embodiment 18 whose diffractogram is shown in FIG. 13; anisole (20 mL) yielded embodiment 16 whose diffractogram is shown in FIG. 13 and whose TGA and DSC are shown in FIGS. 23A and 23B, respectively; 1,2-dimethoxyethane (20 mL) yielded embodiment 29 whose diffractogram is shown in FIG. 13; cumene (20 mL) yielded embodiment 1s whose diffractogram is shown in FIG. 5; diisopropyl ether (20 mL) yielded embodiment 17 whose diffractogram is shown in FIG. 13; ethanol:water (95:5, 20 mL) yielded embodiment 30 whose diffractogram is shown in FIG. 13; acetonitrile:water (95:5, 20 mL) yielded a poorly crystalline form of embodiment 1s whose diffractogram is not shown; and polyethylene glycol (5 mL) yielded embodiment 31 whose diffractogram is shown in FIG. 13.

Incubation of Embodiment 1s at 60° C.

Figure 14:
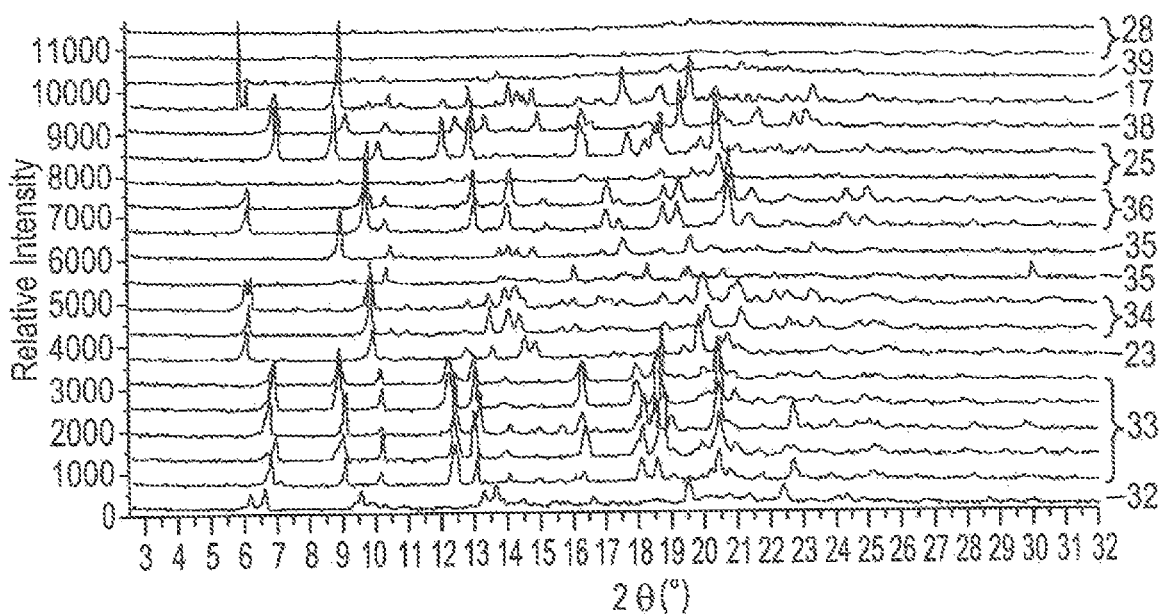
FIG. 14. Overlay of X-ray powder diffraction (XRPD) patterns for the following embodiments of compound of Formula I, from bottom to top: embodiment 32, embodiment 33, embodiment 23, embodiment 34, embodiment 35, embodiment 36, embodiment 25, embodiment 38, embodiment 17, embodiment 39 and embodiment 28.

Embodiment 1s (30 mg) was treated with solvent and shaken at 60° C. for 24 h. An aliquot was taken out and allowed to air-dry for 16 h. The dried samples were then analyzed by XRPD. The following solvents, where total solvent amount added is noted in parenthesis immediately after the solvent, were used according to this procedure which yielded the noted embodiment: Water (10 mL) yielded embodiment 1s whose diffractogram is shown in FIG. 5; ethanol (10 mL) yielded embodiment 32 whose diffractogram is shown in FIG. 14; 2-propanol (10 mL) yielded embodiment 33 whose diffractogram is shown in FIG. 14; 1-propanol (10 mL) yielded embodiment 23 whose diffractogram is shown in FIG. 14; acetone (10 mL) yielded embodiment 1s whose diffractogram is shown in FIG. 5; ethyl acetate (10 mL) yielded embodiment 34 whose diffractogram is shown in FIG. 14; acetonitrile (10 mL) yielded embodiment 35 whose diffractogram is shown in FIG. 14; toluene (10 mL) yielded embodiment 36 whose diffractogram is shown in FIG. 14; isopropyl acetate (10 mL) yielded embodiment 25 whose diffractogram for this experiment is shown in FIG. 14; methyl t-butyl ether (10 mL) yielded embodiment 35 whose diffractogram is shown in FIG. 14; 2-butanone (10 mL) yielded embodiment 38 whose diffractogram is shown in FIG. 14; THF (10 mL) yielded embodiment 33 whose diffractogram for this experiment is shown in FIG. 14; diethyl ether (10 mL) yielded embodiment 1s whose diffractogram is shown in FIG. 5; methyl isobutyl ketone (10 mL) yielded embodiment 25 whose diffractogram for this experiment is shown in FIG. 14; DCM (10 mL) yielded embodiment 1s whose diffractogram is shown in FIG. 5; heptane (10 mL) yielded embodiment 1s whose diffractogram is shown in FIG. 5; 1-4-dioxane (10 mL) yielded embodiment 33 whose diffractogram is shown in FIG. 14; nitromethane (10 mL) yielded embodiment 1s whose diffractogram is shown in FIG. 5; propylene glycol (10 mL) yielded embodiment 28 whose diffractogram for this experiment is shown in FIG. 14; 2-methyl-tetrahydrofuran (10 mL) yielded embodiment 33 whose diffractogram is shown in FIG. 14; tetralin (10 mL) yielded a mixture (diffractogram of the mixture not shown) of embodiment 1s whose diffractogram is shown in FIG. 5 and embodiment 19 whose modulated DSC profile is shown in FIG. 9; 3-methyl-1-butanol (10 mL) yielded embodiment 33 whose diffractogram is shown in FIG. 14; anisole (10 mL) yielded embodiment 36 whose diffractogram is shown in FIG. 14; 1,2-dimethoxyethane (10 mL) yielded embodiment 34 whose diffractogram is shown in FIG. 14; cumene (10 mL) yielded embodiment 1s whose diffractogram is shown in FIG. 5; diisopropyl ether (10 mL) yielded embodiment 17 whose diffractogram is shown in FIG. 8; ethanol:water (95:5, 10 mL) yielded embodiment 28 whose diffractogram is shown in FIG. 14; and polyethylene glycol (5 mL) yielded embodiment 39 whose diffractogram for this experiment is shown in FIG. 14

High Temperature Maturation

Figure 15:
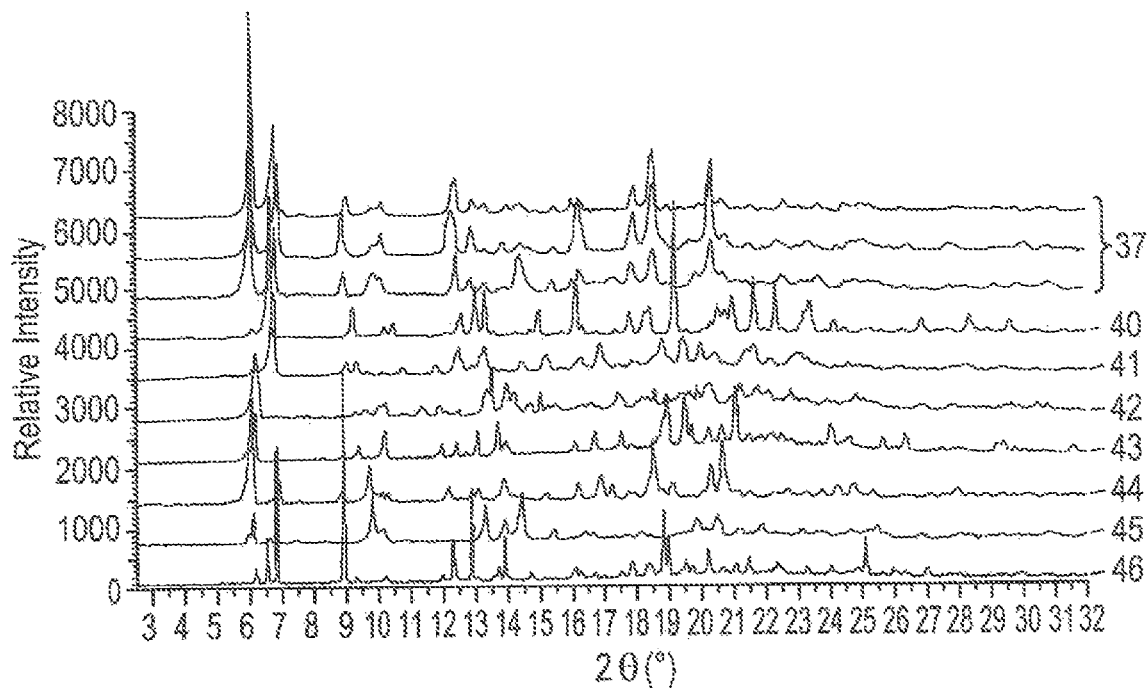
FIG. 15. Overlay of X-ray powder diffraction (XRPD) patterns for the following embodiments of compound of Formula I, from bottom to top: embodiment 46, embodiment 45, embodiment 44, embodiment 43, embodiment 42, embodiment 41, embodiment 40 and embodiment 37.

Each of a plurality of embodiment 19 (25 mg) samples was treated with an amount of a solvent as indicated below yielding in turn a plurality of samples, each agitated at 60° C. for 24 h. Solids from each sample were isolated, air-dried for 16 h and analyzed by XRPD. The following solvents, where total solvent amount added is noted in parenthesis immediately after the solvent followed by dissolution extent, were used according to this procedure which yielded the noted embodiment: Water (125 µL, suspension) yielded embodiment 1s whose diffractogram is shown in FIG. 5; methanol (125 µL, suspension) yielded embodiment 1s whose diffractogram is similar to the diffractogram for embodiment 1s shown in FIG. 5 except it displays some additional peaks; ethanol (125 µL, suspension) yielded embodiment 1s whose diffractogram is shown in FIG. 5; 2-propanol (75 µL, suspension) yielded embodiment 37 whose diffractogram is shown in FIG. 15; 1-propanol (75 µL, suspension) yielded embodiment 40 whose diffractogram is shown in FIG. 15; acetone (75 µL, suspension) yielded embodiment 1s whose diffractogram is shown in FIG. 5; ethyl acetate (75 µL, suspension) yielded embodiment 1s whose diffractogram is shown in FIG. 5; acetonitrile (75 µL, suspension) yielded embodiment 1s whose diffractogram is shown in FIG. 5; toluene (75 µL, suspension) yielded embodiment 1s whose diffractogram is shown in FIG. 5; isopropyl acetate (75 µL, suspension) yielded embodiment 37 whose diffractogram is shown in FIG. 15; methyl t-butyl ether (75 µL, suspension), yielded embodiment 33 whose diffractogram is shown in FIG. 14; 2-butanone (75 µL, suspension) yielded embodiment 1s whose diffractogram is shown in FIG. 5; THF (75 µL, suspension) yielded embodiment 37 whose diffractogram is shown in FIG. 15; diethyl ether (150 µL, suspension) yielded embodiment 1s whose diffractogram is shown in FIG. 5; methyl isobutyl ketone (150 µL, suspension) yielded embodiment 33 whose diffractogram is shown in FIG. 14; DCM (75 µL, suspension) yielded embodiment 1s whose diffractogram is shown in FIG. 5; heptane (150 µL, suspension) yielded embodiment 41 whose diffractogram is shown in FIG. 15; 1,4-dioxane (75 µL, suspension) yielded embodiment 3c whose diffractogram is shown in FIG. 5; nitromethane (75 µL, suspension) yielded embodiment 42 whose diffractogram is shown in FIG. 15; propylene glycol (75 µL, suspension) yielded embodiment 43 whose diffractogram is shown in FIG. 15; 2-methyl-tetrahydrofuran (150 µL, suspension) yielded embodiment 33 whose diffractogram is shown in FIG. 14; tetralin (150 µL, suspension), yielded embodiment 33 whose diffractogram is shown in FIG. 14; 3-methyl-1-butanol (75 µL, suspension) yielded embodiment 33 whose diffractogram is shown in FIG. 14; anisole (150 µL, suspension) yielded embodiment 1s whose diffractogram is shown in FIG. 5; 1,2-dimethoxyethane (75 µL, suspension) yielded embodiment 1s whose diffractogram is shown in FIG. 5; cumene (150 µL, suspension) yielded embodiment 44 whose diffractogram is shown in FIG. 15; diisopropyl ether (150 µL, suspension) yielded embodiment 33 whose diffractogram is shown in FIG. 14; ethanol:water (95:5, 75 µL, suspension) yielded embodiment 45 whose diffractogram is shown in FIG. 15; acetonitrile:water (95:5, 75 µL, suspension) yielded embodiment 1s whose diffractogram showed cell expansion when compared to the diffractogram shown in FIG. 5; and polyethylene glycol (75 µL, suspension) yielded embodiment 46 whose diffractogram is shown in FIG. 15.

Thermocycling

Figure 16:
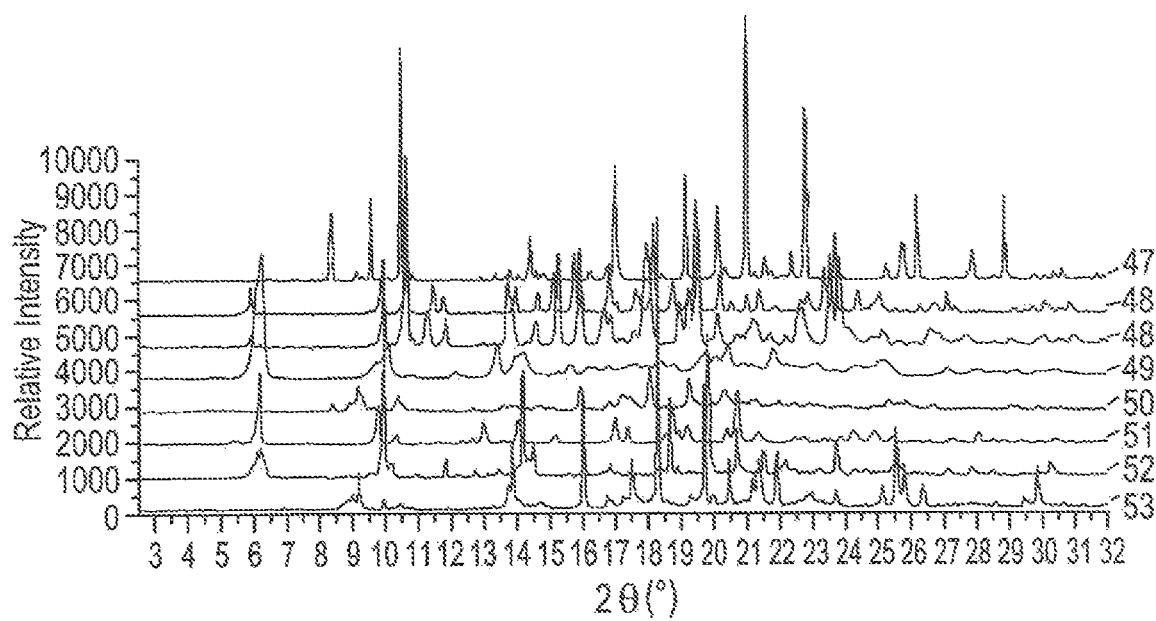
FIG. 16. Overlay of X-ray powder diffraction (XRPD) patterns for the following embodiments of compound of Formula I, from bottom to top: embodiment 53, embodiment 52, embodiment 51, embodiment 50, embodiment 49, embodiment 48 and embodiment 47.

Each of a plurality of embodiment 19 (25 mg) samples was treated with an amount of a solvent as indicated below yielding in turn a plurality of samples, each sample was matured by thermocycling (40° C.-60° C., 4 h cycles) for 24 h. Solids were isolated, air-dried for 16 h and analyzed by XRPD. The following solvents, where total solvent amount added is noted in parenthesis immediately after the solvent followed by the observed appearance at 24 hours, were used according to this procedure which yielded the noted embodiment: Water (125 µL, green tinge solid) yielded embodiment 1s whose diffractogram is shown in FIG. 5; methanol (75 µL, transparent solid) yielded embodiment 11 whose diffractogram showed peaks that were shifted at high angle when compared to the diffractogram in FIG. 7; ethanol (100 µL, green tinge solid) yielded embodiment 1s whose diffractogram is shown in FIG. 5; 2-propanol (75 µL, yellow tinge solid) yielded embodiment 33 whose diffractogram is shown in FIG. 14; 1-propanol (75 µL, white suspension) yielded embodiment 33 whose diffractogram is shown in FIG. 14; acetone (75 µL, green tinge solid) yielded embodiment 47 whose diffractogram is shown in FIG. 16; ethyl acetate (75 µL, white suspension) yielded embodiment 33 whose diffractogram is shown in FIG. 14; acetonitrile (75 µL, white suspension) yielded a poorly crystalline of embodiment 6 whose diffractogram is shown in FIG. 3; toluene (75 µL, transparent solid) yielded embodiment 36 whose diffractogram is shown in FIG. 14; isopropyl acetate (75 µL, white solid) yielded embodiment 33 whose diffractogram is shown in FIG. 14; methyl t-butyl ether (75 µL, white suspension) yielded embodiment 6 whose diffractogram is shown in FIG. 3; 2-butanone (75 µL, off-white solid) yielded embodiment 33 whose diffractogram is shown in FIG. 14; THF (75 µL, off-white solid) yielded embodiment 48 whose diffractogram is shown in FIG. 16; diethyl ether (150 µL, off-white solid) yielded embodiment 49 whose diffractogram is shown in FIG. 16; methyl isobutyl ketone (150 µL, off-white solid) yielded embodiment 25 whose diffractogram is very similar to the diffractogram for embodiment 25 that is shown in FIG. 13; DCM (125 µL, white suspension) yielded embodiment 1s whose diffractogram is shown in FIG. 5; heptane (150 µL, white solid) yielded embodiment 19 whose modified DSC profile is shown in FIG. 9; 1,4-dioxane (75 µL, white solid) yielded embodiment 3c whose diffractogram is shown in FIG. 5; nitromethane (75 µL, white suspension) yielded embodiment 50 whose diffractogram is shown in FIG. 16; propylene glycol (75 µL, cream suspension) yielded embodiment 10 whose diffractogram is very similar to the diffractogram for embodiment 10 (as shown in FIG. 16), except that it shows an amorphous halo; 2-methyltetrahydrofuran (150 µL, white solid) yielded embodiment 48 whose diffractogram is shown in FIG. 16; tetralin (150 µL, white solid) yielded a poorly crystalline embodiment whose diffractogram is not shown; 3-methyl-1-butanol (75 µL, white suspension) yielded embodiment 25 whose diffractogram is shown in FIG. 13; anisole (150 µL, white suspension) yielded embodiment 51 whose diffractogram is shown in FIG. 16; 1,2-dimethoxyethane (75 µL, white suspension) yielded embodiment 52 whose diffractogram is shown in FIG. 16; cumene (150 µL, white solid) yielded a poorly crystalline embodiment whose diffractogram is not shown; diisopropyl ether (150 µL, white solid) yielded embodiment 6 whose diffractogram is shown in FIG. 3; ethanol:water (95:5, 75 µL, transparent solid) yielded embodiment 11 whose diffractogram is shown in FIG. 7; acetonitrile:water (95:5, 75 µL, transparent solid) yielded embodiment 53 whose diffractogram is shown in FIG. 16; and propylene glycol (75 µL, pale pink suspension) yielded embodiment 31 whose diffractogram is very similar to the diffractogram for embodiment 31 (as shown in FIG. 13), except that it shows an amorphous halo.

Any one of embodiments 11, 11b, 12, 13, 14, 15, 16, 17, 18, 19, 20, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52 and 53 of compound of Formula I and any combination thereof is an embodiment of compounds according to this invention. Still other embodiments of compounds according to this invention include compound of Formula I as a non-hygroscopic solvate, such as embodiment 11 of compound of Formula I. Still other embodiments of compounds according to this invention include compound of Formula I in amorphous form, such as embodiment 19 of compound of Formula I. Any one of embodiments 11, 16, 17, and 18 of compound of Formula I and any combination thereof is an embodiment of compounds according to this invention. Further embodiments of this invention include compounds according to this invention in the form of pharmaceutically acceptable co-crystals. Additional embodiments of this invention include compounds according to this invention in the form of pharmaceutically acceptable salts.

Embodiments of this invention include compound of Formula I in at least one of the forms 1s, 1a, 1b, 1c, 1d, 1e, 1f, 1g, 1h, 2, 3b, 3c, 3d, 3e, 5, 6, 7, 8, 9, and 10. Embodiments of this invention include compound of Formula I in the form of pharmaceutically acceptable co-crystals.

Embodiments of this invention include compound of Formula I in at least one of the forms 1s, 1a, 1b, 1c, 1d, 1e, 1f, 1g, 1h, 2, 3b, 3c, 3d, 3e, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, and 53. Embodiments of this invention include compound of Formula I in the form of pharmaceutically acceptable co-crystals.

A XRPD of compound of Formula I in form 1s is shown in FIG. 25. A listing of the major peaks includes those at 2θ values of 6.13±0.2, 9.88±0.2, 10.26±0.2, 13.39±0.2, 14.52±0.2, 16.64±0.2, 18.24±0.2, 19.98±0.2, 20.58±0.2, and 22.01±0.2.

The compound of Formula I was tested in enzymatic and cellular assays. The results of the enzymatic assay and description of the same are presented in Table 4, which is entitled Results of Enzymatic Inhibition Assays, and columns 51-54 in U.S. Pat. No. 10,294,226, issued May 21, 2019, which is incorporated herein by reference in its entirety. This compound was also tested in three cellular assays: IL-2 pSTAT5 (JAK1/JAK3), IFNα pSTAT-4 (JAK1/TYK2) and GM-CSF pSTAT5 (JAK2/JAK2) with the results and assay description presented in Table 5 entitled Cell-Based Assay Data and column 53-55 in U.S. Pat. No. 10,294,226, which is incorporated herein by reference in its entirety.

Compound of Formula I was tested in solubility and permeability assays. The results of the solubility assay are presented in Table 6 which is entitled Solubility Assay Data and the results of the permeability assay are presented in Table 7 entitled MDCK-MDR1 Permeability Data, and columns 55-58 in U.S. Pat. No. 10,294,226, which is incorporated herein by reference in its entirety.

Compound of Formula I was tested according to protocols as described in columns 21-22 and 58-59 and Table 1a in U.S. Pat. No. 10,294,226, which is incorporated herein by reference in its entirety.

Compound of Formula I was further characterized by the physico-chemical properties as described and given in Table 8, column 59, in U.S. Pat. No. 10,294,226, which is incorporated herein by reference in its entirety.

Compound of Formula I was further characterized by the description of embodiments 11, 11b, 12, 15, 16, 17, 18, 19, 20, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52 and 53. as described and given in FIGS. 7A, 7B, 7C, 7D, 7E and 8-23 and paragraphs [0328]-[0348] in US patent application US2020/0165250 published on May 28, 2020, which is incorporated herein by reference in its entirety.

Amounts in mg in the examples below refer to amounts of active agent in the form of compound of Formula I. The appropriate correction should be made if what is administered is an active agent in another form, such as a pharmaceutically acceptable salt.

EXAMPLE 2

In Vivo Studies

Compound of Formula I demonstrated high colonic exposure and tissue target engagement in mice, with low systemic exposure after oral dosing in an IL-12/IL-18-induced STAT3 phosphorylation assay in colon tissue, and in an ex vivo cytokine-stimulated colon explant study. Oral dosing of compound of Formula I in mice resulted in minimum systemic exposure and lack of consistent dose-dependent pharmacodynamic responses in the blood, as determined by ex vivo whole blood stimulation with either interferon-alpha (IFNα) or IL-21.

Compound of Formula I presents low levels of systemic exposure after oral administration. To understand the relationship between systemic exposure and target engagement in human studies, the inhibition of cytokine-induced pSTAT-3 in human whole blood was measured with such compound. In human whole blood, compound of Formula I in a concentration-dependent manner inhibited the JAK1, JAK2, JAK3, and Tyk2 homo- and heterodimers downstream of IFNα (JAK1/Tyk2), thrombopoietin (TPO) (JAK2/JAK2), and IL-21 (JAK1/JAK3) signaling. The mean $IC_{50}$ values for IFNα-, TPO-, and IL-21-mediated STAT3 phosphorylation with compound of Formula I was 105.3 nM, 490.4 nM and 579.2 nM, respectively as shown in Table 3, in which results are reported for compound of Formula I.

TABLE 3

$IC_{50}$ of compound of Formula I for cytokine-induced pSTAT in human and murine whole blood

| Compound of Formula I | $IC_{50}$/nM | 95% CI[a] | n[c] |
|---|---|---|---|
| Human IFNα[b] (pSTAT-3) | 105.3 | 84.0-131.9 | 4 |
| Human TPO[e] (pSTAT-3) | 490.4 | 282.1-852.7 | 2 |
| Human IL-21 (pSTAT-3) | 579.2 | 536.2-625.7 | 2 |
| Murine IFNα[b] (pSTAT-3) | 298.6 | 121.7-733.1 | 2 |
| Murine IL-21 (pSTAT-3) | 415.1 | 308.1-559.4 | 3 |
| Murine IL-12 (pSTAT-4) | ND[d] | | |

[a]CI, confidence interval;
[b]IFNα, interferon alpha;
[c]n, number of trials;
[d]ND, not determined, does not converge;
[e]TPO, thrombopoietin.

Mouse whole blood $IC_{50}$ values were also generated to build an understanding of the relationship between systemic exposures and target engagement in murine models. In murine whole blood, the in vitro activity of compound of Formula I in the inhibition of IFNα-(JAK1/Tyk2), IL-21-(JAK1/3), and IL-12-(JAK2/Tyk2) induced pSTAT responses in murine whole blood was measured. Results shown in Table 3 demonstrated that compound of Formula I inhibited IFNα and IL 21 responses with IC50 values of 298.6 nM and 415.1 nM, respectively. No reliable $IC_{50}$ could be reported for inhibition of IL-12 induced pSTAT-4 in murine whole blood.

To understand the potential of local, enteric-selective JAK inhibitors to inhibit STAT signaling in colon tissue, two pharmacokinetic/pharmacodynamic (PK/PD) studies were developed. The first involved the combined intraperitoneal administration of IL-12 and IL-18 in mice which induces a systemic inflammatory response resulting in activation of the JAK/STAT pathway in colonic tissue which can be monitored by robust phosphorylation of STAT3 three hours after challenge. The second PK/PD model involves the ex vivo stimulation of mouse colon tissue with a cocktail of cytokines (IL-22, IL-6, and IFNα), measuring the inhibition of STAT3 phosphorylation after oral dosing of compound of Formula I.

The combined intraperitoneal administration of IL-12 and IL-18 induces colonic inflammation in mice (Chikano S, et al. Gut 47(6),779-786 (2000) "IL-18 and IL-12 induce intestinal inflammation and fatty liver in mice in an IFN-gamma dependent manner"; Nold-Petry C, et al. Front Immunol. 8, 1531(2017) "Gp96 Antagonist Protects in Murine-Intestinal-Inflammation"). An inflammatory response in colonic tissue can be monitored by robust phosphorylation of STAT3 three hours after challenge with IL 12/IL-18. In this non-GLP study, the effect of the orally administered compound of Formula I was evaluated on STAT3 responses in mouse colonic tissue induced by systemic dosing of both IL-12 and IL 18.

C57BL/6 mice (6 to 8 weeks old) were randomized by weight and assigned to various treatment groups for each of two studies. Mice were challenged intraperitoneally with a combination of IL-12 (250 ng) and IL-18 (1 μg). To examine the effect of compound of Formula I on IL-12/IL-18-induced pSTAT-3 response, groups of mice were orally dosed with compound of Formula I 1 hour prior to IL-12/IL-18 challenge. Three hours after IL-12/IL-18 challenge, mice were euthanized with $CO_2$ asphyxiation, blood was collected via cardiocentesis for PK analysis, and colon tissues were collected for measuring pSTAT-3 response and drug levels. Mice dosed orally with 20% 2-hydroxypropyl-β-cyclodextrin (HP-β-CD) were used as vehicle controls. Two independent studies (S-1 and S-2) were conducted to examine the effect of compound of Formula I on IL-12/IL-18-induced colonic pSTAT-3 response in mice. A significant increase in colonic pSTAT-3 following IL-12/IL-18 challenge was seen in both studies. In both experiments, compound of Formula I showed a clear trend for dose-related inhibition of pSTAT-3 response: 3.9% and 33.1% inhibition at 10 mg/kg; 25.8% and 61.2% at 25 mg/kg; and 49.7% and 66.1% at 50 mg/kg (Table 4). Statistical analyses indicated a lack of significance of inhibition in S-1, but significant inhibition was achieved at 25 mg/kg and 50 mg/kg doses in S-2. Serum levels were measured at 30 minutes and 4 hours (terminal) after dosing. As shown in Tables 5 and 6 below, compound of Formula I exhibited low systemic exposure at all tested doses at 30 minutes (nM, mean±SEM; 7.4±1.4 and 7.0±0.7 at 10 mg/kg; 21.8±5.5 mg/kg and 70.5±60.4 at 25 mg/kg; 121.7±87.2 mg/kg and 38.8±7.4 at 50 mg/kg dose). The observed serum exposure of compound of Formula I was significantly lower than murine whole blood $IC_{50}$ for IL-21-induced pSTAT-3 and IFNα-induced pSTAT-3 and pSTAT-4 as shown in Table 3. Colon drug levels were measured 4 hours after dosing. Relative to serum, high drug levels were observed in the colon samples of mice treated with compound of Formula I (Tables 5 and 6). Colonic exposure of compound of Formula I increased in a dose-dependent fashion. At 25 mg/kg dose, colonic exposure of compound of Formula I was 30814.5±5552.5 ng/g and 18256.5±4118.8 ng/g tissue. Taken together, serum and colonic exposure data suggest that the pharmacological response of compound of Formula I appears to be driven primarily by tissue exposure of the drug. Compound of Formula I demonstrates in vivo target engagement through the inhibition of IL-12/IL-18-induced pSTAT-3 in the colon with high colonic and low systemic exposures. Oral dosing of compound of Formula I in mice resulted, as shown in other studies, in minimum systemic exposure and lack of consistent dose-dependent pharmacodynamic responses in the blood.

TABLE 4

Inhibition of Colonic pSTAT-3 by compound of Formula I

| Treatment | Study S-1 Percent Inhibition | 95% CI | Study S-2 Percent Inhibition | 95% CI |
|---|---|---|---|---|
| Compound of Formula I (10 mg/kg) | 3.9 | −19.9 to 22.1 | 33.1 | 20.5 to 43.8 |
| Compound of Formula I (25 mg/kg) | 25.8 | −29.4 to 57.5 | 61.2 | 47.5 to 71.3 |
| Formula I (50 mg/kg) | 49.7 | 38.6 to 58.8 | 66.1 | 49.9 to 74.2 |

Percent inhibition of colonic pSTAT-3 was determined using log transformed data following outlier removal.

TABLE 5

IL-12/IL-18 S-1 - Serum and Colonic Concentrations of compound of Formula I

| Treatment | Serum (nM) 30 min post dosing | Serum (nM) 4 h post dosing | Colon (ng/g) 4 h post dosing |
|---|---|---|---|
| Compound of Formula I (10 mg/kg) | 7.4 ± 1.4 | BLOQ | 6596.5 ± 787.2 |
| Compound of Formula I (25 mg/kg) | 21.8 ± 5.5 | 25.0 ± 20.3 | 30814.5 ± 5552.5 |
| Compound of Formula I (50 mg/kg) | 121.7 ± 87.2 | 19.7 ± 8.0 | 59608.5 ± 11250.7 |

Data are presented as mean±SEM; N=3-7/group. BLOQ, below limit of quantification; min, minutes; h, hour(s).

TABLE 6

IL-12/IL-18 S-2 - Serum and Colonic Concentrations of compound of Formula I

| Treatment | Serum (nM) 30 min post dosing | Serum (nM) 4 h post dosing | Colon (ng/g) 4 h post dosing |
|---|---|---|---|
| Compound of Formula I (10 mg/kg) | 7.0 ± 0.7 | BLOQ | 10131.5 ± 1304.2 |
| Compound of Formula I (25 mg/kg) | 70.5 ± 60.4 | 45.1 ± 24.0 | 18256.5 ± 4118.8 |
| Compound of Formula I (50 mg/kg) | 38.8 ± 7.4 | 130.7 ± 107.7 | 35578.8 ± 5563.6 |

Data are presented as mean±SEM; N=3 to 7/group. BLOQ, below limit of quantification; min, minutes; h, hour(s).

In addition to the IL-12/IL-18 model described above, local efficacy of compound of Formula I was further established in a mouse cytokine mixture (IL-22/IL-6/IFNα) colon explant model. A combination of IL-22, IL-6 and IFNα induced a rapid and robust pSTAT-3 response in mouse colon explants ex vivo 1 hour post challenge. This study aimed at examining the dose response and duration of action of compound of Formula I on IL 22/IL 6/IFNα-induced pSTAT-3 response in an ex vivo mouse colon explant model.

C57BL/6 mice (6 to 8 weeks old) were randomized by weight and assigned to various treatment groups for each study. Mice were dosed orally with indicated doses of compound of Formula I. At the termination of the study, blood was collected via cardiocentesis, serum and washed proximal colon was prepared for PK analysis.

Distal colon explants (approximately 3 mm$^2$) were either untreated or treated with cytokines (IL 6, IL-22, IFNα at 100 ng/mL each). Following stimulation for 1 hour, tissue was snap-frozen for homogenization and assayed for pSTAT-3. In 2 independent experiments, SS-1 and SS-2, compound of Formula I dose dependently inhibited colonic pSTAT-3. In SS-1, compound of Formula I inhibited basal pSTAT-3 response by 54.3, 74.4, 78.6, and 89.5% at 0.5, 2.5, 5, and 25 mg/kg, respectively. IL 22/IL-6/IFNα-stimulated pSTAT-3 response was similarly inhibited with compound of Formula I by 42.7, 74.9, 83.8, and 93.8% at 0.5, 2.5, 5, and 25 mg/kg, respectively. In SS-2, basal pSTAT-3 was inhibited by 36.7, 66.2, 71.3, and 83.8% at 0.5, 2.5, 5, and 25 mg/kg doses of compound of Formula I, respectively. IL-22/IL-6/IFNα-stimulated pSTAT-3 was inhibited by 5.5, 62.0, 68.1, and 89.8% at 0.5, 2.5, 5, and 25 mg/kg, respectively, with compound of Formula I. Thus, compound of Formula I demonstrated robust target engagement in the colon tissue ex vivo through the inhibition of IL 22/IL 6/IFNα induced pSTAT-3 response.

As shown in Tables 7 and 8, the effects of compound of Formula I were accompanied by low systemic (serum) (≤10.3±6.9 nM) and high colonic exposure of compound of Formula I (27488.1±6128.6 ng/g and 22929.6±4146.6 ng/g in SS-1 and SS-2 at 25 mg/kg, respectively). The high colonic and low systemic exposure observed for compound of Formula I implicate the role for colonic drug levels as the key driver of the observed pharmacology. Compound of Formula I demonstrated colonic tissue target engagement at 4 hours post oral dosing.

TABLE 7

Study SS-1 - Serum and Colon Concentration of compound of Formula I (4 hours post oral dose)

| Treatment Groups | Serum (nM) | Colon (ng/g) |
|---|---|---|
| Compound of Formula I (0.25 mg/kg) | BLOQ | 446.2 ± 51.5 |
| Compound of Formula I (2.5 mg/kg) | BLOQ | 2842.3 ± 715.9 |
| Compound of Formula I (5 mg/kg) | BLOQ | 4628.5 ± 705.1 |
| Compound of Formula I (25 mg/kg) | 4.9 ± 2.1 | 27488.1 ± 6128.6 |

Data are presented as mean±SEM; N=5/group. BLOQ, below limit of quantification.

TABLE 8

Study SS-2 - Serum and Colon Concentration of compound of Formula I (4 hours post oral dose)

| Treatment Groups | Serum (nM) | Colon (ng/g) |
|---|---|---|
| Compound of Formula I (0.25 mg/kg) | BLOQ | 261.5 ± 30.5 |

TABLE 8-continued

Study SS-2 - Serum and Colon Concentration of
compound of Formula I (4 hours post oral dose)

| Treatment Groups | Serum (nM) | Colon (ng/g) |
|---|---|---|
| Compound of Formula I (2.5 mg/kg) | BLOQ | 1323.6 ± 270.2 |
| Compound of Formula I (5 mg/kg) | 10.3 ± 6.9 | 4672.4 ± 952.6 |
| Compound of Formula I (25 mg/kg) | 6.3 ± 2.9 | 22929.6 ± 4146.6 |

Data are presented as mean±SEM; N=5/group. BLOQ, below limit of quantification.

Limited tissue (liver, intestine) distribution studies were conducted in female C57Bl/6 mice (N=3/time point) at 0.5, 1, 2, 3, 5, 7, and 24 hours following oral administration of compound of Formula 1 at a dose of 10 mg/kg formulated as a solution in 20% HP-β-CD. The plasma and the following tissues were harvested for compound concentration analysis: liver, whole ileum, and whole colon. The ileum and colon were flushed with saline prior to homogenization. Feces were collected over a period of 24 hours. All tissues (except plasma) were homogenized in sterile water and compound of Formula I concentrations were determined using LC-MS/MS. Results of this study demonstrated that the highest tissue concentrations were seen in ileum>colon>liver>plasma (see Table 9). The concentration of compound of Formula I in feces was 125.6 µg at 24 hours post dose.

TABLE 9

Compound of Formula I concentrations (mean ± SD) in plasma (ng/mL) and tissues (ng/g) from mice following oral administration of compound of Formula I at 10 mg/kg compound

| Time (h) | Plasma[a] | Liver[a] | Ileum[a] | Colon[a] |
|---|---|---|---|---|
| 0.5 | 3.5 ± 1.8 | 34.8 ± 16.5 | 73.8 ± 11.6 | 94.2[c] |
| 1 | 2.6 ± 0.9 | 189.2 ± 303.8 | 22,716 ± 18,206 | 5,107 ± 2,300 |
| 2 | 2.3 ± 0.2 | 84.5 ± 113.9 | 11,984 ± 12,650 | 6,621 ± 2,473 |
| 3 | 3.2 ± 1.7 | 23.3 ± 0.8 | 16,372 ± 21,999 | 7,763 ± 5,445 |
| 5 | 2.1 ± 0.9 | 16.8 ± 8.8 | 3,440 ± 2,377 | 8,452 ± 6,755 |
| 7 | 6.0 ± 4.9 | 24[c] | 2,254 ± 1,552 | 3,787 ± 2,560 |
| 24 | BLOQ[b] | BLOQ[b] | 87.6 ± 17.8 | 195.0 ± 119.5 |

[a]Values are the average ± SD (N = 3 animals).
[b]BLOQ (1 ng/mL)
[c]N = 2 (SD not calculated)

BLOQ = below limit of quantification; N = number of animals; PO = oral administration; SD = standard deviation.

Preliminary tissue distribution studies were conducted in male Sprague-Dawley rats (N=3/time point) at 0.5, 1, 2, 3, 5, 7, and 24 hours following oral administration of compound of Formula I at a dose of 25 mg/kg. The following tissues were harvested for compound concentration analysis: liver, kidney, brain, muscle, epididymis fat, duodenum, jejunum, ileum, colon (both lumen content and tissue), and plasma. Compound concentrations in various tissues are shown in Tables 10 and 11. The results of this study indicated low systemic exposure and high local concentrations (intestinal tract).

TABLE 10

Average (±SD) Concentrations of compound of Formula I in Plasma (ng/mL) and Tissues (ng/g) after PO Administration to Rats at 25 mg/kg (N = 3)

| Time (h) | Plasma | Brain | Liver | Kidney | Fat | Muscle |
|---|---|---|---|---|---|---|
| 0.5 | 6.3 ± 1.1 | 3.5 ± 3.1 | 158.3 ± 104.5 | 57.9 ± 26.2 | NC[b] | 16.7 ± 15.0 |
| 1 | 5.8 ± NA | BLOQ[a] | 70.4 ± NA[c] | 42.2 ± NA | BLOQ[a] | NC[b] |
| 2 | 3.7 ± 0.9 | BLOQ[a] | 49.9 ± 17.5 | 24.3 ± 6.6 | BLOQ[a] | BLOQ[a] |
| 3 | 3.1 ± 1.1 | BLOQ[a] | 29.6 ± 14.5 | 30.0 ± 9.4 | NC[b] | BLOQ[a] |
| 5 | 1.5 ± 0.7 | BLOQ[a] | 18.7 ± 3.0 | 12.9 ± 3.6 | BLOQ[a] | BLOQ[a] |
| 7 | 2.1 ± 0.5 | BLOQ[a] | 20.7 ± 3.0 | 19.9 ± 7.8 | NC[b] | NC[b] |
| 24 | BLOQ[a] | BLOQ[a] | NC[b] | BLOQ[a] | BLOQ[a] | BLOQ[a] |

[a]BLOQ is below the limit of quantification (0.5 ng/mL of tissue homogenate).
[b]NC = mean not calculated if 2 of 3 samples were BLOQ. Concentration < BLOQ set to 0 for calculation of average.
[c]NA = not applicable/available

TABLE 11

Average (±SD) Concentrations of compound of Formula I in Intestinal Tissues (ng/g) and Luminal Content (ng/mL) after PO Administration to Rats at 25 mg/kg (N = 3)

| Time (h) | Duod. Tissue | Duod. Content | Jejunum Tissue | Jejunum Content | Ileum Tissue | Ileum Content | Colon Tissue | Colon Content |
|---|---|---|---|---|---|---|---|---|
| 0.5 | 35,218 (20,130) | 329,131 (244,942) | 47,151 (29,570) | 533,362 (110,888) | 1,344 (1,402) | 644 (490) | 946 (778) | 167 (114) |
| 1 | 16,677 (3,118) | 45,490 (38,125) | 23,515 (11,992) | 248,713 (250,506) | 252 (327) | 496 (580) | 383 (433) | 135 (135) |
| 2 | 3,166 (771) | 20,152 (14,982) | 8,228 (1,335) | 90,654 (35,194) | 8,946 (15,106) | 725,330 (850,701) | 2,186 (3,233) | 19,142 (32,168) |
| 3 | 3,841 (2,070) | 15,830 (13,969) | 3,976 (699) | 47,965 (18,323) | 50,844 (48,225) | 1,402,241 (586,593) | 12,419 (4,622) | 303,661 (163,980) |
| 5 | 1,100 (573) | 4,470 (2,760) | 1,814 (1,725) | 26,264 (25,181) | 17,958 (17,841) | 596,702 (72,699) | 33,538 (7,182) | 830,129 (57,295) |
| 7 | 366 (184) | 2,626 (2,537) | 788 (466) | 10,264 (5,915) | 6,487 (5,732) | 133,499 (117,744) | 36,748 (28,645) | 833,597 (156,490) |

TABLE 11-continued

Average (±SD) Concentrations of compound of Formula I in Intestinal Tissues (ng/g)
and Luminal Content (ng/mL) after PO Administration to Rats at 25 mg/kg (N = 3)

| Time (h) | Duod. Tissue | Duod. Content | Jejunum Tissue | Jejunum Content | Ileum Tissue | Ileum Content | Colon Tissue | Colon Content |
|---|---|---|---|---|---|---|---|---|
| 24 | 17 (16) | 60 (52) | 27 (28) | 228 (236) | NC[a] | 893 (962) | 353 (54) | 7,593 (2,012) |

[a]NC, mean not calculated if 2 of 3 samples were BLOQ (0.5 ng/mL of tissue homogenate).
BLOQ = below limit of quantification; Duod = duodenum; N = number of animals; NC = not calculated; PO = oral administration; SD = standard deviation.

EXAMPLE 3

A Phase 1b Study to Evaluate the Efficacy and Safety of Compound of Formula I, a Janus Kinase (JAK) Inhibitor, in Participants with Familial Adenomatous Polyposis Compound of Formula I is an oral, small molecule, potent pan-Janus kinase (JAK) inhibitor with favorable enteric-selective properties based on permeability and solubility. Inhibition of this group of cytoplasmic tyrosine kinases interferes with the phosphorylation of Signal Transducer and Activator of Transcription (STAT) proteins. Phosphorylated STATs (pSTAT) translocate to the nucleus and induce gene transcription of several chemokines, cytokines and proteases implicated in the pathogenesis of rheumatoid arthritis, inflammatory bowel disease, familial adenomatous polyposis (FAP), and other inflammatory diseases.

Objectives and Endpoints

The primary objective of this study is to determine the effect of compound of Formula I on colorectal polyp burden (sum of polyp burden) in participants with FAP. Key secondary objectives are to assess the safety, other measures of efficacy, the local and systemic pharmacokinetics (PK), and pharmacodynamics (PD) in polyps.

Overall Design

This is a Phase 1b multicenter study to evaluate the efficacy and safety of compound of Formula I in adult participants with FAP. The study is designed to determine if compound of Formula I has clinical activity in the colorectum and duodenum as assessed by a reduction in the number of polyps and a decrease in JAK signaling in polyps over a period of 24 weeks. Participants may be either pre- or postcolectomy, however, all participants are required to have colon or rectal polyps. All participants are required to have a genetic diagnosis of classical FAP, ie, adenomatous polyposis coli (APC) germline mutation or obligate carrier, with disease involvement of the colorectum. Participants with attenuated FAP are not eligible.

Number of Participants

This study will enroll approximately 40 participants (approximately 20 each of post-colectomy and pre-colectomy).

Treatment Groups and Duration

All participants will receive compound of Formula I 75 mg twice daily. Total duration of study participation for each participant is approximately 32 weeks consisting of screening (30 days), treatment (24 weeks) and follow-up visit (approximately 30 days after last dose of study drug).

compound of Formula I will be manufactured and provided under the responsibility of the sponsor as 75 mg tablets.

Efficacy Evaluations

All participants will undergo efficacy evaluations at Week 24. Evaluations will include lower GI polyp burden, duodenum polyp burden, and disease response which will be performed by the investigator.

Pharmacokinetic Evaluations

Venous blood samples and tissue samples from the lower GI tract (gut mucosa and polypectomy) will be collected for measurement of plasma concentrations and tissue concentrations of compound of Formula I at the time points indicated in the Schedule of Activities.

Pharmacodynamic and Biomarker Evaluations

Biomarkers will be used to assess the effects of compound of Formula I on molecular and cellular effectors of the JAK/STAT pathway in blood, tissue biopsies and stool samples collected from FAP patients. The relationships between dose regimen, PK, biomarker changes, and efficacy will then be evaluated, and will guide dose optimization if additional doses are evaluated.

Safety Evaluations evaluations will include the assessment of adverse events (AE), serious adverse events (SAEs), events of infections including tuberculosis (TB), clinical laboratory blood tests (complete blood count and serum chemistries), vital signs, endoscopies, and concomitant medication review. In addition to local testing, central cholesterol testing will be conducted.

Statistical Methods

No formal statistical hypothesis testing will be conducted in this study. Specific details of statistical methods will be provided in the Statistical Analysis Plan.

The sample size of approximately 20 for the cohort of post-colectomy participants was calculated by assuming that polyp burden would decrease, on average, by at least 25% by Week 24 from baseline. A dropout rate of 20% was assumed. A standard deviation of 30 percentage points was assumed for the percentage change in polyp burden by Week 24 from baseline. With these assumptions, a 95% confidence interval for the percentage change in polyp burden by Week 24 from baseline has approximately 90% or greater probability to have its upper limit be less than 0% and thereby provide evidence that treatment with compound of Formula I, on average, reduces polyp burden. A sample size of approximately 20 was similarly determined for the cohort of pre-colectomy patients.

| OBJECTIVES AND ENDPOINTS | |
| --- | --- |
| Objectives | Endpoints |
| Primary | |
| Determine the effect of compound of Formula I in participants with FAP on colorectal polyp burden (sum of the polyp diameters) | Percentage change from baseline in colorectal polyp burden for all polyps and for polyps ≥2 mm at Week 24 |
| Secondary | |
| Determine the effect of treatment with compound of Formula I in participants with FAP | Percentage change in number of colon, rectal, J-pouch and duodenal polyps<br>Percentage change in colon, rectal, J-pouch and duodenal polyp burden for all polyps, polyps ≥2 mm, and polyps ≥5 mm<br>Change in International Society for Gastrointestinal Hereditary Tumors (InSiGHT) polyposis stage<br>Change in Spigelman score |
| Evaluate the safety of compound of Formula I in participants with FAP | Incidence and severity of adverse events |
| Assess the systemic and local pharmacokinetics (PK) of compound of Formula I in participants with FAP | Plasma and tissue concentration of compound of Formula I over time |
| Assess biomarkers of compound of Formula I activity and response in polyp and tissue samples. | Levels of JAK/STAT pathway signaling effector proteins, including pSTAT-3, relative to baseline levels in colorectal polyps |

Aspects:

Aspect 1: Compound of Formula I or a pharmaceutically acceptable salt, solvate, polymorph thereof for use in treating or preventing familial adenomatous polyposis a subject comprising administering to the subject a therapeutically effective amount of compound of Formula I.

Aspect 2: Compound of Formula I or a pharmaceutically acceptable salt, solvate, and polymorph thereof for use in treating or preventing stomacho-intestinal system cancer a subject comprising administering to the subject a therapeutically effective amount of compound of Formula I.

Aspect 3: Compound of Formula I or a pharmaceutically acceptable salt, solvate, and polymorph thereof for use in treating or preventing colorectal cancer a subject comprising administering to the subject a therapeutically effective amount of compound of Formula I.

Aspect 4: Compound of Formula I or a pharmaceutically acceptable salt, solvate, and polymorph thereof for use in treating or preventing familial adenomatous polyposis or colorectal cancer a subject who is in a high-risk group comprising administering to the subject a therapeutically effective amount of compound of Formula I.

Aspect 5: Compound of Formula I or a pharmaceutically acceptable salt, solvate, and polymorph thereof for use in treating or preventing familial adenomatous polyposis or colorectal cancer a subject comprises: (a) determining a mutation in one or more genes selected from KRAS, TP53, EGFR, STK11 (LKB1), PTEN, BMPR1A, SMAD4 (MADH/DPC4), MLH1, MSH2, MSH6, PMS2, EPCAM, MUTYH (MYH), POLD1, POLE and APC; and (b) administering a therapeutically effective dose of compound of Formula I.

Aspect 6: Compound of Formula I or a pharmaceutically acceptable salt, solvate, and polymorph thereof for use in diagnosing whether the subject has a high risk of developing colorectal cancer or familial adenomatous polyposis comprises: (a) determining a mutation in one or more genes selected from KRAS, TP53, EGFR, STK11 (LKB1), PTEN, BMPR1A, SMAD4 (MADH/DPC4), MLH1, MSH2, MSH6, PMS2, EPCAM, MUTYH (MYH), POLD1, POLE and APC; and (b) administering a therapeutically effective dose of compound of Formula I.

Aspect 7: Compound of Formula I or a pharmaceutically acceptable salt, solvate, and polymorph thereof for use in treating or preventing a disorder or condition that is affected by the inhibition of JAK a subject comprising administering to the subject a therapeutically effective amount of compound of Formula I.

Aspect 8: Compound of Formula I or a pharmaceutically acceptable salt, solvate, and polymorph thereof for use in treating or preventing a relapse of CRC in a subject comprising administering to the subject a therapeutically effective amount of compound of Formula I.

Aspect 9: Compound of Formula I or a pharmaceutically acceptable salt, solvate, and polymorph thereof for use in treating or preventing a relapse of FAP in a subject comprising administering to the subject a therapeutically effective amount of compound of Formula I.

Aspect 10: Compound of Formula I or a pharmaceutically acceptable salt, solvate, and polymorph thereof for use in treating or preventing SISC in a subject who has been diagnosed with irritable bowel disease (IBD) comprising administering to the subject a therapeutically effective amount of compound of Formula I.

Aspect 11: Compound of Formula I or a pharmaceutically acceptable salt, solvate, and polymorph thereof for use in preventing pre-malignant condition from becoming malignant condition in a subject comprising administering to the subject a therapeutically effective amount of compound of Formula I.

Aspect 12: The use according to any one of aspects 1-11, wherein the therapeutically effective amount of compound of Formula I is from about 10 mg to about 1000 mg, Aspect 13: The use according to any one of aspects 1-12, wherein the therapeutically effective amount of compound of Formula I is from about 1 mg to about 100 mg, Aspect 14: The use according to any one of aspects 1-13, wherein the compound of Formula I is administered once daily.

Aspect 15: The use according to any one of aspects 1-14, wherein the compound of Formula I is administered twice daily.

Aspect 16: The use according to any one of aspects 1-15, wherein the subject has previously received a therapy or is currently receiving a therapy.

Aspect 17: The use according to any one of aspects 1-16, wherein the therapy may be surgery, radiation therapy, chemotherapy. NSAIDs, Cox-2 inhibitors, EGFR inhibitors, VEGF inhibitors, and checkpoint inhibitors.

Aspect 18: The use according to any one of aspects 1-17, where in treating FAP comprises reducing the poly burden in the subject.

Aspect 19: The use according to any one of aspects 1-18, where reducing polyp burden comprises decrease in the number of polyps and a decrease in the size of polyps.

Aspect 20: The use according to any one of aspects 1-19, wherein the subject in a high-risk group comprises a subject having irritable bowel syndrome, presence of gut microbiome, a family history of colorectal cancer, a prior history of colorectal cancer, a finding of a polyp or precancerous lesion during colonoscopy, or other genetic factors, such as mutations in KRAS, TP53, EGFR, STK11 (LKB1), PTEN, BMPR1A, SMAD4 (MADH/DPC4), MLH1, MSH2, MSH6, PMS2, EPCAM, MUTYH (MYH), POLD1, POLE and APC genes.

Aspect 21: The use according to any one of aspects 1-20, further comprising administering a second active agent in combination with the compound of Formula I, wherein the second active agent is selected from NSAIDs, Cox-2 inhibitors, cetuximab, panitumumab, bevacizumab, Ziv-aflibercept, regorafenib, ramucirumab, ipilimumab, nivolumab, and pembrolizumab.

Aspect 22: A method of predicting a response to compound of Formula I in a subject in need thereof comprising:
(a) measuring level of pSTAT-3 in a subject's control sample that has not been exposed to compound of Formula I;
(b) measuring a level of pSTAT-3 in a subject's test sample that has been exposed to compound of Formula; and
(c) comparing the level of pSTAT-3 in (a) to (b), wherein a decrease in the level of pSTAT-3 in (b) is predictive of a response to the compound of Formula I in the subject.

Aspect 23. A method of monitoring an efficacy of an ongoing JAK inhibitor therapy in a subject in need thereof comprising:
(a) measuring level of pSTAT-3 in a subject's control sample that has not been exposed to compound of Formula I;
(b) measuring a level of pSTAT-3 in a subject's test sample that has been exposed to compound of Formula and
(c) comparing the level of pSTAT-3 in (a) to (b), wherein a decrease in the level of pSTAT-3 in (b) is indicative of efficacy of compound of Formula I in the subject.

What is claimed is:

1. A method of treating familial adenomatous polyposis in a subject in need thereof comprising administering to the subject a composition comprising about 75 mg of compound of Formula I or a pharmaceutically acceptable salt thereof twice daily

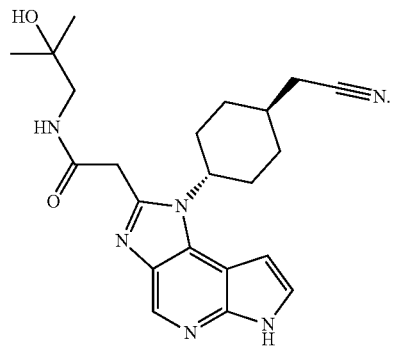

(I)

2. A method of treating stomacho-intestinal system cancer in a subject in need thereof comprising administering to the subject a composition comprising about 75 mg of compound of Formula I or a pharmaceutically acceptable salt thereof twice daily

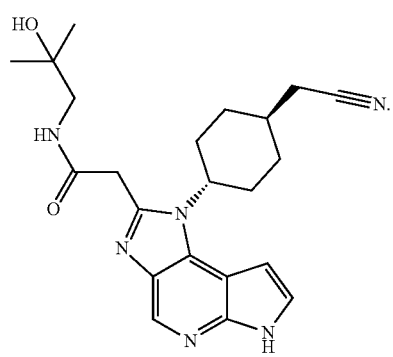

(I)

3. A method of treating colorectal cancer in a subject in need thereof comprising administering to the subject a composition comprising about 75 mg of compound of Formula I or a pharmaceutically acceptable salt twice daily

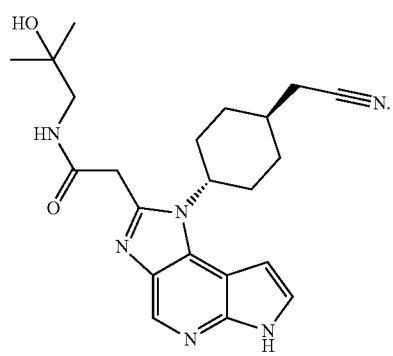

(I)

4. The method of claim 1, wherein the subject has previously received a therapy or is currently receiving a therapy.

5. The method of claim 4, wherein the therapy is selected from surgery, radiation therapy, chemotherapy, NSAIDs, Cox-2 inhibitors, EGFR inhibitors, VEGF inhibitors, and checkpoint inhibitors.

6. The method of claim 1, further comprising administering a second active agent in combination with the compound of Formula I, wherein the second active agent is selected from NSAIDs, Cox-2 inhibitors, cetuximab, panitumumab, bevacizumab, Ziv-aflibercept, regorafenib, ramucirumab, ipilimumab, nivolumab, and pembrolizumab.

7. The method of claim 2, wherein the subject has previously received a therapy or is currently receiving a therapy.

8. The method of claim 7, wherein the therapy is selected from surgery, radiation therapy, chemotherapy, NSAIDs, Cox-2 inhibitors, EGFR inhibitors, VEGF inhibitors, and checkpoint inhibitors.

9. The method of claim 2, further comprising administering a second active agent in combination with the compound of Formula I, wherein the second active agent is selected from NSAIDs, Cox-2 inhibitors, cetuximab, panitumumab, bevacizumab, Ziv-aflibercept, regorafenib, ramucirumab, ipilimumab, nivolumab, and pembrolizumab.

10. The method of claim 3, wherein the subject has previously received a therapy or is currently receiving a therapy.

11. The method of claim 10, wherein the therapy is selected from surgery, radiation therapy, chemotherapy, NSAIDs, Cox-2 inhibitors, EGFR inhibitors, VEGF inhibitors, and checkpoint inhibitors.

12. The method of claim 3, further comprising administering a second active agent in combination with the compound of Formula I, wherein the second active agent is selected from NSAIDs, Cox-2 inhibitors, cetuximab, panitumumab, bevacizumab, Ziv-aflibercept, regorafenib, ramucirumab, ipilimumab, nivolumab, and pembrolizumab.

* * * * *